(12) United States Patent
Rosner

(10) Patent No.: US 9,238,682 B2
(45) Date of Patent: Jan. 19, 2016

(54) ANTI-CANCER THERAPEUTIC STRATEGY TO OVERCOME CANCER RESISTANCE AND TO ENABLE TAILORING TREATMENT TO PATIENTS

(76) Inventor: Karli Rosner, Bloomfield Township, MI (US)

( * ) Notice: Subject to any disclaimer, the term of this patent is extended or adjusted under 35 U.S.C. 154(b) by 0 days.

(21) Appl. No.: 13/392,233

(22) Filed: Feb. 24, 2012

(65) Prior Publication Data
US 2012/0328590 A1 Dec. 27, 2012

Related U.S. Application Data

(63) Continuation-in-part of application No. PCT/US2010/046588, filed on Aug. 25, 2010.

(60) Provisional application No. 61/236,561, filed on Aug. 25, 2009.

(51) Int. Cl.
| C07H 21/02 | (2006.01) |
| A61K 48/00 | (2006.01) |
| C12N 15/00 | (2006.01) |
| A61K 38/54 | (2006.01) |
| C07K 14/47 | (2006.01) |
| C12N 9/22 | (2006.01) |

(52) U.S. Cl.
CPC ............ *C07K 14/4747* (2013.01); *A61K 48/005* (2013.01); *C12N 9/22* (2013.01)

(58) Field of Classification Search
None
See application file for complete search history.

(56) References Cited

U.S. PATENT DOCUMENTS

| 6,312,956 | B1 * | 11/2001 | Lane .............................. | 435/455 |
| 6,440,741 | B2 * | 8/2002 | Fisher et al. .................. | 435/455 |
| 6,987,127 | B2 * | 1/2006 | Kennedy ....................... | 514/457 |
| 7,090,976 | B2 * | 8/2006 | Anderson et al. ............ | 435/6.16 |
| 2004/0191843 | A1 * | 9/2004 | Wright et al. ................ | 435/7.23 |
| 2012/0328590 | A1 * | 12/2012 | Rosner ......................... | 424/94.3 |

OTHER PUBLICATIONS

Shiokawa (2001) "Characterization of Human DNase I Family Endonucleases and Activation of DNase [gamma] During Apoptosis" Biochemistry, 40(1): 143-52.*

Cuatrecaseas, et al. (1969) "Affinity Labeling of the Active Site of Staphylococcal Nuclease", The Journal of Biological Chemistry, 244: 4316-29.*

Uozumi, et al. (1976) "Purification and properties of the nuclease inhibitor of Aspergillus oryzae and kinetics of its interaction with crystalline nuclease O." The Journal of Biological Chemistry, 251: 2808-13.*

Romanova, et al. (1974) "L-Leucine, a natural inhibitor of silkworm larval nuclease", Insect Biochemistry, 4(4): 363-67 (Abstract Only).*

Lankat-Buttereit (2003) "Programmed cell death protein 4 (pdcd4): A novel target for antineoplastic therapy?", Biology of the Cell, 95: 515-19.*

Palamarchuk, et al. (2005) "Akt Phosphorylates and Regulates Pdcd4 Tumor Suppressor Protein", Cancer Research, 65(24): 11282-86.*

Parrish, et al. (2006) "Cuts can kill: the roles of apoptotic nucleases in cell death and animal development", Chromosoma, 115: 89-97.* http://www.biocenter.helsinki.fi/bi/vartiainen/ by Vartiainen, 2008, no journal, volume, number, 3 pages.*

Shak, et al. (1990) "Recombinant human DNase I reduces the viscosity of cystic fibrosis sputum", Proceedings of the National Academy of Sciences, USA., 87: 9188-92.*

Napirei, et al. (2005) "comparative characterization of rat deoxyribonuclease 1 (Dnase 1) and murine deoxyribonuclease 1-like 3 (Dnase1l3)", Biochemical Journal, 389: 355-64.*

Cookson, et al. (1999) "Poly(ADP-ribose) polymerase is found in both the nucleus and cytoplasm of human CNS", Brain Research, 834: 182-85.*

* cited by examiner

*Primary Examiner* — Robert M Kelly
(74) *Attorney, Agent, or Firm* — Kohn & Associates PLLC

(57) ABSTRACT

A gene construct comprising a programmed-cell-death executioner gene having a nuclear localization signal, a deleted signal peptide, an inhibitor-resistant binding site, a promoter, and an activator. A method of making a gene construct, by modifying a programmed-cell-death executioner gene by adding a nuclear localization signal, deleting a signal peptide, mutating a binding site for an inhibitor to make it inhibitor-resistant, adding a promoter for exclusive expression in selected cells, and adding an activator. A method of eliminating undesired cells from a patient. A method of treating cancer. An array comprising at least two gene constructs wherein all of the gene constructs differ with respect to the programmed-cell-death executioner gene and the nuclear localization signal. A method of personalizing anti-cancer treatment. A method of increasing DNase 1 resistance to actin binding. A method of increasing catalytic activity of DNase 1 binding.

10 Claims, 33 Drawing Sheets
(28 of 33 Drawing Sheet(s) Filed in Color)

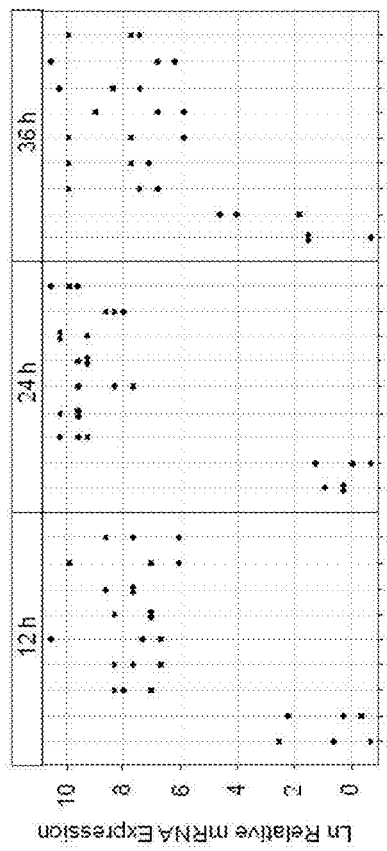
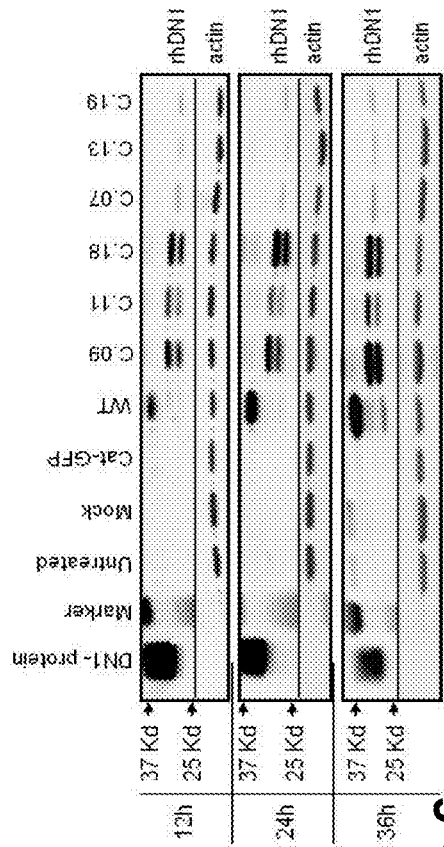

Figure 6

*Assessment of DNase1 Gene Construct Expression at the Molecular Level by Quantitative Real Time Reverse Transcription PCR (QRT-PCR) and Western Blotting.* All the tested DNase1 gene constructs were transcribed to mRNA (A) and translated to proteins (B), at all the tested time points; 12 h, 24 h, and 36 h post-transfection of Mel-Juso human melanoma cells. SP – Signal peptide; NLS – Nuclear Localization Signal; Cat-G – Cat-GFP; GFP – Green fluorescence protein; WT – Wild type DNase1; DN1 – DNase1.

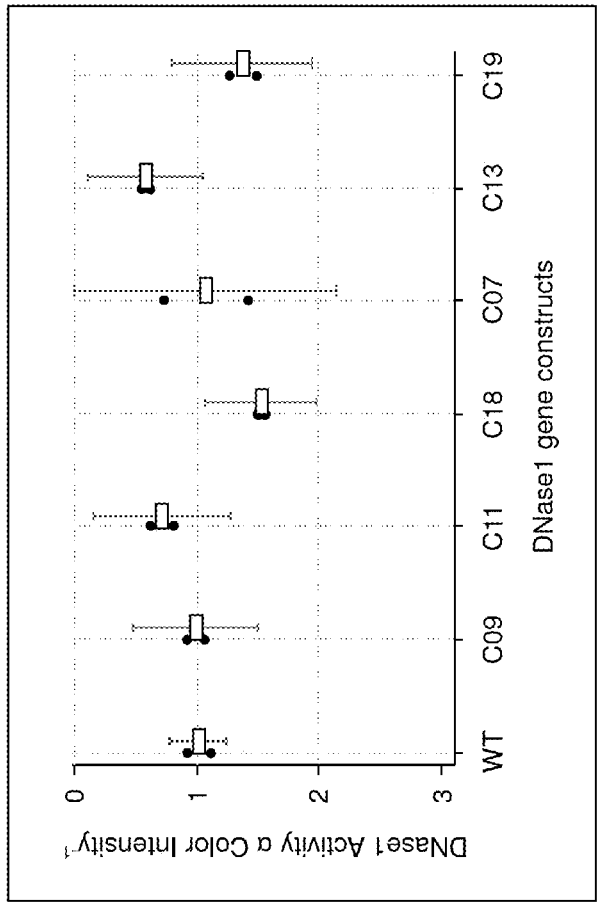

The intensity of the color developed during the enzymatic reaction reflects the amount of remaining intact DNA substrate and is inversely correlated to the DNase1 activity. The DNA-degradation activities of the Actin-resistant DNase1 gene constructs decreased after knocking down their activity site (H252A); C18 and C19 activity decreased as compared to C11 and C13, p = 0.0005 and p = 0.001, respectively. No difference in DNA degradation activity was observed between C11 and C13. Values are presented relative to Wild-type DNase1. Open rectangles represent means and lines represent 95% confidence intervals. WT – Wild type DNase1.

Figure 7

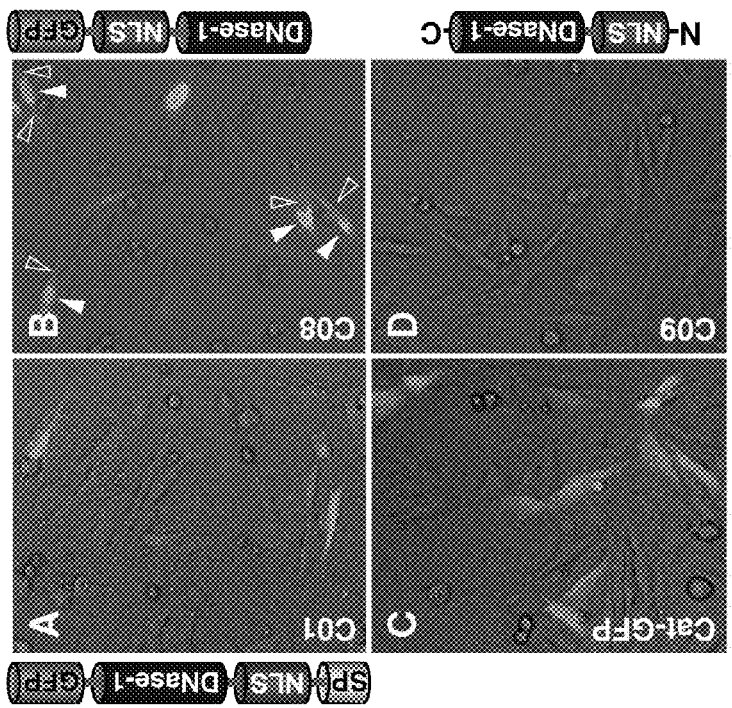

Figure 8 Representative samples of localization study of DNase1 protein constructs in Mel-Juso human melanoma cells 24 h after transfection. (A) Addition of a NLS to the GFP tagged DNase1 (C01) did not change the characteristic cytoplamic distribution of the secretory protein. (B) Elimination of the Signal peptide enabled targetting the NLS-fused DNase1 to the nucleus. (C, D) Controls. Closed arrow heads point to nuclear distribution; Open arrow heads point to scarse or absent cytoplasmic distribution. SP – Signal peptide; NLS – Nuclear Localization Signal; GFP – Green fluorescence protein ; Original magnification x 400.

Demonstration of Cytotoxicity of DNase1 Constructs in Melanoma Cells by a Colony Forming Assay (CFA)

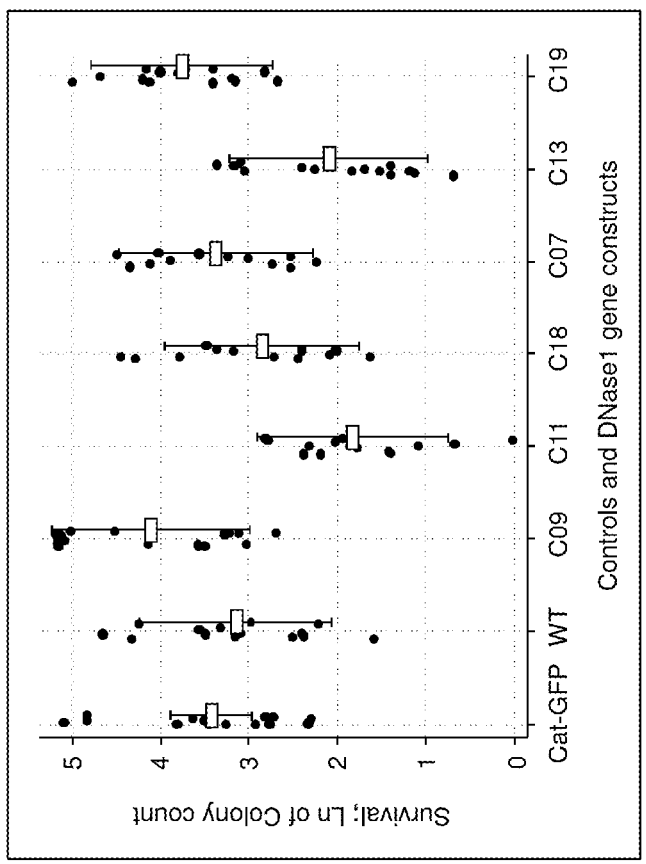

Survival of Mel-Juso human melanoma cells 14 days after treatment with DNase1 gene constructs as described in "Materials and Methods." The actin-resistant DNase1 gene constructs (C11 and C13) decreased melanoma cell survival significantly compared to the non-actin-resistant DNase1 gene constructs (C09 and C07; $p = 0.0002$ and $p = 0.0006$, respectively) and the wild type DNase1 ($p < 0.0001$). C11 DNase1 gene construct induced apoptosis in up to 20% of the cells. Values represent natural logarithm (Ln) of colony count (> 30 cells) in five experiments done in triplicates. Open rectangles represent means and lines represent 95% confidence intervals; $n = 15$. WT – Wild type DNase1.

Figure 9

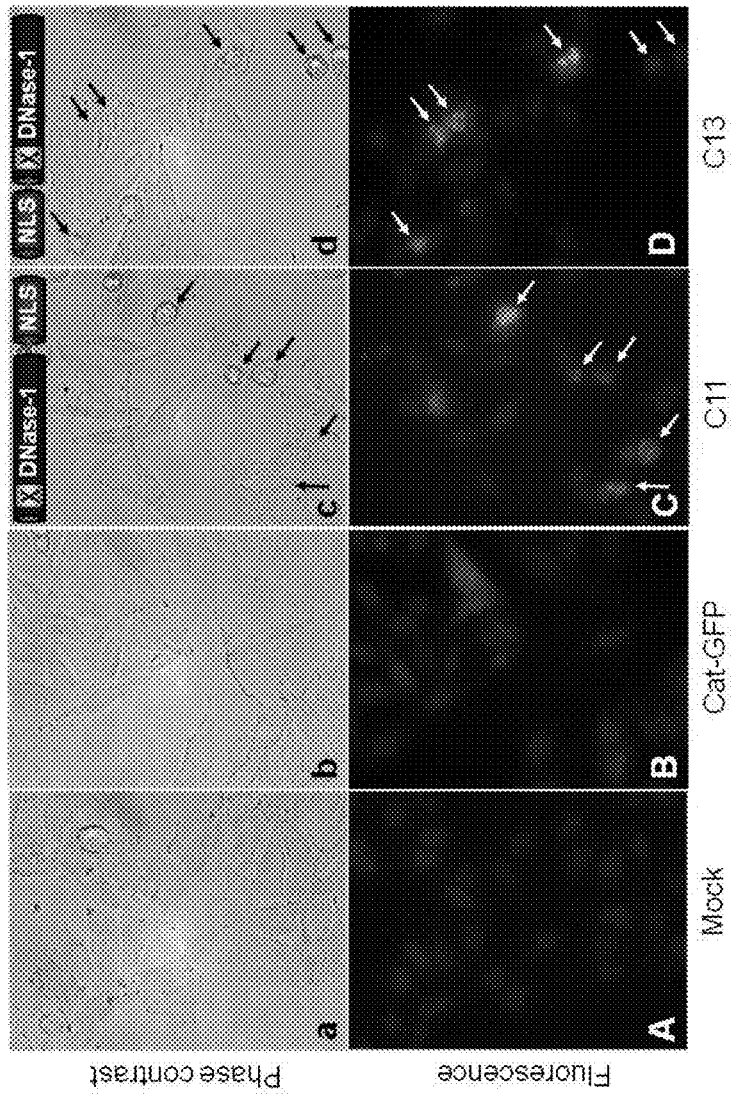

Figure 10 Morphological and Fluorescence Assessment of Cells Undergoing Apoptosis by Fluorescence and Phase Contrast Microscopy TUNEL assay assessment 24 h after transfection with various DNase1 constructs and controls. A substantial number of TUNEL positive cells (bright green fluorescence) is observed only after treatment with actin-resistant DNase1 gene constructs, C11 and C13 (C and D). Additional apoptotic morphology features include cell membrane blebbing, cytoplasm and nuclear condensation and characteristic apoptotic bodies (C, D, c and d). Cells undergoing apoptosis are seen in 'controls' only sporadically (A, B, a and b). Cell nuclei are counterstained blue with Hoechst 33258. Arrows indicate apoptotic cells; Original magnification x 400.

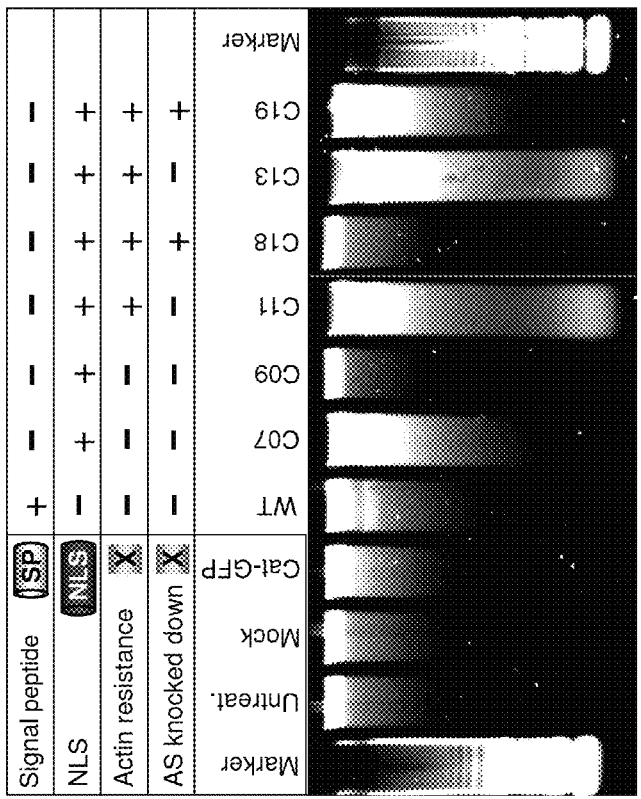

Figure 11

Apoptosis was induced in Mel-Juso human melanoma cells 24 h after plating by treatment with DNase1 gene constructs. Twenty-four hours post-transfection, DNA fragmentation was analyzed on an 1% agarose gel supplemented with Syto60 DNA binding dye and visualized with the Odyssey system. DNA fragmentation was most extensive after treating the melanoma cells with the actin-resistant DNase1 gene constructs C11 and C13. SP – Signal peptide; NLS – Nuclear Localization Signal; AS – Activity site; Mark. - 200 bp Marker; Untreat. – Untreated cells; WT – Wild type DNase1.

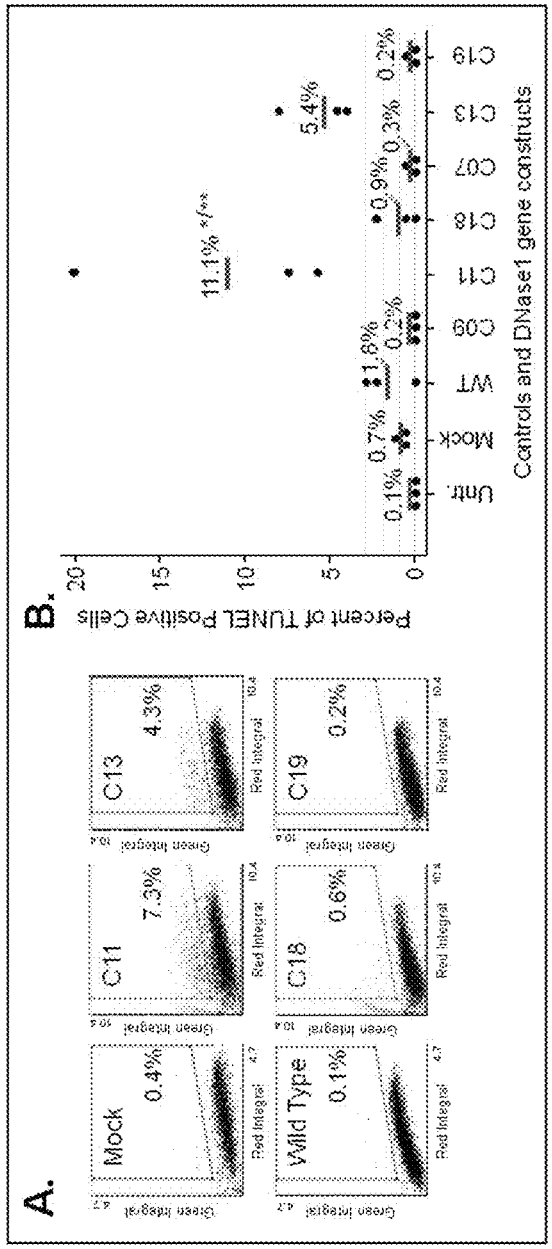

Quantitative analysis of human melanoma cells (Mel-Juso) undergoing apoptosis 24 h after transfection with various DNase1 gene constructs by LSC analysis of fluorescein-TUNEL (green) and propidium iodide (red) as described in "Materials and Methods." (A) Representative LSC-generated scattergraph shows increased proportion of cell population undergoing apoptosis (high green fluorescence intensity) after treatment with NLS+Actin-resistant DNase1 (C11), as compared to treatment with activity knocked down DNase1 (C18), Wild-type DNase1 or Mock. (B) Percent of TUNEL positive (apoptotic) cells were quantified by LSC. C11 DNase1 gene construct induced apoptosis in up to 20% of the cells. Means are represented by red bars and numerical values. The S.E.M. for C11, C13, Wild Type and C18 were 4.6%, 1.2%, 0.8% and 0.6%, respectively, and for all other samples ≤ 0.3%. *p = 0.004 with respect to Mock; **p = 0.02 with respect to Wild-type (n = 3). Untr. – Untreated cells; WT – Wild-type DNase1.

Figure 12

*Part of* MATERIAL & METHODS

DNase1 Gene Constructs – Design & Generation

Index

| | Page |
|---|---|
| Title & Index | p01 |
| DNase1 Gene Constructs ID | p02 |
| DNase1 Gene Constructs Design | p03 |
| DNase1 Gene Constructs Mutagenesis Primer Usage | p05 |
| DN1 transfer from pDONR223 to pDEST-47 (C.14) | p07 |
| From C.14, generate C.01, C.03, C04 | p08 |
| From C.14, generate C.01, C.03, C04, and from C.03 generate C.20 | p09 |
| From C.01, generate C.02, C.06 | p10 |
| From C.06, generate C.07, C12 | p11 |
| From C.07, generate C.13, and from C.13 generate C19 | p12 |
| From C.04, generate C.05 and C.08 | p13 |
| From C.08, generate C.09, C.10, C21p | p14 |
| From C.21p, generate C.22-21p, C.23-21p, C.24-21p, C.25-21p | p15 |
| From C.09, generate C.11, and from C.11 generate C18 and C.26p | p16 |
| From C.26p, generate C.27-26p, C.28-26p, C.29-26p, C.30-26p | p17 |
| From C.09, generate C.31-09p, C.32-09p, C.33-09p, C.34-09p, C.35-09p | p18 |
| From C.14, generate C.01 | p19 |
| Table 2, Sequences of primers for C.01 to C.19 | p20 |
| Table 3, Sequences of primers for C.20 to C.35 | p21 |

Figure 13

DNase1 Gene Constructs ID p02
Karli Rosner, M.D., Ph.D.

C.27-26p
C.28-26p
C.29-26p
C.30-26p

C.13
C.14
C.18
C.19

C.20p
C.21p
C.22-21p
C.23-21p
C.24-21p
C.25-21p
C.26p
C.31-09
C.32-09
C.33-09
C.34-09
C.35-09

C.01
C.02
C.03
C.04
C.05
C.06
C.07
C.08
C.09
C.10
C.11
C.12

Last review: 17/AUG/2009

Figure 14

Table 2. Primer sequences used to generate the DNase1 gene constructs

| Primer | SEQ ID NO: | Sequence |
|---|---|---|
| 114 | SEQ ID NO: 7 | 5'-cgacaccttcaaccgagagccaTTcattgtcaggttcttctcccgg-3' |
| 114-rc | SEQ ID NO: 8 | 5'-ccgggagaagaacctgacaatgAAtggctctcggttgaaggtgtcg-3' |
| ForPrimer252HtoA | SEQ ID NO: 9 | 5'-ggcccaagccatcagtgacGCAtatccagtggaggtgatgctgaagtgcccgccg-3' |
| P1-NLS-for | SEQ ID NO: 10 | 5'-actgggcggccctactcagggggcgtgtcccgcccgaaaaagaaacgcaaagtg-3' |
| P2-20p5-rc | SEQ ID NO: 11 | 5'-ggtctcccaaatgtctggatgttgaaggctcgatcttcagcatgccagcttttttgtaca-3' |
| P2-NLS-20p5-rc | SEQ ID NO: 12 | 5'-ggtctcccaaatgtctggatgttgaaggctcgatcttcagcacttgcgttctttc ggcggcatgccagcttttttgtaca-3' |
| P2-NLS-rc | SEQ ID NO: 13 | 5'-ggtctcccaaatgtctggatgttgaaggctgcgatctcagcacttgcgttctttttcggcgg-3' |
| P3-for-20p6 | SEQ ID NO: 14 | 5'-ccaagccatcagtgaccactacagtgaggtgatgctgaagtgctaatgaattaaaccgctga-3' |
| P3-NLS-for | SEQ ID NO: 15 | 5'-ccaagccatcagtgaccactacagtgaggtgatgctgaagtgcccgcgaaaaagaaacgcaaagtg-3' |
| P4-NLS-rc | SEQ ID NO: 16 | 5'-tcaacaagaattgggacaactccagtgaaaagttctctccttttgctagccatcactttgcgtttcttttcggcgg-3' |
| P5-for | SEQ ID NO: 17 | 5'-gacccaagctggctagttaagctgatcaaacaagtttgtacaaaaagctggcatg-3' |
| P6-NLS-rc | SEQ ID NO: 18 | 5'-ggcaactagaaggcacagtcgaggctgatcagcgggtttaattcattacacttttgctttctttttcgggcgg-3' |
| P6-rc | SEQ ID NO: 19 | 5'-ggcaactagaaggcacagtcgaggctgatcagcgggtttaattcatta-3' |
| RevPrimer252HtoA | SEQ ID NO: 20 | 5'-cggcggcacttcagcatcacctccactggataTGCgtcactgatgcttgggcc-3' |

Introduced mutations are shown in upper case and underlined.

Figure 32

Table 3. Primer sequences used to generate the DNase1 gene constructs

| Primer | Sequence |
| --- | --- |
| A114R-for | 5'-cgacaccttcaaccgagagccaCGGattgtcaggttcttcccgg-3' (SEQ ID NO: 21) |
| A114R-rc | 5'-ccgggagaagaacctgacaatCCGtggctctcggttgaaggtgtcg-3' (SEQ ID NO: 22) |
| D53A-for | 5'-tgactgccgtggggaagctgctggcgaacctcaatcaggatgcaccag-3' (SEQ ID NO: 23) |
| D53A-rc | 5'-ctggtgcatcctgattgaggttgccagcagcttcccacggcagtca-3' (SEQ ID NO: 24) |
| H44A-for | 5'-tggtccaggaggtcagagacagcgcactgactgcgtggggaagctgct-3' (SEQ ID NO: 25) |
| H44A-rc | 5'-agcagcttcccacacggcagtcagtgcgctgtctgacctcctggacca-3' (SEQ ID NO: 26) |
| NLS-1 | 5'-gatgctgaagtgcaagccccagcagcaacaaagaaggccggcaggcaagaagaagaagctt-3' (SEQ ID NO: 27) |
| NLS-1-rc | 5'-ttgctagccataagcttcttcttttgcctgccgcggccttcttgttgctgctgggcgctt-3' (SEQ ID NO: 28) |
| NLS-2 | 5'-gaagtgatgctgaagtgcgacgcaccgcgagcaaaaagcccgccaggg-3' (SEQ ID NO: 29) |
| NLS-2-rc | 5'-tccttgctagccatccctgcgcgcgggcttttgcctgcgcggtgcgtc-3' (SEQ ID NO: 30) |
| NLS-3 | 5'-ggtgatgctgaagtgccgaaagttaagaagaagtttaag-3' (SEQ ID NO: 31) |
| NLS-3-rc | 5'-ttctcctttgctagccatcttaaacttcg-3' (SEQ ID NO: 32) |
| NLS-4 | 5'-ggaggtgatgctgaagtgcagccgcaaacgaccgcggccc-3' (SEQ ID NO: 33) |
| NLS-4-rc | 5'-ttctcctttgctagccatgggccgcggtcgtttgcggct-3' (SEQ ID NO: 34) |
| NLS-a-rc | 5'-ttaattcattaagcttctctttgcctgccccgccttcttttgttgctgcgggcgctt-3' (SEQ ID NO: 35) |
| NLS-b-rc | 5'-ggggtttaattcattaccctgcgcgcgggcttttgcctgcgcggtgcgtc-3' (SEQ ID NO: 36) |
| NLS-c-rc | 5'-agcgggtttaattcattacttaaacttcttcttaaacttcg-3' (SEQ ID NO: 37) |
| NLS-d-rc | 5'-agcgggtttaattcattagggccgccgctttgcggct-3' (SEQ ID NO: 38) |
| P7-for-19p8 | 5'-ccaagccatcatcagtgaccactatccagtggaggtgatgctgaagtgcatggctagcaaggagaag-3' (SEQ ID NO: 39) |
| P8-rc | 5'-ccatctaattcaacaagaattggacaactccagtgaaaagttctccttttgctagccat-3' (SEQ ID NO: 40) |
| P9-for-19p6 | 5'-ccaagccatcagtgacgcatatccagtggaggtgatgctgaagtgctaatgaattaaacccgctg-3' (SEQ ID NO: 41) |
| V67M-for | 5'-gcaccagacacctatcactgtATGagtgagccactggacggaacagc-3' (SEQ ID NO: 42) |
| V67M-rc | 5'-gctgttccgtccagtggctcactCATcacgtagtagatggtctggtgc-3' (SEQ ID NO: 43) |
| Y65W-for | 5'-caggatgcaccagacacctactactgggtcagtgagccactggacg-3' (SEQ ID NO: 44) |
| Y65W-rc | 5'-ccgtccagtggctcactgacccaccagtagtaggtggtctggtgcatcctg-3' (SEQ ID NO: 45) |

Figure 33

ANTI-CANCER THERAPEUTIC STRATEGY TO OVERCOME CANCER RESISTANCE AND TO ENABLE TAILORING TREATMENT TO PATIENTS

BACKGROUND OF THE INVENTION

1. Field of the Invention

The present invention relates to therapeutics and methods of treating cancer. In particular, the present invention relates to modified programmed-cell-death executioner genes.

2. Description of the Prior Art

DNA-degrading enzymes are important mediators of aptoptosis. DNase 1, for example, is a powerful DNA-degrading enzyme, that preferentially cleaves DNA at phosphodiester linkages adjacent to a pyrimidine nucleotide, producing tetranucleotides, and also binds actin. DNase 1 acts on both single- and double-stranded DNA as well as chromatin. DNase 1 is the major extracellular DNase protein and a major executioner of intracellular apoptosis, i.e. cell death (Peitsch, et al., EMBO J. 1993, 12:371-7; 1993; Boone, et al., Biol Reprod 1997, 57:813-21). In its native form, DNase 1 cannot trigger intracellular apoptosis. Peitsch, et al. proposed that processes that initiate apoptosis allow the rapid access of endoplasmic reticulum enzymes to the nucleus, resulting in the apparent "activation" of DNase 1, and COS cells transfected with cDNA of rat parotid DNase 1 resulted in DNA fragmentation. The signal peptide, which diverts the protein away from the nucleus, was not removed. A nuclear localization signal was not included; therefore, DNase 1 did not localize to the nucleus. The actin binding site was not mutated, and therefore, the DNase 1 was not resistant to inhibition by actin.

Normal and cancerous cells protect themselves from premature death by the powerful DNA-digestive DNase 1 by four main mechanisms: (i) the nucleus of cells is enveloped by a nuclear membrane that is impenetrable to DNase 1; (ii) the DNase 1 protein is lacking a nuclear localization signal (NLS), which other DNases such as DNase γ have (Lechardeur, et al., J Cell Biol 2000, 150:321-4; Shiokawa, et al., Biochem J 2003, 376:377-81), and the NLS is needed to direct a protein after translation back into the nucleus; (iii) the DNase 1 protein is equipped with a signal peptide (SP), which directs it away from the nucleus, to the endoplasmic reticulum, where it is packaged in an endosome to contain its activity and to either be secreted from the cell or to reside in small amounts around the nucleus; and (iv) even if DNase 1 could leak into the nucleus, it would be inactivated by nuclear actin. Thus, DNase 1 could have access to the cell's DNA only after the activated apoptosis cascade led to initial disintegration of the nucleus membrane. Various combinations of these four mechanisms likely protect normal and cancerous cells from additional DNA-degrading enzymes to DNAse I.

Saito, et al. (J Neuro-Oncol 2003, 63:25-31) induced DNA fragmentation by transfecting human glioma cells with DNase γ. In the years since this publication, neither this group nor any other group has pursued therapeutic application for DNase γ. Progress was made only in showing histological evidence in rodent liver that DNase γ has a role in Fas-independent apoptotic DNA fragmentation (Higami, et al., Cell Tissue Res 2004, 316: 403-7), and in further biochemical characterization of DNase γ (Sunaga, et al., Bioorg Med. Chem. 2006, 14:4217-26; Mizuta, et al., Biochem Biophys Res Commun. 2006, 345:560-7). Caspase-activated DNase (CAD, DFF40) has been used by Ben-Yehuda, et al. (Clin Cancer Res 2003, 9:1179-90) in the form of a chimeric protein with Gonadotropin-releasing hormone (GnRH-DFF40) to induce apoptosis in a colon adeno-carcinoma cell line. In the years since that publication, this group did not disclose any further advances toward therapy with their approach. Progress was made only to show that the GnRH-based chimeric protein can be used as a tool for the detection of adeno-carcinoma (Lichtenstein, et al., Int J Oncol 2005, 27:143-8).

In 1993, Polzar, et al. (Eur J Cell Biol 1993, 62:397-405) demonstrated that overexpression of native DNase 1 caused apoptosis of COS-cells. In the same year, the same group (Petisch, et al., EMBO J. 1993, 12:371-7) reported that overexpression of DNase 1 alone cannot induce apoptosis because it has no access to the nucleus. Napirei, et al. (Biochem J 2005, 389: 355-64) also overexpressed native DNase 1 and observed neither apoptosis nor localization of DNase 1 in the nucleus. Rat DNase 1 and murine DNase 1l3 were compared, and neither contained an NLS, and the actin binding site was not mutated. Oliveri, et al. (Eur J Immunol 2001, 31:743-51) accelerated apoptosis 2-4 fold by adding chemotherapeutic drugs to cells, which stably overexpressed the DNase 1 gene. The signal peptide-DNase 1 by itself has not been shown to induce apoptosis. In Oliveri, et al., the signal peptide was not removed, an NLS was not included, and the actin binding site was not mutated, and therefore the DNase 1 did not localize to the nucleus and it was not actin resistant.

Napirei, et al. (Biochem J 2005, 389:355-64) deleted the signal peptide from DNase 1 and observed localization of DNase 1 in both the cytoplasm and nucleus, but no apoptosis.

Linardou, et al. (Int J Cancer, 2000, 86:561-9) created a scFv-DNase 1 chimera against human placental alkaline phosphatase (hPLAP) that decreased cell viability when measuring the level of DNA synthesis in a tritium-labeled thymidine (3H-TdR) incorporation assay. Bovine DNase 1 was used. The signal peptide was not removed, and an NLS was not included. The actin binding site was not mutated, and therefore, the chimera was not resistant to DNase 1 inhibition by actin. Apoptosis tests were not performed, only cytotoxicity was tested. The scFv-Ab seemed to be cytotoxic as well, suggesting necrosis in addition to possible apoptosis.

The actin binding site on DNase 1 has been inactivated to increase the potency of DNase 1 to dilute viscosity of upper respiratory secretions in Cystic Fibrosis (CF) patients (Ulmer, et al., PNAS 1996, 93:8225-9; Pan, et al., J Biol Chem 1998, 273:18374-81) and for treatment of systemic lupus erythematosus (Pan, et al., J Biol Chem 1998, 273:18374-81). Recombinant human DNase 1 (PULMOZYME®, Genentech) was approved by the FDA in December 1998 as an aerosolized mucolytic agent for the management of patients with CF. This shows that DNase 1 is safe to administer to humans. Ulmer, et al. showed that the binding site for actin was mutated and increased DNAse 1's ability to digest DNA in sputum, thus, reducing its viscosity. The DNase 1 was not aimed at functioning inside cells or inducing apoptosis in cells. The signal peptide, which diverts the protein away from the nucleus, was not removed, and an NLS was not included.

None of the above described modifications of DNase 1 have been shown to be successful in treating cancer. There remains a need for a method of using DNases, and especially DNase 1, as therapeutics for cancer.

Malignant melanoma is the most aggressive form of cancer. Its dimensions are reported in millimeters. Tumor thickness approaching 4 mm presents a high risk of metastasis. A diagnosis of metastatic melanoma carries with it a median survival of 6-9 months. At the time of diagnosis, 20% of patients have metastasis; 16% to the lymph nodes and 4% to the distal organs. Current methods of treatment include surgical resection, radiation, chemotherapy with dacarbazine, tamoxifen, or temozolamide, or immunotherapeutics such as IL-2, IFN-α. Only a minority of patients respond to these methods of treatment. There is a general lack of efficacy and a high rate of severe side effects experienced by those patients using non-surgical treatments. The trend of therapeutics is going away from broad-spectrum cytotoxic chemotherapy and towards specific molecularly targeted therapies. Therefore, more effective treatments are needed for malignant melanoma.

Some of the therapeutics that have been developed as specific molecularly targeted therapies include immunotherapies such as vaccines (e.g. Hi-8™ MEL-vaccine (Oxxon Therapeutics)) and ONCOVEX® (BioVex, Inc.), as well as biotherapeutics that perform functions such as targeting anti-apoptosis/resistance (e.g. Bcl2, IAP, NF-KB inhibition), promoting apoptosis (e.g. TRAIL ligands), siRNA (e.g. against Mitf), and suicide gene-therapy (e.g. HSV-tk).

Gene therapy, i.e. the transfer of genetic material into living cells for treatment or prevention of disease, has grown in popularity for use as a treatment over the years. The United States conducts the most gene therapy clinical trials, with some conducted in Europe and Asia. The United States also leads the rest of the world in the study of malignant melanoma with gene therapy clinical trials.

Gene therapy targeted to melanoma cells involves the introduction of "suicide" genes, such as a herpes simplex virus thymidine kinase gene (HSVtk), the transfer of tumor suppressor genes such as p53 gene or p16INK4a, the inactivation of oncogenic signaling pathways such as ras, c-myc, and signal transducers and activators of transcription-3 (Stat3), and the introduction of genes encoding immunologically relevant molecules such as allogenic MHC class I genes, cytokine genes (GM-CSF, IL-2, IFNs), and co-stimulatory molecules (B7.1). Gene therapy can also be targeted to the host's immune cells. T cells are targeted with the introduction of neomycin phosphotransferase gene and chimeric receptor (IL-2R/GM-CSFR). Dendritic cells are targeted with genes encoding melanoma antigens (MART-1/Melan A) and CD40 ligand.

Several clinical trials involving gene therapy are currently being conducted. GLYBERA® (alipogene tiparvovec, Amsterdam Molecular Therapeutics) is an AAV-1 vector encoding lipoprotein lipase for treatment of patients with lipoprotein lipase deficiency. INGN-241 (Introgen) is an E1-deleted, replication-incompetent adenoviral vector encoding melanoma-differentiation-associated gene-7 (mda-7; interleukin-24) for treatment of metastatic melanoma. TNFerade (GenVec) is an E1-, E3-, and E4-deleted andenoviral vector encoding human TNF-α under the control of the radiation-inducible early growth response promoter for use in pancreatic cancer. A retrovirus by MolMed encoding herpes simplex virus thymidine kinase transduced ex vivo into hematopoietic stem cells is used for graft-versus-host disease. ALLOVECTIN-7® velimogene aliplasmid, Vical) is a DNA plasmid encoding the human leukocyte antigen-B7 (HLA-B7) and β2-microglobulin complex in the context of cationic lipid mixture (DMRIE/DOPE) for use in chemotherapy-naïve patients with metastatic melanoma. PROSAVIN® (Oxford Biomedica) is combined lentivirus and equine infectious anemia virus vectors encoding aromatic amino acid decarboxylase, tyrosine hyroxylase and GTP-cyclohydrolase-1 used for Parkinson's disease. tgAAC-94 (Targeted Genetics) is an AAV-2 encoding IgG1Fc and the TNF-α receptor used in rheumatoid arthritis.

There are also several current gene therapies in clinical trials directed at targeting apoptosis in cancer. Anti-TRAILR1 agonistic antibody (Human Genome Sciences/Cambridge Antibody Technology/Takeda), Anti-TRAILR2 agonistic antibody (Human Genome Sciences/Cambridge Antibody Technology), and TRAIL (Genentech/Amgen) are used for solid tumors. GENASENSE® (oblimersen, anti-sense oligonucleotide targeting BCL2, Genta, Inc.) was used in malignant melanoma, multiple myeloma, and chronic lymphocytic leukemia (CLL). SPC-2996 (antisense oligonucleotide targeting BCL2, Santaris Pharma), AT 101 ((−)-Gossypol, Ascenta Therapeutics Inc.), and small molecule BCL2-family inhibitor (Gemin X Biotech) are used for CLL. Other apoptosis-inducing agents include ABT-737 (small molecule BCL2-family inhibitor, Abbott Laboratories/Idun Pharmaceuticals), IPI-983L/IPI-194 (small molecule BCL2-family inhibitors, Infinity Pharmaceuticals), XIAP-BIR2 inhibitor (Burnham Institute), XIAP-BIR3 inhibitor (UT Southwestern), XIAP-BIR3 inhibitor (Abbott Laboratories), and Nutlins (MDM2 inhibitors, Wyeth).

Several gene therapies have been developed to specifically target apoptosis in melanoma by sensitizing melanoma cells to TRAIL-mediated apoptosis. Some agents upregulate TRAIL receptors to cause DNA damage and upregulation of apoptosis through p53 (cisplatin/doxorubicin, betulinic acid, CD347 retinoid, TNF-α). Other agents potentiate the mitochondrial pathway and decrease BCL2, BCL-XL, and MCL-1 (Antisense to BCL2, BCL-XL, and MCL-1), downregulate BCL2, BCL-XL, and MCL-1 (MEK1 inhibitors, PD98059), damage mitochondria (cisplatin/doxorubicin), and increase apoptosis activating factor (APAF) levels by inhibiting methylation (5-aza-deoxycytidine). Agents inhibit NF-κB activation by proteasome inhibition and upregulation of IκBα (PS341), and competing with p53 for co-transcriptional factors (temozolomide and vinblastine). Also, agents downregulate inhibitor of apoptosis protein (IAP) levels by decreasing XIAP levels (actinomycin-D, fludarabine, second mitochondria-derived activator of caspase (SMAC)/DI-ABLO constructs).

Apoptosis is a physiological mechanism of programmed cell death by which unwanted cells are eliminated from tissues in response to specific stimuli. The apoptosis cascade is shown in FIG. 1. The current failure of the above described gene therapy treatments results from the fact that the majority of cancers protect themselves by inactivating or underexpressing death receptors, not expressing or inactivating intermediate components of the apoptosis cascade, and overexpressing anti-apoptotic proteins that inactivate pro-apoptotic components along the apoptosis cascade as shown in FIG. 2. Therefore, a method of treatment is needed that overcomes the difficulties presented by the natural protection mechanisms of cancer cells against the apoptosis cascade.

SUMMARY OF THE INVENTION

The present invention provides for a gene construct, including a programmed-cell-death executioner gene having a nuclear localization signal, a deleted signal peptide, an inhibitor-resistant binding site, a promoter, and an activator. The gene construct is a late player in the cell death process that has the ability to initiate programmed cell death and execute it with increased efficiency.

The present invention provides for a method of making the gene construct by modifying a nuclease encoding gene, which in its native form and under physiological conditions is incapable of triggering cell death by adding a nuclear localization signal, deleting a signal peptide, mutating a binding site for an inhibitor to make it resistant to that inhibitor, adding a promoter for exclusive expression in selected cells, and adding an activator.

The present invention also provides for a method of eliminating undesired cells from a patient, including the steps of administering a therapeutic containing a gene construct, delivering the therapeutic to undesired cells, activating apoptosis of the undesired cells without triggering the apoptosis cascade, and destroying the undesired cells.

The present invention provides for a method of treating cancer, including the step of activating apoptosis of cancer cells without the need for triggering the apoptosis cascade.

The present invention provides for an array that is generated of at least two gene constructs described above, with all of the constructs differing with respect to the programmed-cell-death executioner gene and with respect to the nuclear localization signal.

The present invention also provides for a method of personalizing anti-cancer treatment by taking a sample of cancerous cells from a patient, applying the cells to an array of at least two gene constructs with all of the constructs differing with respect to the programmed-cell-death executioner gene, with respect to the promoter and with respect to the nuclear localization signal, selecting the gene construct with the highest sensitivity to the cancerous cells, and treating the patient with the selected gene construct.

The present invention further provides for using the array as a diagnostic device to determine if a patient has cancer by taking a sample of cells in a patient, determining if a gene construct in the array is sensitive to the cells, and if cells are sensitive to at least one gene construct, determining that the patient has cancer.

The present invention also provides for a method of increasing DNase 1 resistance to actin binding by mutating native amino acids at an actin binding site chosen from the group consisting of Glu-13, His-44, Asp-53, Tyr-65, Val-66, Val-67, Glu-69, Ala-114, and combinations thereof.

The present invention provides for a method of increasing catalytic activity of DNase 1 by mutating native amino acids to change the electrical charge chosen from the group consisting of Gln-9, Glu-13, Asn-74, and combinations thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other advantages of the present invention will be readily appreciated as the same becomes better understood by reference to the following detailed description when considered in connection with the accompanying drawings wherein:

FIGS. 6A and 6B are assessments of DNase 1 gene construct expression at the molecular level by Quantitative Real Time Reverse Transcription PCR (QRT-PCR) and Western Blotting with mRNA (6A) and protein (6B) (SP—Signal peptide; NLS—Nuclear Localization Signal; Cat-G—Cat-GFP; GFP—Green fluorescence protein; WT—Wild type DNase 1; DN1—DNase 1);

FIG. 7 is a graph of in vitro assessment of DNase 1 activity by a colorimetric assay, values are presented relative to Wild-type DNase 1, open rectangles represent means and lines represent 95% confidence intervals. WT—Wild type DNase 1;

FIGS. 8A-8D are photographs of representative samples of localization study of DNase 1 protein constructs in Mel-Juso human melanoma cells 24 hours after transfection, FIG. 8A shows that addition of a NLS to the GFP tagged DNase 1 (C01) did not change the characteristic cytoplasmic distribution of the secretory protein, FIG. 8B shows elimination of the Signal peptide enabled targeting the NLS-fused DNase 1 to the nucleus, FIGS. 8C and 8D are controls, closed arrow heads point to nuclear distribution, open arrow heads point to scarce or absent cytoplasmic distribution (SP—Signal peptide, NLS—Nuclear Localization Signal, GFP—Green fluorescence protein; Original magnification ×400);

FIG. 9 is a graph showing the cytotoxicity of DNase 1 constructs in melanoma cells by a Colony Forming Assay (CFA), values represent natural logarithm (Ln) of colony count (>30 cells) in five experiments done in triplicates, open rectangles represent means and lines represent 95% confidence intervals; n=15 (WT—Wild type DNase 1);

FIGS. 10A-10D are fluorescence and phase contrast microscopy photographs of Mel-Juso human melanoma cells using TUNEL assay; DNase 1 gene constructs C11 (10C) and C13 (10D) as well as controls (10A and 10B), arrows indicate apoptotic cells; Original magnification ×400;

FIG. 11 is a photograph of a DNA fragmentation assay (SP—Signal peptide; NLS—Nuclear Localization Signal; AS—Activity site; Mark.—200 bp Marker; Untreat.—Untreated cells; WT—Wild type DNase 1);

FIG. 12A shows a representative LSC-generated scattergraph with increased proportion of cell population undergoing apoptosis (high green fluorescence intensity) after treatment with NLS+Actin-resistant DNase 1 (C11), as compared to treatment with activity knocked down DNase 1 (C18), Wild-type DNase 1 or Mock, and FIG. 12B is a graph showing percent of TUNEL positive (apoptotic) cells quantified by LSC, wherein means are represented by bars and numerical values, the S.E.M. for C11, C13, Wild Type and C18 were 4.6%, 1.2%, 0.8% and 0.6%, respectively, and for all other samples ≤0.3%. *p=0.004 with respect to Mock; **p=0.02 with respect to Wild-type (n=3) (Untr.—Untreated cells; WT—Wild-type DNase 1);

FIG. 13 is an index of DNase 1 gene constructs design and generation;

FIG. 14 is a list of identification of the DNase 1 gene constructs;

FIG. 32 is a table showing sequences of primers;
and
FIG. 33 is a table showing sequences of primers.

DETAILED DESCRIPTION OF THE INVENTION

The present invention provides a treatment for cancer and various chronic and infectious diseases, based on modified programmed-cell-death executioner genes. A programmed-cell-death executioner protein is a DNA-degrading enzyme. Essentially, the modified programmed-cell-death executioner gene is a core enzyme that lacks a nuclear localization signal and has the ability to degrade DNA. Preferably, a modified DNA-degrading enzyme, most preferably a modified human recombinant (hr) deoxyribonuclease-1 (hr DNase 1) gene is used. However, other modified programmed-cell-death executioner genes can be used, such as, but not limited to, DNase 1L1, DNase 1L2 (DHP1), DNase 1L3 (DNase γ; DHP2), DNase 2A, DNase 2B, Caspase-activated DNase (CAD), Endonuclease G (ENDOG), Granzyme B (GZMB), and DNase X. The present invention provides both for a method of making the gene constructs as well as methods of use thereof.

"Gene construct" as used herein, refers to the programmed-cell-death executioner gene as modified by the method of the present invention, and each term can be used interchangeably herein.

Figure 1:
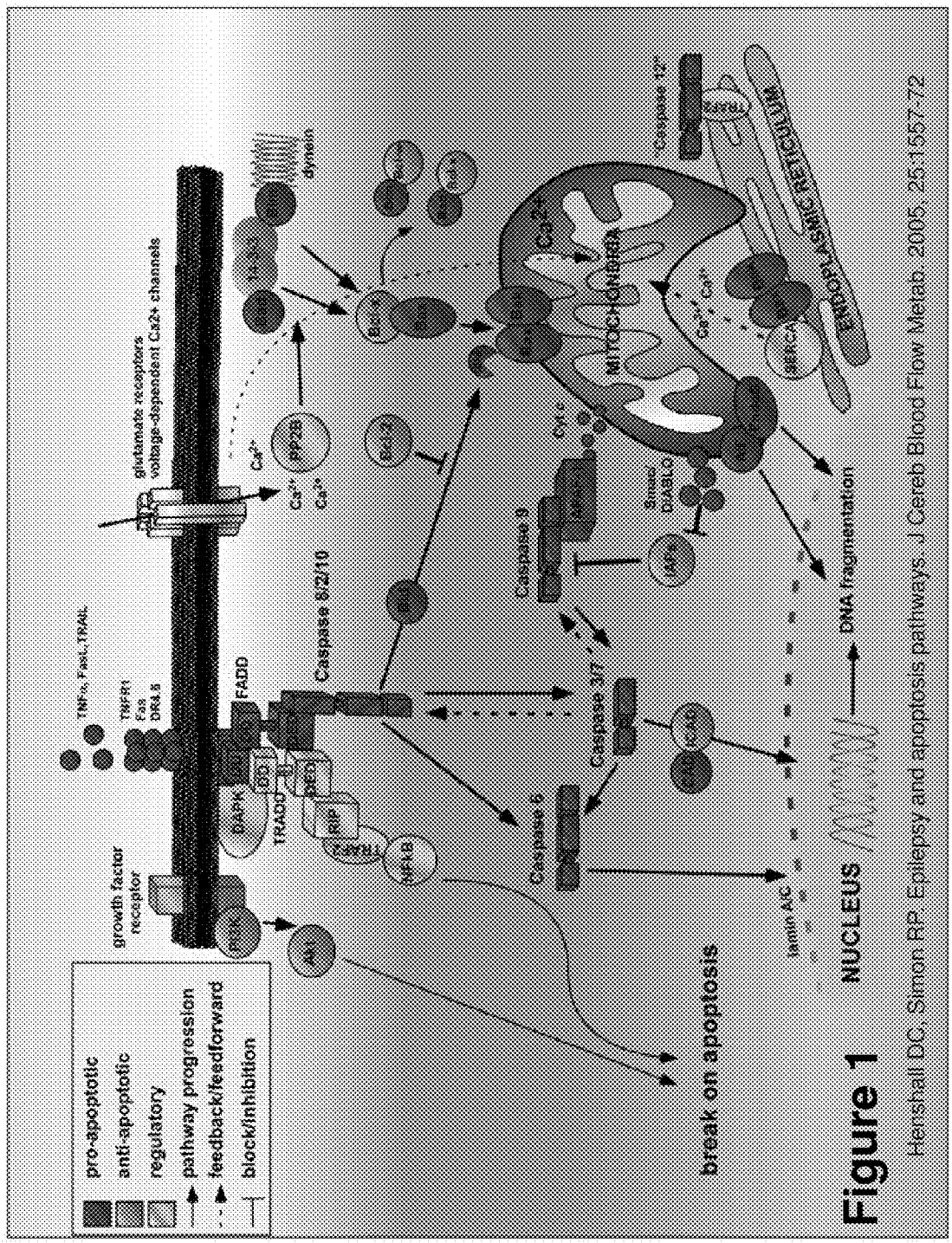
FIG. 1 is a diagram of the apoptosis cascade.
Figure 2:
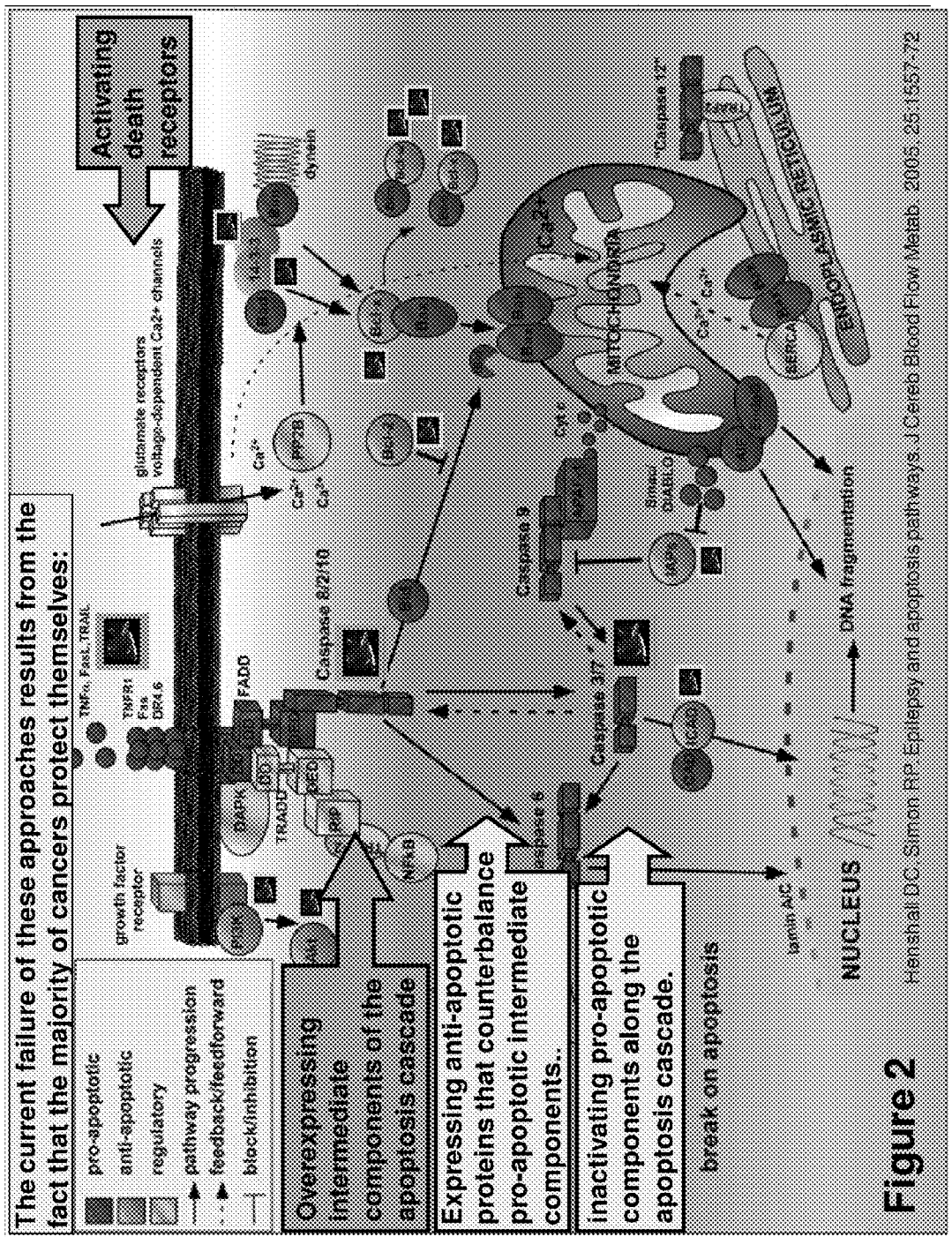
FIG. 2 is a diagram of how cancer cells protect themselves from the apoptosis cascade.
Figure 3:
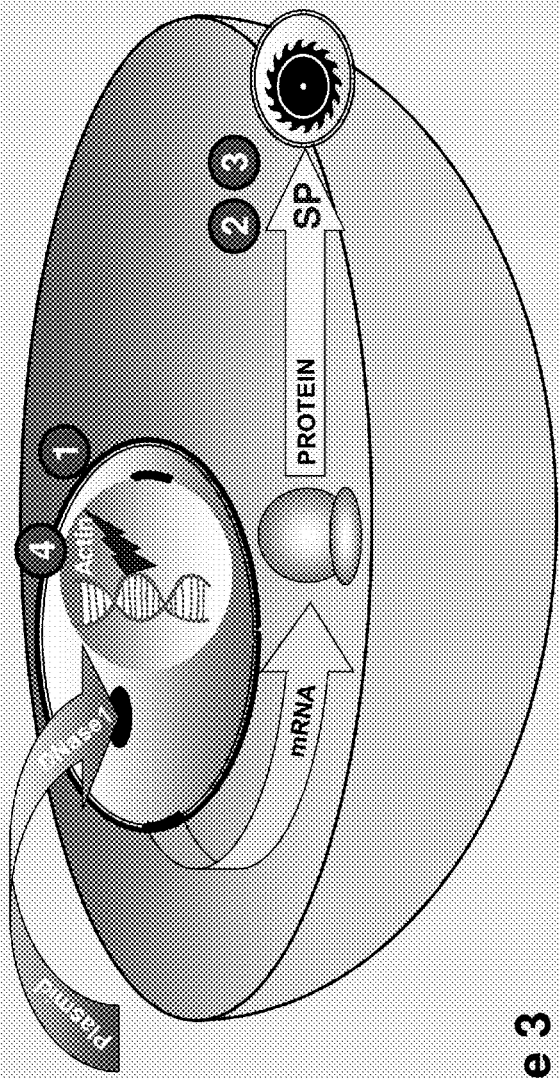
FIG. 3 is a diagram of how DNase 1 is prevented from activating in a cell.
Figure 4:
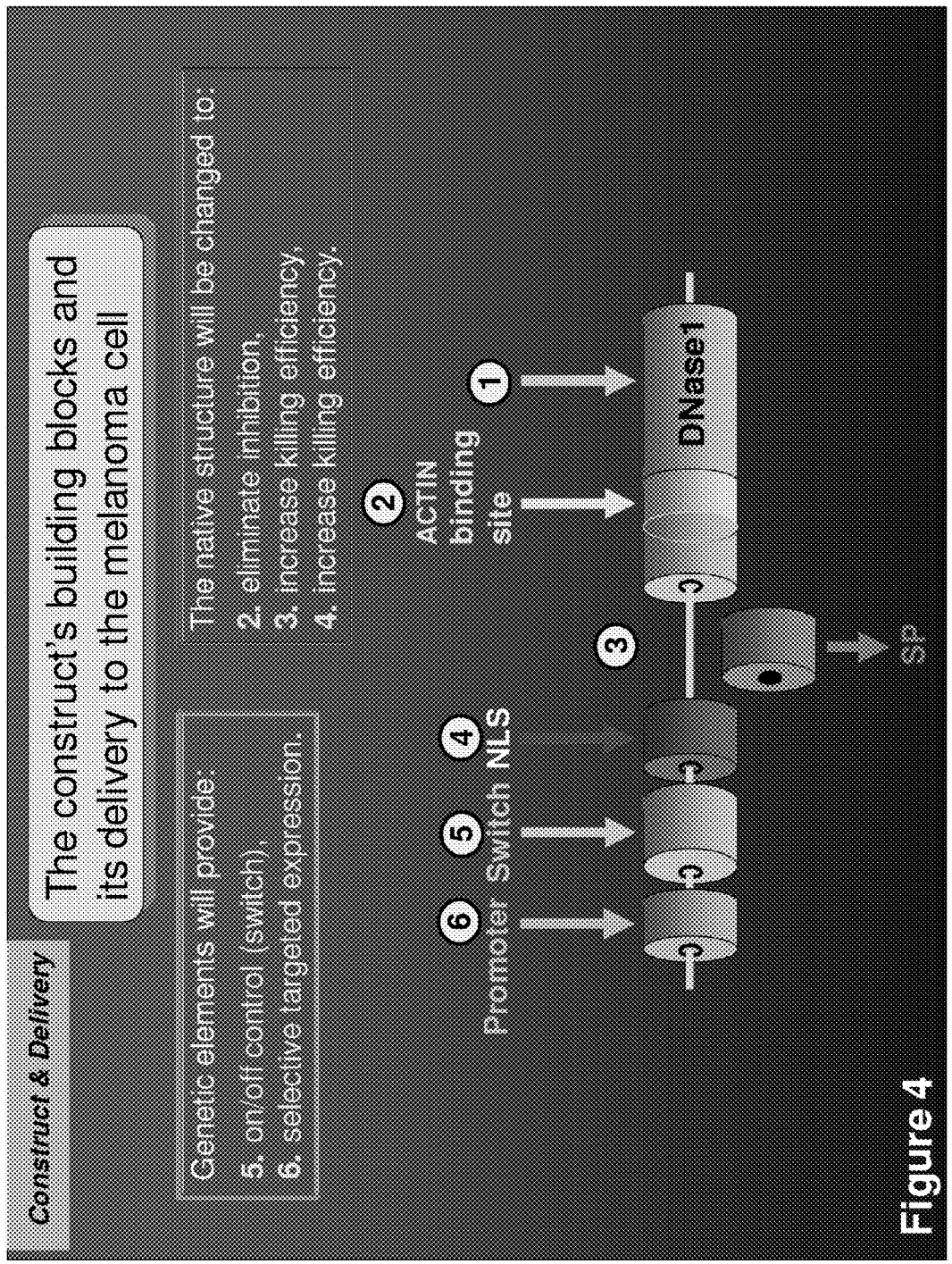
FIG. 4 is a diagram of the building blocks of a gene construct of the present invention.

The gene constructs of the present invention are made by performing the following modifications on a programmed-cell-death executioner gene such as a gene for a DNA-degrading enzyme, generally shown in FIG. 4 for the specific example of DNase 1. Each of these modifications serve to prevent premature activation of cell death by the programmed-cell-death executioner gene by several mechanisms. These mechanisms include the barrier function of the nuclear membrane, the presence of a signal peptide that diverts the programmed-cell-death executioner gene from the nucleus, the absence of a nuclear localization signal, and the presence of an inhibitor, actin, in the nucleus, endoplasmic reticulum, and cytoplasm, as shown in FIG. 3.

Figure 31:
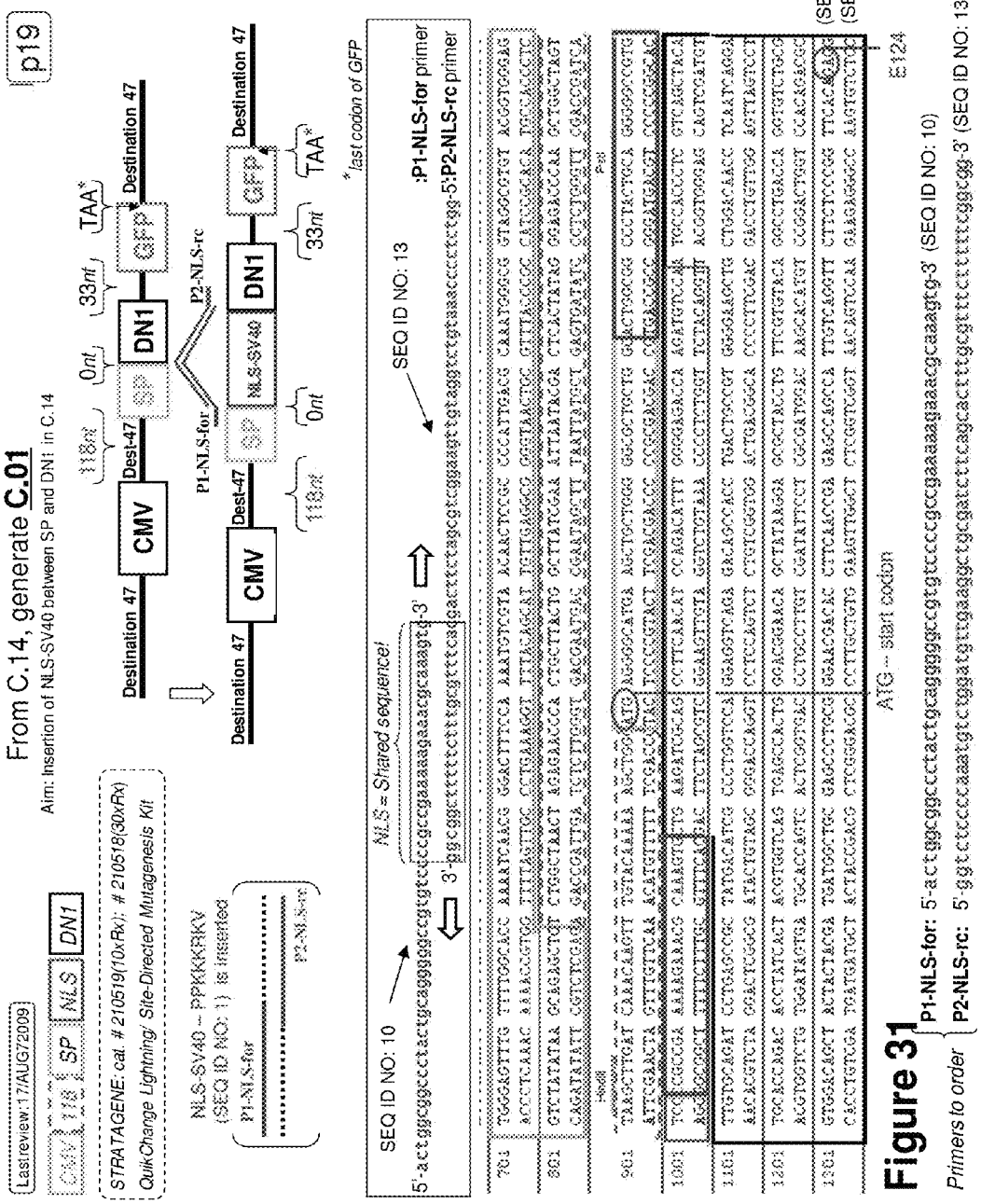
FIG. 31 is a flow chart showing from C.14 generation of C.01.

The programmed-cell-death executioner gene is first modified by equipping it with a (5'-/-3') nuclear localization signal (NLS) to render access of the gene to the nucleus. This increases killing efficiency of the gene construct. The following NLS's are described in the Example. PPKKKRKV (SEQ ID NO: 1) (NLS-SV40, see FIG. 31), is employed in C01, C02, C04, C05, C08, C09, C10, C11, C12, C13, C18 and C19. KRPAATKKAGQAKKKKL (SEQ ID NO: 2) (see NLS-1KR in FIG. 27 and primers in FIG. 33) is employed in C27-26p. NAPRGKKPAPG (SEQ ID NO: 3) (see NLS-2NA in FIG. 27 and primers in FIG. 33) is employed in C28-26p. RKFKKKFNK (SEQ ID NO: 4) (see NLS-3RK in FIG. 27 and primers in FIG. 33) is employed in C29-26p. SRKRPRP (SEQ ID NO: 5) (see NLS-4SR in FIG. 27 and primers in FIG. 33) is employed in C30-26p. Any other suitable NLS can be used and can be added by one skilled in the art.

The signal peptide is deleted to prevent loss of the gene construct by diversion to the endoplasmic reticulum. This increases killing efficiency of the gene construct.

The binding site for actin (the inhibitor) is mutated or deleted to make the gene construct actin-resistant, thus enabling the gene construct to digest a cell's DNA. This eliminates inhibition.

A promoter is added and secures exclusive expression of the killer gene in selected cell types, such as malignant melanoma cells. The cell types can be cancerous or otherwise undesired cells. The method of the addition is explained further below in the Example (Materials and Methods). This provides selective targeted expression. The promoter can include a melanocyte-specific promoter such as tyrosinase, melanoma inhibitory activity (MIA), SILV/PMEL17/GP100, Melan-A/MART-1, melanocortin-1 receptor (MC1R) and microphthalmia-associated transcription factor (MITF).

Promoters of the following proteins can also be used. For prostate cancer, the promoter can be from prostate-specific antigen (PSA), prostate-specific membrane antigen (PSMA), prostatic acid phosphatase (PAP), ARR2PB, PSA enhancer—rat probasin promoter, 1455 bp PSA enhancer upstream to PSA or hKLK2, or prostate-specific chimeric enhancer PSES. For breast cancer, the promoter can be hSCGB2A2 (for mammary carcinoma cells), DF3/MUC1, DF3 enhancer, or DF3 enhancer-DF3 promoter. For thyroid cancer, the promoter can be from thyroglobulin or calcitonin (CT). For lung tissue, the promoter can be a combination of the TTF1 gene driven by the hTERT promoter with 5 tandem copies of a portion of hSPA1, or hexokinase II. For liver tissue, the promoter can be liver-selective phosphoenolpyrovate carboxykinase, or albumin gene promoter. For pancreatic cells, the promoter can be RIP (rat insulin promoter) activated only in β cells. For brain cells, the promoter can be (1) targeting glioma: GFAP, Musashi, gfa 2, NSE, and (2) targeting glioma or glioblastoma: placing Nestin's 2nd intron before the 5' upstream region (2iNP). For hematopoietic and lymphatic tissue, the promoter can be HLA-Dralpha, CD4, CD19, or Ig kappa. From AIDS, the promoter can be the HIV-1 long terminal repeat (LTR) promoter. Any other suitable promoter can be used.

An on/off switch (i.e. activator) is attached to the gene, such as, but not limited to, one activated by antibiotics such as tetracycline, or by radiation, to enable control of the gene's activation. The activators can include a promoter (in addition to the promoter above used for selective expression).

In order to preferentially deliver the gene constructs to selected (or undesired) cells such as cancerous or infectious cells and not healthy cells, the gene construct can be packaged in an envelope made of nanoparticles or from viruses and which has on its surface receptors that direct the envelope and its content to the selected cells. One skilled in the art can readily obtain suitable envelopes. Nanoparticle or viral envelopes are delivery mechanisms used to encapsulate therapeutic treatments in order to cause the treatment to pass through tumorous tissues, but not pass through healthy tissue. The outside of the envelope is generally covered with molecules that are recognized by receptors present on tumor cells or infectious cells but not on healthy cells. This way, the therapeutic can more specifically be delivered to a tumor to achieve therapeutic concentrations of the gene constructs at the target tissue and to reduce potential damage to healthy tissue. Preferably, the envelope includes surface receptors that are specific for melanocytic and melanoma cells in order to treat melanoma. The envelope can be designed to be targeted to any cells desired to be eliminated.

Alternatively, the gene constructs of the present invention can be delivered in the form of a naked DNA plasmid or in various microbial vectors known in the art, including, but not limited to, retrovirus vectors, adeno-associated virus vectors, lentivirus vectors (Walther, et al., Drugs 2000 60:249-71), adenovirus vectors, vaccinia virus vectors, poxvirus vectors, and virus-like particles (Harrop, et al., 2006). Attenuated bacterial vectors can also be employed, such as species of *Salmonella, Shingella, Listeria, Yersinia,* and *Escherichia* (Vassaux, et al., J. Pathol. 2006 208:290-8). Cells can also be used as therapeutic carriers, including, but not limited to lymphocytes, neutrophils, monocytes, and stem cells (Roth, et al., Gene Ther. 2008 May; 15(10):716-29).

One very important advantage of the present invention is the ability of the gene constructs to activate apoptosis without triggering the apoptosis cascade that would normally be triggered in classical apoptosis-inducing therapies such as suicide gene therapy. The gene constructs of the present invention bypass all negative and positive inhibitory feedbacks that generally exist with programmed-cell-death executioner genes in order to destroy a targeted cell. The negative and positive inhibitory feedbacks are present at almost every level along the apoptosis cascade. The gene constructs of the present invention deliver the final effector of apoptosis, activated DNases, to their normal site of action, the nucleoplasm. One benefit of using the gene constructs of the present invention is that the number of patients that are able to respond to anti-cancer treatment is increased because the gene constructs of the present invention bypass many of the main treatment-resistant mechanisms of cancer, i.e. the apoptosis cascade. This is accomplished by triggering the chain of morphological, cancer-cell disintegration events from the last component of the apoptosis cascade. This is in contrast to current suicide gene therapies for cancer that use activating death-receptors (CD95, tumor necrosis factor (TNF)) at the beginning of the apoptosis cascade, or overexpressing intermediate apoptosis-cascade/cell-cycle components (Caspases, p53), which are dependent on an intact downstream chain of components. The gene constructs of the present invention can therefore be used in patients that are resistant to apoptosis-inducing gene therapies such as suicide gene therapy. Also, the gene constructs of the present invention are able to be used in patients that are resistant to other apoptosis-inducing treatments such as radiotherapy and chemotherapy. Therefore, a method of treating cancer (or any other disease as described herein) is provided by activating apoptosis of cancer cells (or any other desired cells) without triggering the apoptosis cascade.

Essentially, the gene constructs can be used to target any disease that has specific markers in the diseased cells. The gene construct can be targeted to promoters that are present in diseased cells, so that they can be selectively eliminated, leaving healthy cells intact. The gene constructs can be used to treat many different kinds of cancers, preferably malignant melanoma, but also prostate cancer, lymphoma, leukemia, throat, pancreatic, thyroid, ovarian, neuroendocrine (small cell lung cancer, neuroblastoma, carcinoid), or medullary thyroid cancer. Preferably, the cancer is in a tissue or organ that possesses a specific promoter/enhancer that can be used to target the gene construct's expression. In malignant melanoma, only melanocytic cells contain promoters for genes involved in the synthesis of the melanin pigment. The gene constructs can also be used to treat infectious diseases such as, but not limited to, HIV, AIDS, malaria, and Leishmania. The gene construct can also be used to eliminate specific cells, such as, but not limited to, subtypes of immune cells that are involved in the etiology of chronic inflammatory diseases such as rheumatoid arthritis, inflammatory bowel disease (Crohn's disease, ulcerative colitis), or graft-versus-host disease (GVHD). Any disease that involves specific types of T cells can also be targeted. While cancer cells are specifically discussed, it should be understood that the methods herein apply to any cells desired to be eliminated from a patient, provided that they produce a unique protein to the targeted tissue/organ.

A method of eliminating undesired cells from a patient is provided, including the steps of administering a therapeutic containing a gene construct, delivering the therapeutic to undesired cells, and destroying the cells. Preferably, this method is used to treat cancer, especially malignant melanoma, and the undesired cells are cancerous or tumorous cells. The gene construct is administered in the envelope as described above, through the use of a gene gun or injection. Other methods of administration are further described below. The gene construct is preferentially delivered to the undesired cells and not healthy cells due to the surface receptors that direct the envelope and its content to the undesired cells. The gene constructs are able to gain access to the nucleus due to their modifications as described above and destroy the cell. In summary, removing the signal peptides prevents the cell from packing the gene construct in an endosome and shipping it out of the cell (secreting the gene construct). Adding an NLS provides the gene construct an access into the nucleus; hence, it can come in vicinity to the target DNA in order to defragment it. Knocking down the binding site for actin prevents actin from inhibiting the gene construct.

More specifically, a method is provided of treating malignant melanoma by administering a therapeutic containing a genetically modified DNA-degrading enzyme at the core of a gene construct, such as a hrDNase 1 gene construct, delivering the therapeutic to melanoma cancer cells, and destroying the melanoma cancer cells. The treatment is advantageous over other prior art treatments, because the gene constructs include components that limit the expression to targeted cells and not non-targeted cells, and the envelope used for delivery of the gene construct includes surface homing receptors that target the gene construct to the tissue of choice, thereby allowing the gene construct to accumulate in the targeted tissue and further reducing side effects for the patient, as further described below.

The therapeutics of the present invention enable treatment of cancer in patients with a compromised immune system, or even a severely compromised immune system, since they do not require the participation of the immune system. This is in contrast to current cancer therapies that are immunotherapeutic approaches and dependent on the recruitment of a patient's immune system in order to fully function. A substantial number of patients having cancer metastases also have deficiencies in their immune system functions. The present invention can therefore treat more patients than other current therapies due to the fact that a fully functioning immune system is not required for effectiveness of the therapeutics herein.

Therefore, a method is provided of treating a cancer patient having a compromised immune system, by administering a therapeutic containing a gene construct to a patient having a compromised immune system, delivering the therapeutic to tumor cells, destroying the tumor cells, and treating cancer.

Another advantage to the present invention is that it has fewer side effects than current cancer therapies, since the present invention enables the elimination of cancer cells without a significant damage to neighboring healthy cells. In the present invention, treatment with the modified programmed-cell-death executioner genes of the present invention did not show any killing of non-transfected cells. In other words, bystander effect, which leads to the killing on non-transduced tumor cells, was not observed in any of the dozens of experiments conducted with the DNase constructs during a period of over a year. In contrast, the most currently investigated suicide gene-therapy approaches such as HSV-tk are dependent on non-direct killing (bystander effect) due to low efficiency in direct killing. Suicide genes encode a protein that activates a cytotoxic prodrug. The activated drug can leak or be secreted to kill nearby nontransfected bystander cells. The lack of bystander effect in a treatment for cancer is important because the bystander effect of HSV-tk has been shown to be associated with damage to neighboring healthy cells and with death in treated animals. The present invention therefore provides a larger margin of safety for cancer patients, as healthy cells are protected. The gene constructs also avoid necrosis elicited by toxin-conjugated Abs. Necrosis is the premature death of cells that is caused by external factors, such as trauma, infections, or toxins. The content of dying cells reaches the intercellular space and causes a strong immune reaction that increases the damage to the tissue by killing healthy cells, which were not subject to the original insult. In contrast, apoptosis is a physiological, intracellular mechanism that allows the elimination of dying cells without provoking harmful immunogenic reactions.

Therefore, a method is provided of treating cancer and reducing side effects, by administering a therapeutic containing the gene construct, preferentially delivering the therapeutic to tumor cells and not healthy cells, destroying the tumor cells, and treating cancer.

An array is also provided in the present invention that is generated of at least two gene constructs each having different killer genes at their core, such as a gene encoding a DNA-degrading enzyme, different promoters and different nuclear localization signals. This enables personalized treatment of a patient having a tumor by treating this patient with a gene construct containing a promoter that can be active within a patient tumor and treating the patient with the gene-construct expressing the highest killing efficiency for the tumor. Cancer cells, obtained from diagnostic biopsy on a patient, are grown in the laboratory and exposed to the various gene constructs to determine sensitivity level. The patient is then treated with the gene construct expressing the highest killing efficiency. This approach is very similar to choosing the most efficient antibiotics that can kill certain bacteria; however, instead of different antibiotics, different gene constructs are used and instead of different dishes of the same insulting bacteria, different cell cultures of the same type of cancer are used. This is in contrast to all currently investigated gene therapy approaches, which offer only one genetic target. Personalizing anti-cancer treatment is important because the same type of cancer in different individuals can express different inactivated apoptosis elements and use different bottom-cascade killer genes. Hence, the current gene therapy approaches whether used alone or in combination with chemotherapy or radiotherapy still have low therapeutic efficiency.

The array can also include gene constructs that have different promoters as previously listed above. This array is useful in determining what type of cancer or disease a patient has.

One example of an array is as follows. DNase 1, DNase 1-L2, DNase 2B, DNase X can be included and use any of the 5 NLSs mentioned above, in LD1. Hence, there are 20 different gene constructs that can be prepared by these combinations, each of which can be included in an array.

Thus, a method of personalizing anti-cancer treatment is provided by taking a sample of cancerous cells from a patient, applying the cells to an array of gene constructs in which all of the constructs differ with respect to the programmed-cell-death executioner gene and with respect to the nuclear localization signal, selecting the gene construct with the highest sensitivity to the cancerous cells, and treating the patient with the selected gene construct. The patient is treated as described above, enclosing the gene construct in the envelope, delivering the gene construct to cancerous cells, and destroying the cells. This method can also be practiced with any other cells that are desired to be eliminated from the patient, in order to select the best method of treatment. More than one gene construct can be used to treat the patient, depending on how many gene constructs in the array respond to the sample of the patient's cells. This is useful because many cancers evolve and change as they progress and thus targeting only one type of cell will not eradicate the cancer. Multiple gene constructs can therefore be used to fully treat the patient.

The array can also be used as a diagnostic device to determine if a patient has cancer by taking a sample of cells in a patient, determining if a gene construct in the array is sensitive to the cells, and if cells are sensitive to at least one gene construct, determining that the patient has cancer. Preferably, in this method, the array includes gene constructs with different promoters as well as different killer genes and NLSs. This can be a preliminary determination, and the diagnosis can prompt the patient to get further testing. The use of the array as a diagnostic device can also be used to diagnose a patient with other infectious diseases.

The gene construct of the present invention can further include various mutations to modify properties of the gene construct. A preferred type of mutation is the mutation of an inhibitor-binding site of an enzyme such as a DNA-degrading enzyme, to render the enzyme less sensitive to its inhibitors. For example, DNase 1 resistance to actin binding can be increased by mutating native amino acids at an actin binding site of the DNase 1 gene at Glu-13, His-44, Asp-53, Tyr-65, Val-66, Val-67, Glu-69, Ala-114, and combinations thereof. Other examples of actin binding sites that can be changed are listing in TABLE 1 below. Also, the catalytic activity of DNA-degrading enzyme can be increased by mutation of appropriate amino acids. For example, the catalytic activity of DNase 1 can be increased by mutating native amino acids of the DNase 1 gene to change the electrical charge of Gln-9, Glu-13, Asn-74, and combinations thereof.

In the Example below, it is shown that it is possible to use genetically engineered DNA, as a single therapeutic modality, to induce apoptotic cell death in human cancer cells characterized by high resistance to apoptosis both by ultraviolet irradiation and chemicals. The therapeutic resistance is conferred through disruption of death pathways at multiple levels.

It is shown that the above has been achieved by overexpressing in the cells a DNase 1 enzyme's cDNA engineered to include all the following modifications (Constructs C11 & C13):

1. Removal of the Signal peptide (SP), encoded by a nucleotide sequence upstream to the DNase 1's N-terminus.

2. Fusion of a Nuclear localization signal (NLS) to the DNase 1's cDNA.

3. Mutation of nucleotides in DNase 1's binding site to actin that resulted in an amino-acid substitution.

These modifications prevented the modified enzyme from entering into the secretory pathway, directed the enzyme to enter the cell's nucleus, and conferred DNase 1 resistance to its major inhibitor, actin, which is abundant in both the cytoplasm and the nucleus.

It is not obvious that overexpression of the DNase 1 endonuclease should result in cell's DNA degradation, followed by cell death. It is shown herein that overexpression of Wild-type (native) DNase 1 (Construct C03) was not sufficient to reduce cell survival nor to induce apoptosis.

Furthermore, it is not obvious that fusing a Nuclear localization signal (NLS) to the overexpressed Wild-type DNase 1 endonuclease should result in cell's DNA degradation, followed by cell death. It is shown herein that overexpression of Wild-type DNase 1-NLS (Construct C01) was not sufficient to reduce cell survival nor to induce cell death.

It is not obvious that removing the Signal peptide from the overexpressed Wild-type DNase 1 endonuclease fused with NLS should result in cell's DNA degradation, followed by cell death. It is shown herein that overexpression of DNase 1-NLS lacking a Signal peptide (Constructs C07 and C09) was not sufficient to reduce cell survival nor to induce consistent significant apoptosis.

Also, it is not obvious that fusing a Nuclear localization signal (NLS) to the overexpressed DNase 1-NLS lacking a Signal peptide is sufficient to induce the highest level of decreased cell survival and increased apoptosis above the baseline controls. It is shown herein that the NLS should be fused to the C-terminus (Construct C11) to achieve a cancer cell killing efficiency of 70-100% as compared to only ~40% if the NLS is fused to the N-terminus (Construct C13).

The concepts demonstrated in the examples below are readily extendable to additional DNA-degrading enzymes. For example, it can be expected that a nucleus-directed construct including a DNA-degrading enzyme sensitive to a nuclear inhibitor other than actin will show increased killing efficiency when the relevant inhibitor-binding site is mutated to reduce inhibitor binding.

Delivery of Therapeutics:

The gene constructs of the present invention are administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compounds of the present invention can be administered in various ways. It should be noted that they can be administered as the compounds and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compounds of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

Example 1

Materials.

Dulbecco-S Phosphate-buffered saline (PBS), RPMI 1640 medium, Fetal Calf Serum (FCS), L-Glutamine 200 mmol, and 0.5% Trypsin/5.3 mm EDTA were purchased from Fisher (Fairlawn, N.J.), and Invitrogen (Grand Island, N.Y.). Dimethyl sulfoxide (DMSO from Sigma (St. Louis, Mo.).

Cell Culture and Transfection.

Human melanoma Mel-Juso cell line DSMZ), Braunschweig, Germany) was cultured in RPMI 1640 medium. The media was supplemented with 10% FCS and 1% glutamine. The cells were grown to confluence and re-seeded for at least 24 hours before transfection. Cultures were maintained at 37° C. in a humidified 5% CO2 atmosphere. Cells were plated in 6 well plates at a density of 8×105 cells/well for TUNEL (Terminal transferase dUTP Nick-End Labeling) and DNA fragmentation assays, at a density of 4×105 cells/well for Western blot and at a density of 600 cells per well for colony forming assay (CFA). After 24 hours, the cells were transfected with 2 µg of DNA (gene construct) using Lipofectamine LTX and Plus reagent (Invitrogen, Carlsbad, Calif.) according to the manufacturer's instructions. The transfection was conducted in a final volume of 1 ml. After 4 hours, fresh media was added and cells were incubated until set times for harvesting, described below, had been reached. For Laser scanning cytometry (LSC) cells were grown on 8-chamber slides (Lab-Tek II: Nalgen Nunc International, Naperville, Ill.) and transfected with 0.5 µg of each DNase 1 construct using Lipofectamine LTX and Plus reagent as described above.

Constructs.

Figure 5:
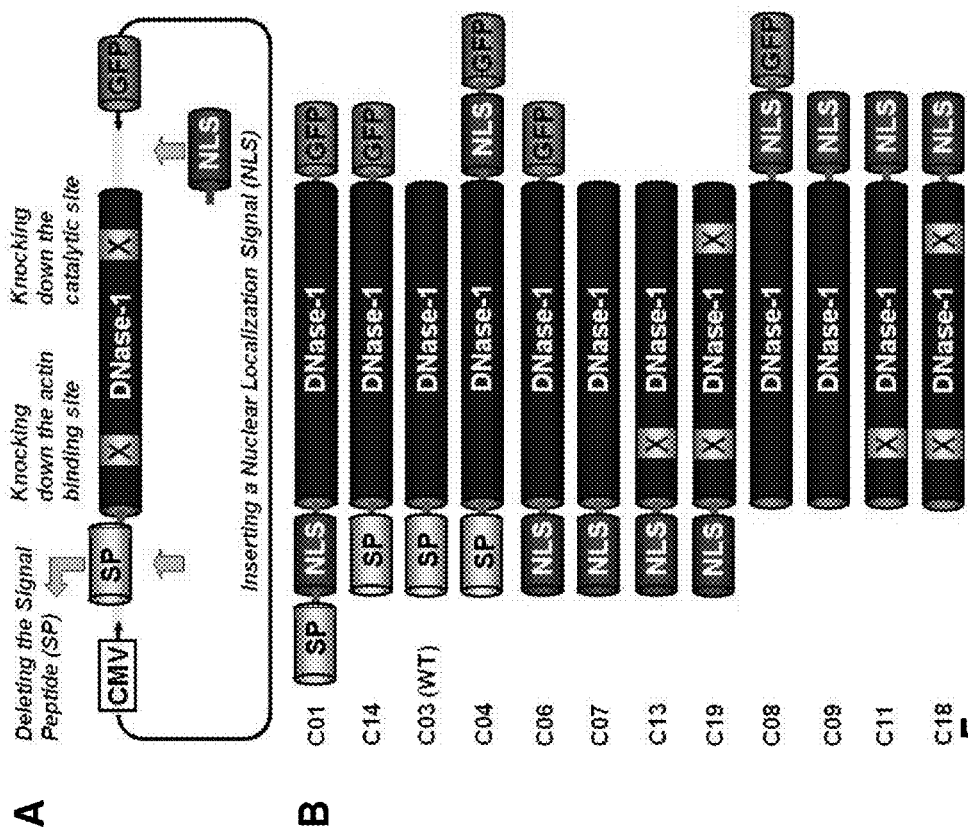
FIGS. 5A and 5B are schematic representations of the designed gene constructs, wherein 5A shows the genetic alterations used for generating the DNase 1 constructs, and 5B shows the composition of the expressed DNase 1 protein constructs (Cytomegalus virus promoter (CMV), Signal peptide (SP), Deoxyribonuclease-1 gene (DNase 1), nuclear localization signal (NLS), green fluorescent protein (GFP), mutation of an actin binding site (X on left side of DNase 1 symbol), mutation of a proteolytic activity site (X on right side of DNase 1 symbol))
Figure 15:
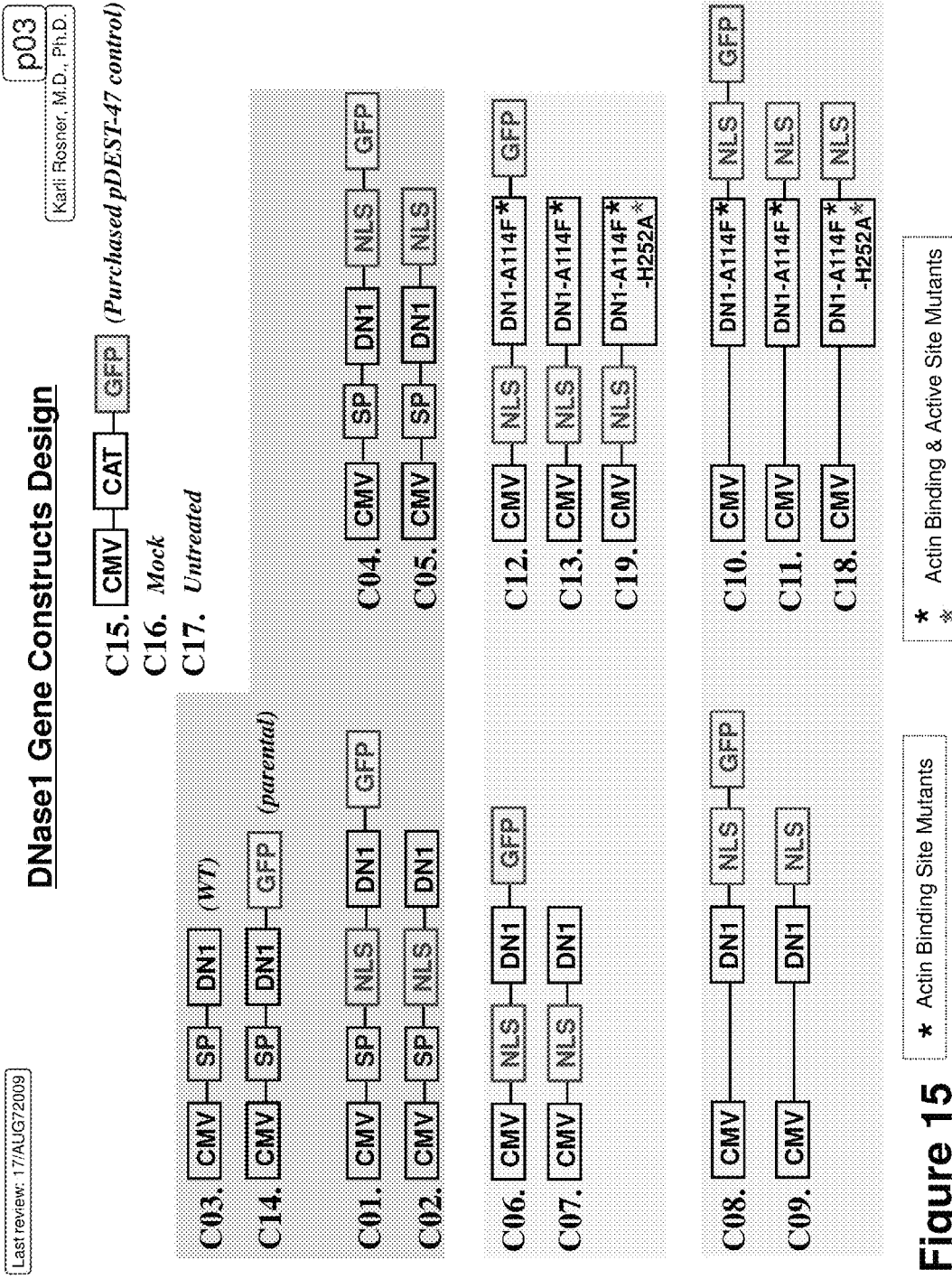
FIG. 15 is a flow chart of DNase 1 gene constructs design.
Figure 16:
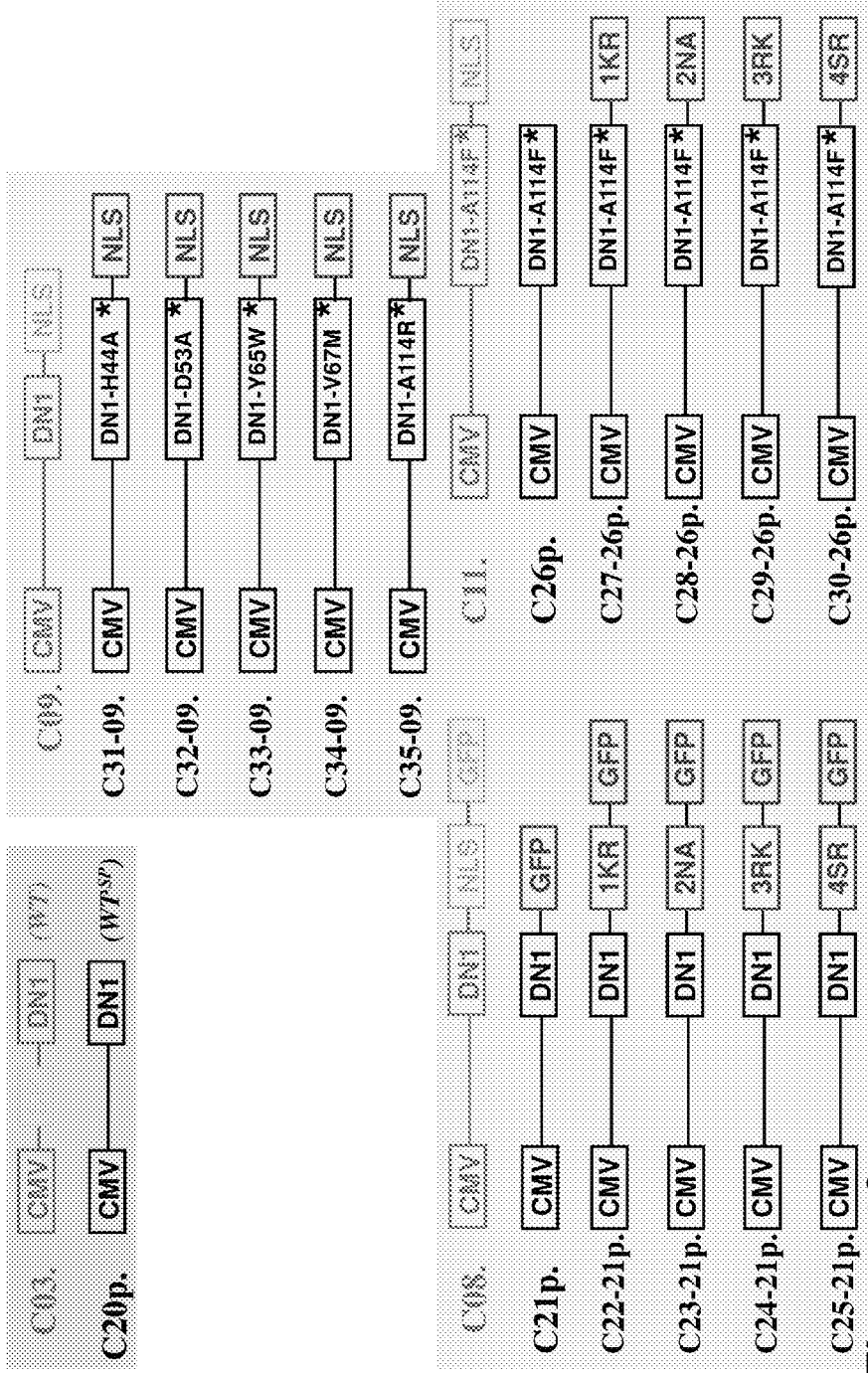
FIG. 16 is a flow chart of DNase 1 gene constructs design.
Figure 17:
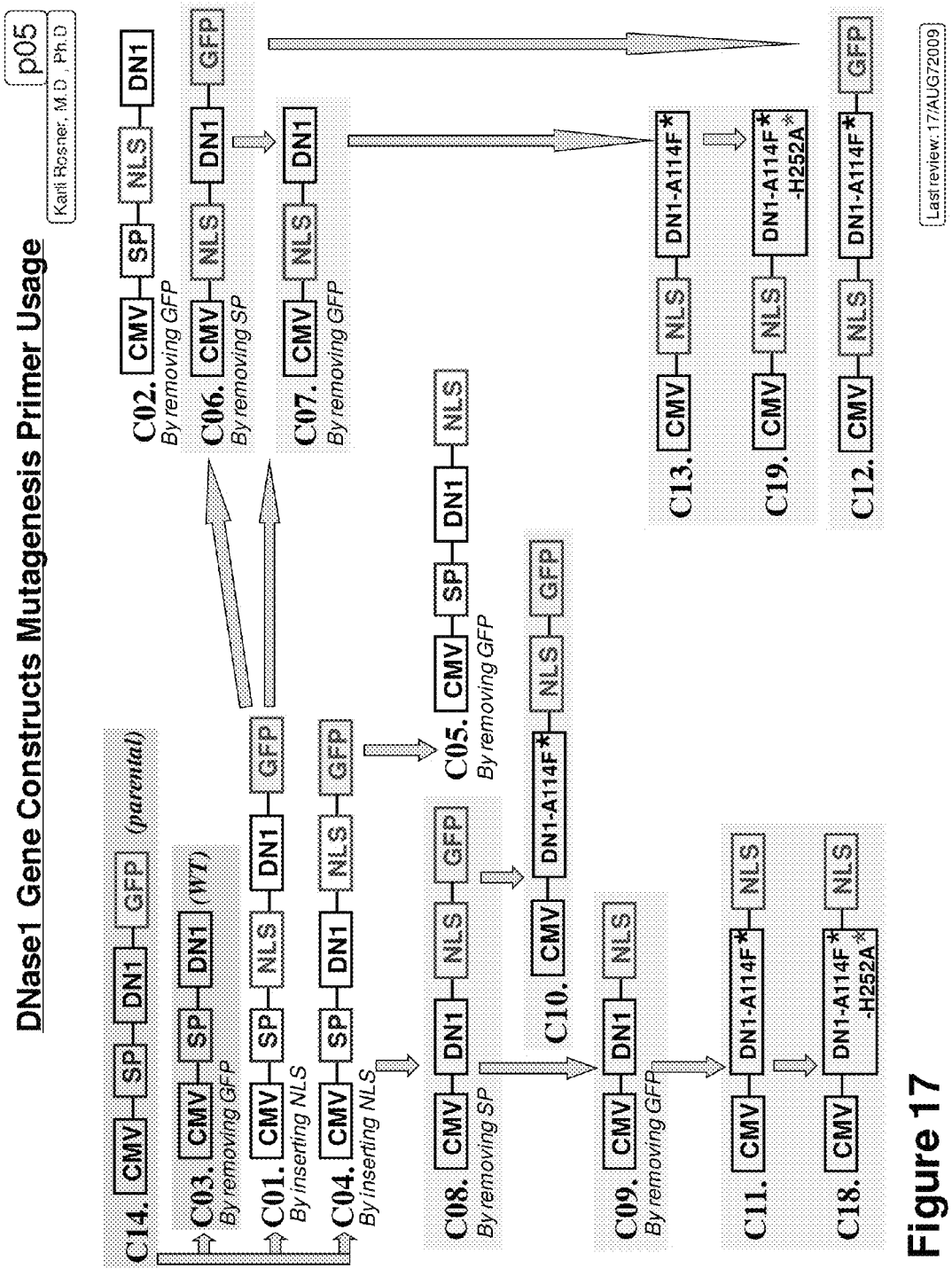
FIG. 17 is a flow chart of DNase 1 gene construct mutagenesis primer usage.
Figure 18:
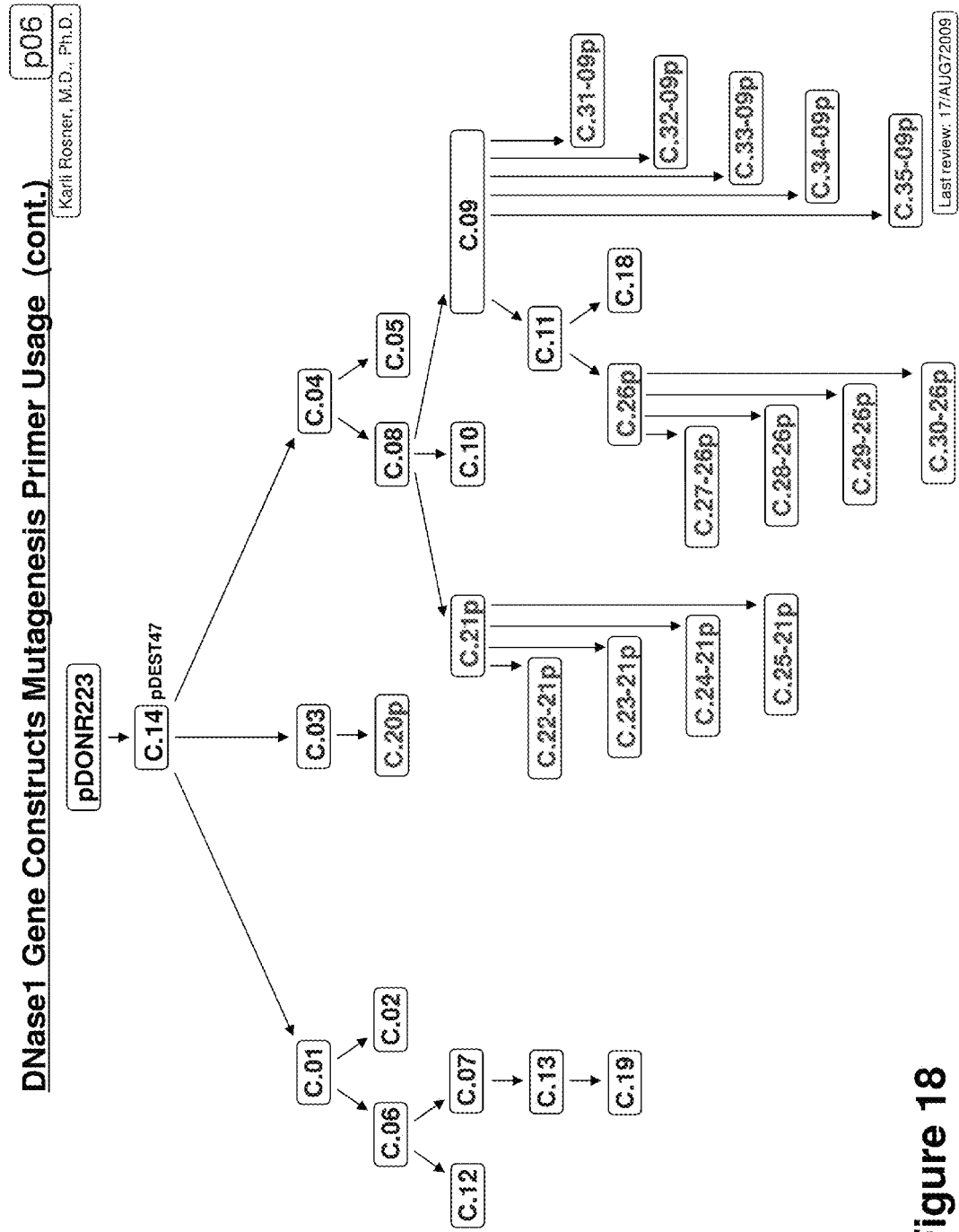
FIG. 18 is a flow chart of DNase 1 gene construct mutagenesis primer usage.
Figure 19:
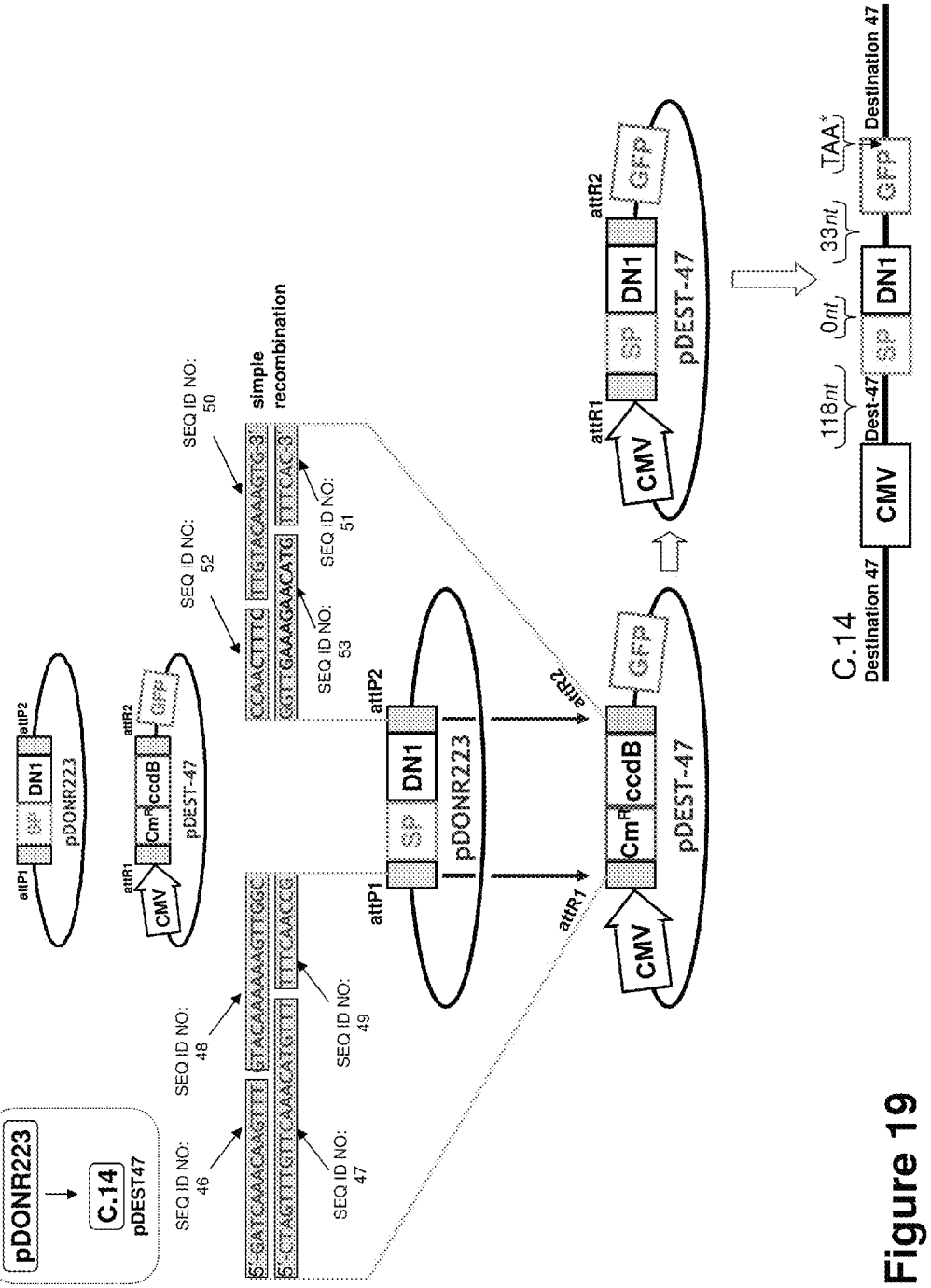
FIG. 19 is a flow chart of DN1 transfer from pDONR223 to pDEST-47.

The generated DNase 1 constructs are described in FIGS. 5A and 5B and the used primers in Table 1. The Signal peptide (SP) was removed by deleting the 22 amino acids upstream to the first DNase 1 codon. Partial resistance was rendered to actin by mutating one of the several amino acids involved in binding actin, A114F, in DNase 1 constructs 011, C13, C18 and C19. The catalytic activity of the enzyme was compromised by mutating one of the two catalytic sites, H252A, in DNase 1 constructs C18 and C19. The SV-40—Nuclear Localization Signal (NLS), PPKKKRKV (SEQ ID NO: 1) was added to the DNase 1 gene at the N-terminus of gene-constructs 007, C13 and C19, and at the C-terminus of gene-constructs C09, C11 and C18.

TABLE 1

Primer sequences used to generate the DNase 1 gene constructs

| Primer | Sequence | |
|---|---|---|
| 114 | 5'-cgacaccttcaaccgagagccaTTcattgtcaggttcttctcccg g-3' | (SEQ ID NO: 7) |
| 114-rc | 5'-ccgggagaagaacctgacaatgAAtggctctcggttgaaggtgtc g-3' | (SEQ ID NO: 8) |
| ForPrimer252HtoA | 5'-ggcccaagccatcagtgacGCAtatccagtggaggtgatgctgaagtg cccgccg-3' | (SEQ ID NO: 9) |
| P1-NLS-for | 5'-actggcggccctactgcaggggggccgtgtccccgccgaaaaagaaacg caaagtg-3' | (SEQ ID NO: 10) |
| P2-20p5-rc | 5'-ggtctccccaaatgtctggatgttgaaggctgcgatcttcagcatgcc agcttttttgtaca-3' | (SEQ ID NO: 11) |
| P2-NLS-20p5-rc | 5'-ggtctccccaaatgtctggatgttgaaggctgcgatcttcagcacttt gcgtttcttttcggcggcatgccagcttttttgtaca-3' | (SEQ ID NO: 12) |
| P2-NLS-rc | 5'-ggtctccccaaatgtctggatgttgaaggctgcgatcttcagcacttt gcgtttcttttcggcgg-3' | (SEQ ID NO: 13) |
| P3-for-20p6 | 5'-ccaagccatcagtgaccactatccagtggaggtgatgctgaagtgcta atgaattaaacccgctga-3' | (SEQ ID NO: 14) |
| P3-NLS-for | 5'-ccaagccatcagtgaccactatccagtggaggtgatgctgaagtgccc gccgaaaaagaaacgcaaagtg-3' | (SEQ ID NO: 15) |
| P4-NLS-rc | 5'-tcaacaagaatgggacaactccagtgaaaagttcttctccttttgcta gccatcactttgcgtttcttttcggcgg-3' | (SEQ ID NO: 16) |
| P5-for | 5'-gacccaagctggctagttaagcttgatcaaacaagtttgtacaaaaaa gctggcatg-3' | (SEQ ID NO: 17) |
| P6-NLS-rc | 5'-ggcaactagaaggcacagtcgaggctgatcagcgggtttaattcatta cactttgcgtttcttttcggcgg-3' | (SEQ ID NO: 18) |
| P6-rc | 5'-ggcaactagaaggcacagtcgaggctgatcagcgggtttaattcatt a-3' | (SEQ ID NO: 19) |
| RevPrimer252HtoA | 5'-cggcgggcacttcagcatcacctccactggataTGCgtcactgatggc ttgggcc-3' | (SEQ ID NO: 20) |

Introduced mutations are shown in upper case and underlined.

Generation of Parental Construct C14.

Full-length open reading frame (ORF), wild-type Dnase-1 (Accession No. NM_005223) (SEQ ID NO: 6) was obtained from the GATEWAY donor vector pDONR223 (Open BioSystems, Huntsville, Ala.) and subcloned in frame into a GFP-tagged eukaryotic expression vector, GATEWAY pcDNA-DEST 47 (Invitrogen, Carlsbad, Calif.), using manufacturer's instructions, generating construct C14.

Klenow Reaction.

The large fragment of DNA polymerase (Klenow fragment) was used to elongate primer pairs (Integrated DNA Technologies (IDT), Coralville, Iowa) from an overlapping region where the pairs were annealed to create very long and stable primers to be used in all subsequent mutagenesis reactions except for generating actin-binding and catalytic site mutants.

Mutagenesis.

Subsequent deletions, insertions, and site directed mutations (FIGS. 14-31) were generated using site-directed mutagenesis QuikChange Lightning Site-Directed Mutagenesis Kit (#210518; Stratagene, Cedar Creek, Tex.) following the manufacturer's instructions. Clones for each of the mutagenesis products were picked up from agar plates supplemented with ampicilin (Sigma, St. Louis, Mo.) and gown overnight in ampicilin supplemented LB culture. DNA was extracted from bacterial clones using maxiprep/miniprep (K2100-16; Invitrogen, Carlsbad, Calif./27405; Qiagen, Germantown, Md.) following manufacturers' instructions and sent for sequencing (Applied Genomics Technology Center, Detroit, Mich.). Chloramphenicol transferase (CAT) reporter plasmid (pcDNA/GW-47/CAT) served as a control (#12281-010, Invitrogen).

Generation of Wild Type Dnase-1 (C03), C01 and C04 from Parental Construct C14.

Figure 20:
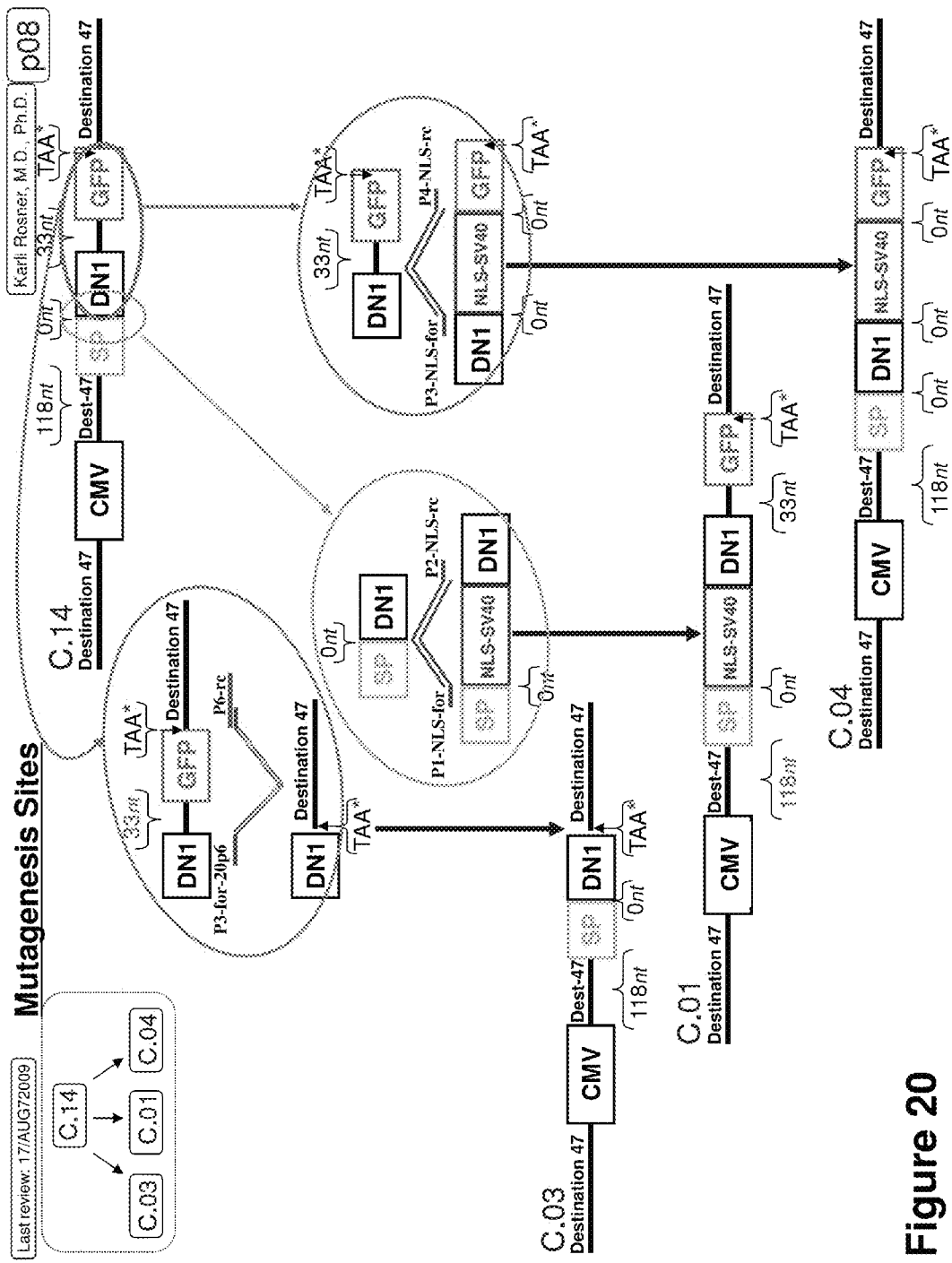
FIG. 20 is a flow chart of mutagenesis sites.

Deleting the Green Fluorescence Protein (GFP) from C14 using the P3-for-20p6 and P6-rc primers generated wiled type DNase-1 (C03) (FIGS. 20, 32). SV40—Nuclear Localization Signal (NLS) was inserted at 5'-prime and 3' prime of C14 to generate constructs C01 and C04, respectively. C01 was generated with P1-NLS-for and P2-NLS-rc primers (FIGS. 20, 31) and C04 was generated with P3-NLS-for and P4-NLS-rc primers (FIGS. 20, 32).

Generation of C20p from C03 Construct.

Figure 21:
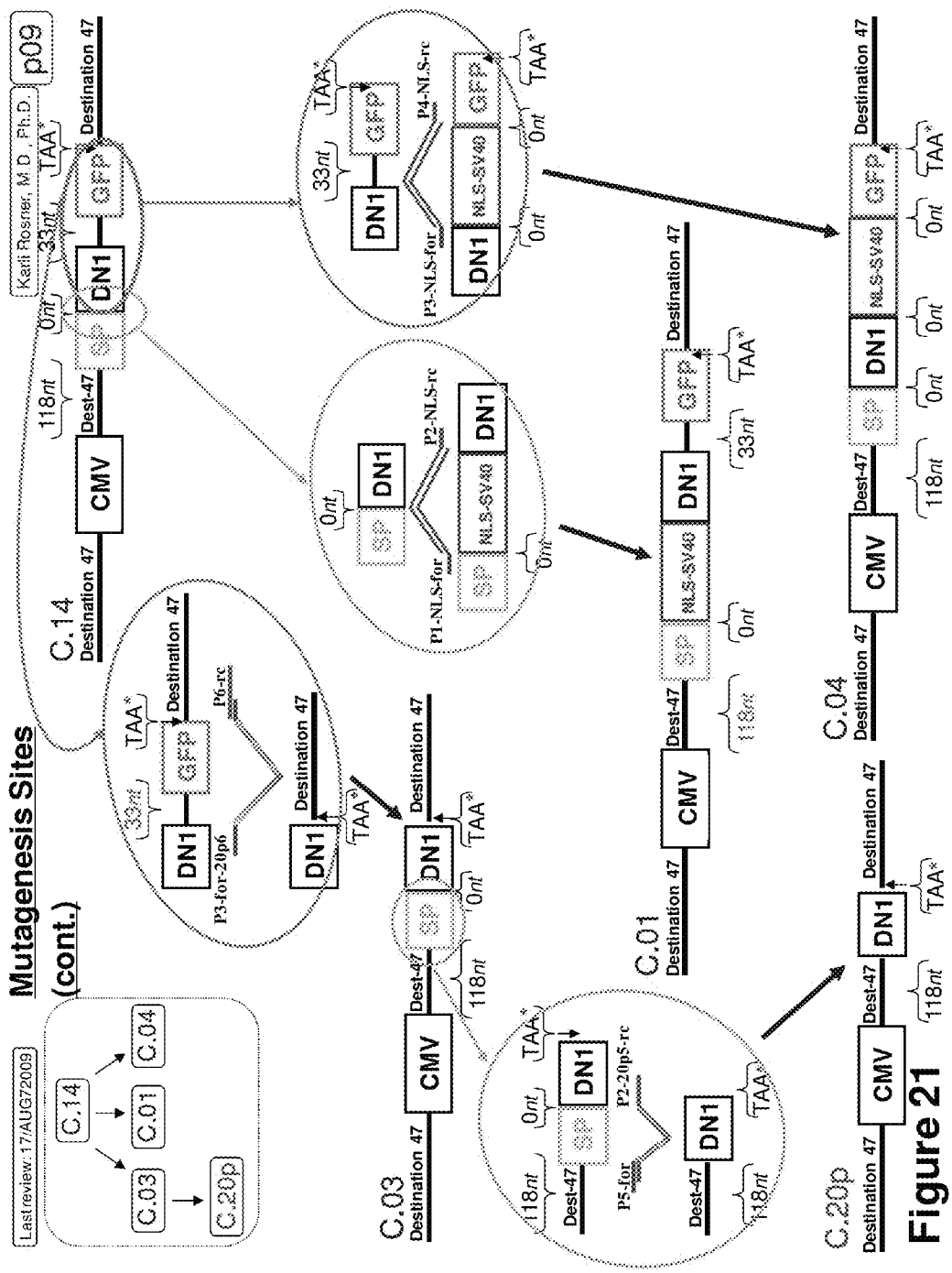
FIG. 21 is a flow chart of mutagenesis sites.

The signal peptide was removed from C03 to generate C20p, using P5-for and P2-20p5-rc primers (FIGS. 21, 32).

Generation of C08 and C05 from C04 Construct.

Figure 25:
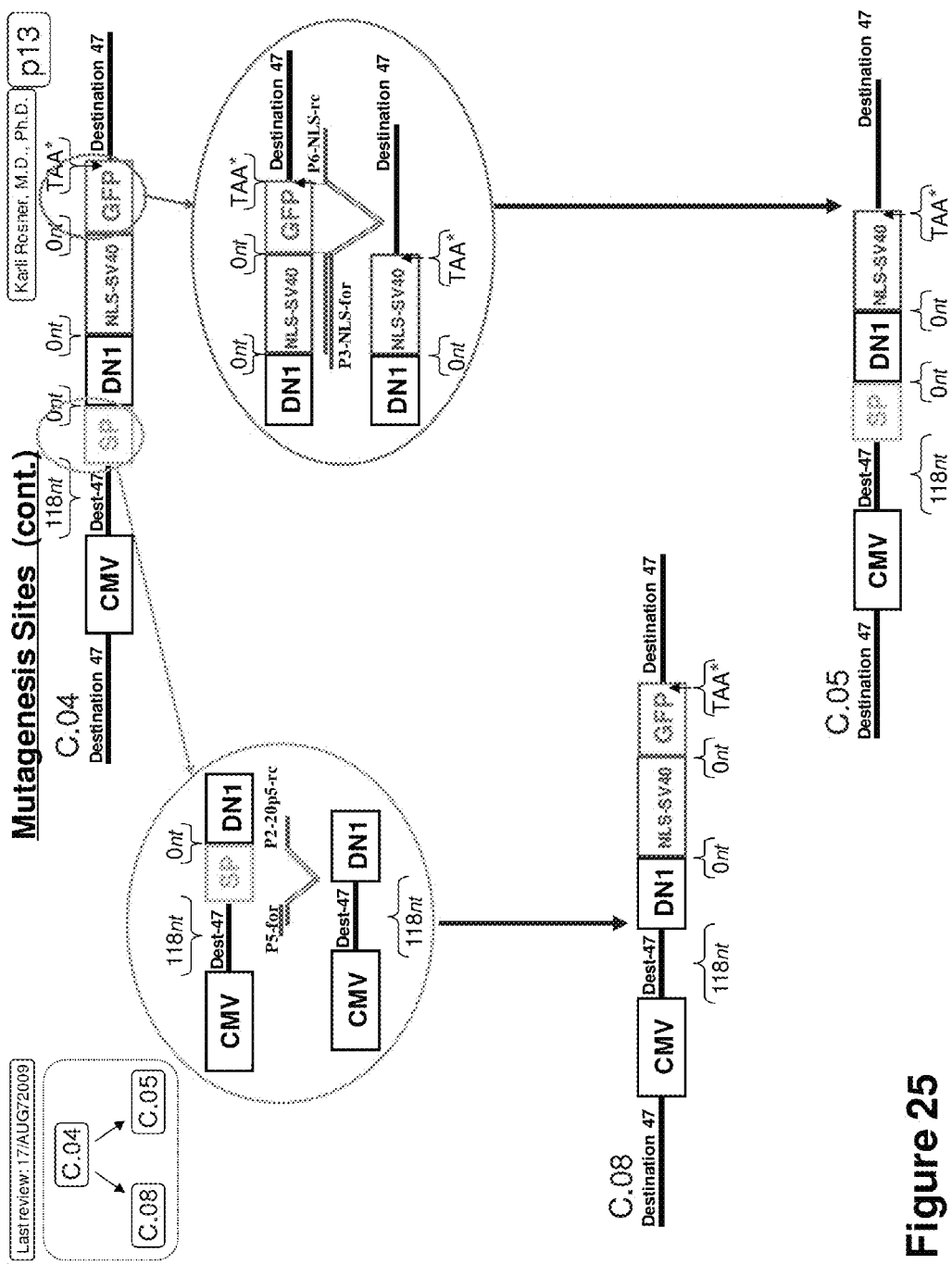
FIG. 25 is a flow chart of mutagenesis sites.

The signal peptide was removed from C04 to generate C08, using P5-for and P2-20p5-rc primers (FIGS. 25, 32). To remove the GFP from C04 and generate C05 P3-NLS-for and P6-NLS-rc primers were generated (FIGS. 25, 32).

Generation of C21p, C10 and C09 from C08 Construct.

Figure 26:
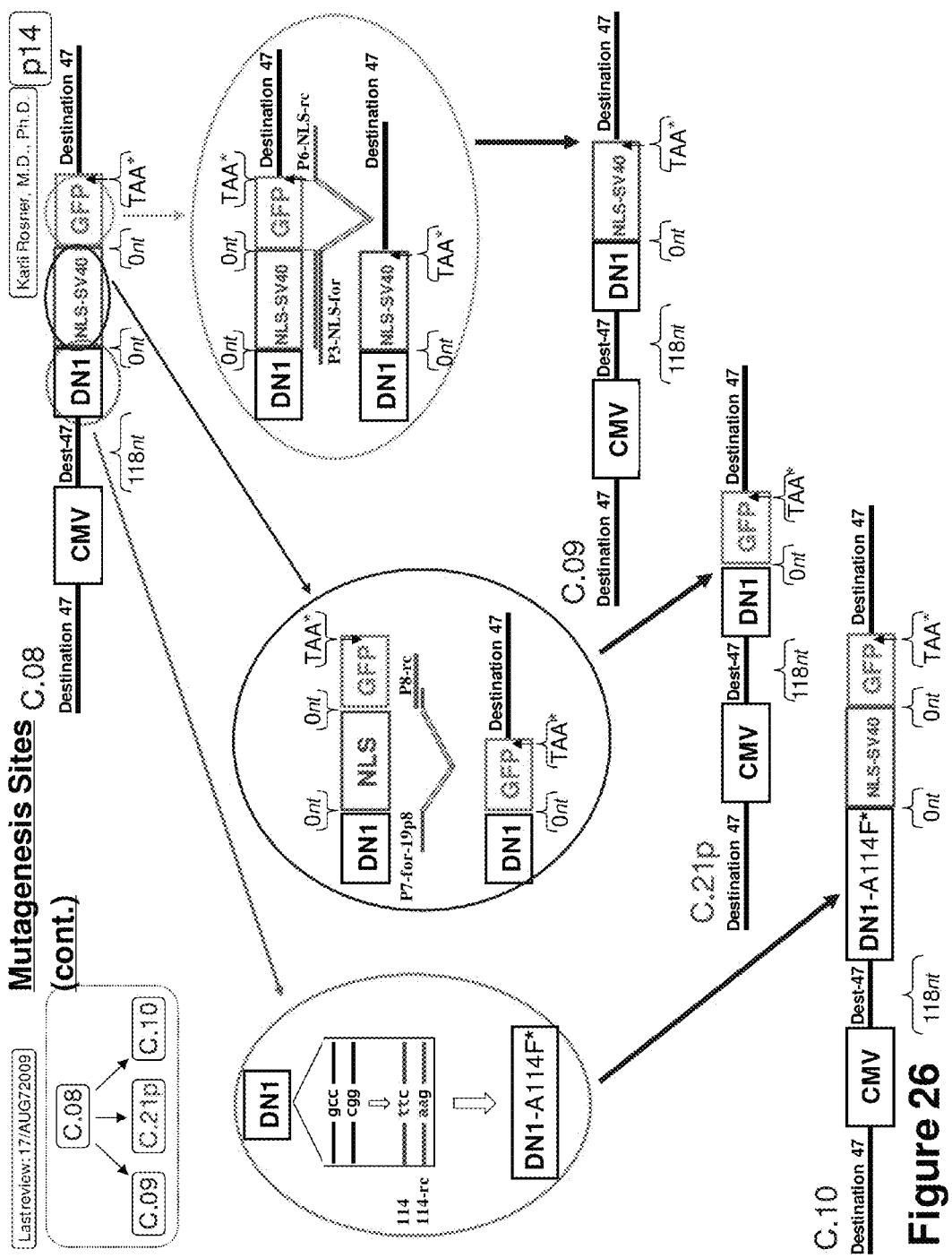
FIG. 26 is a flow chart of mutagenesis sites.

To remove the NLS from C08 and generate C21p, P7-for-19p8 and P8-rc primers were generated (FIGS. 26, 33). The alanine amino acid was mutated to phenylalanine at position 114 of DNase 1 of C08 using 114 and 114-rc primers to generate C10 (FIGS. 26, 32). The GFP was removed from C08 to generate C09, using P3-NLS-for and P6-NLS-rc primers (FIGS. 26, 32).

Generation of C22-21p, C23-21p, C24-21p and C25-21p from C21 p Construct.

Figure 27:
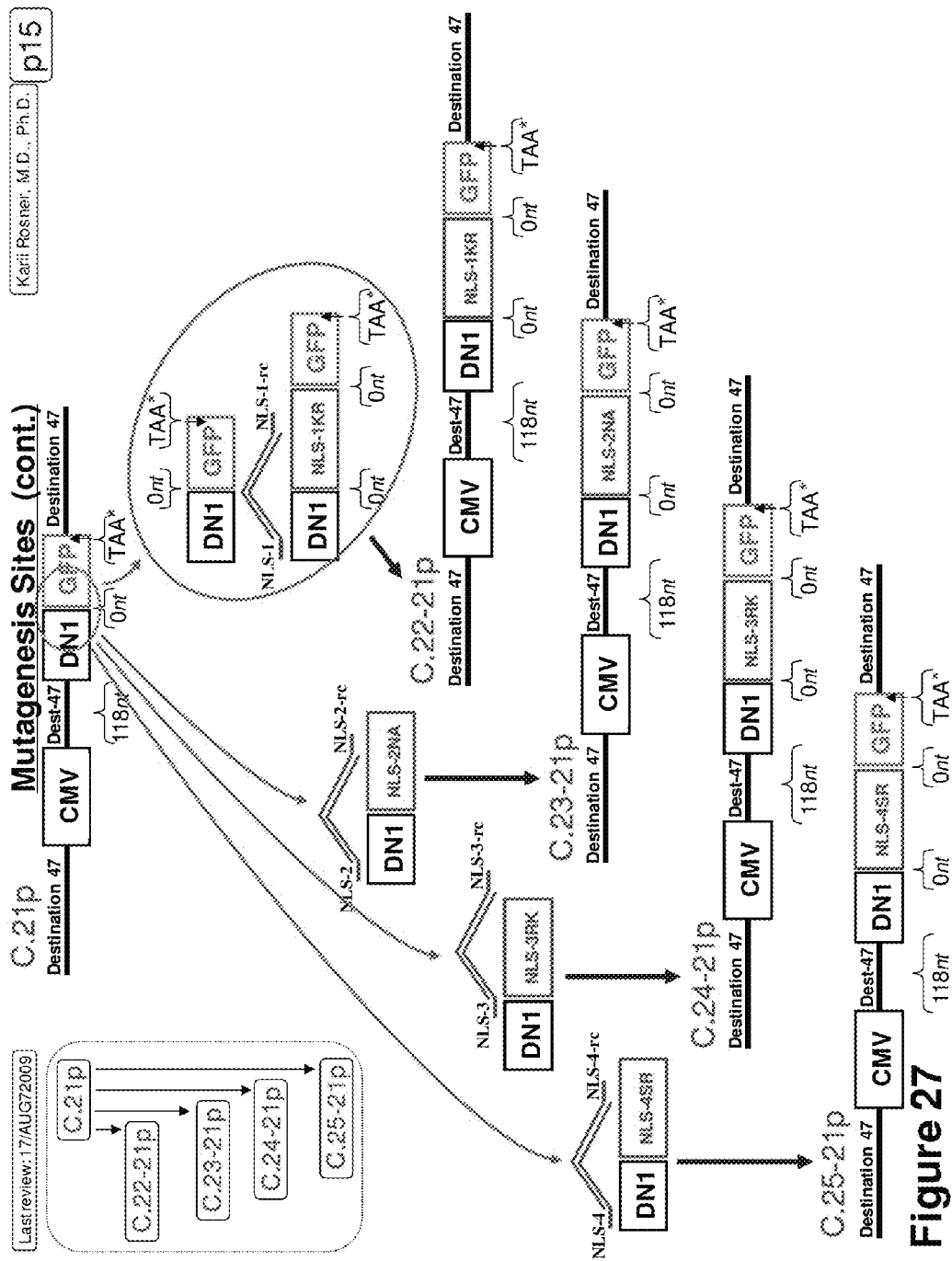
FIG. 27 is a flow chart of mutagenesis sites.

Four different NLSs were designed to be inserted into C21p at the 3'-prime of DNase-1 gene, thus, generating four different constructs. The NLS-1/NLS-1-rc, NLS-2/NLS-2-rc, NLS-3/NLS-3-rc, and NLS-4/NLS-4-rc primers were generated to insert NLS-1KR, NLS-2NA, NLS-3RK, and NLS-4SR, respectively, into C21p. Thus, to generate C22-21p, C23-21p, C24-21p and C25-21p constructs (FIGS. 27, 33).

Generation of C11, C31-09p, C32-09p, C33-09p, C34-09p, and C35-09p, from C09 Construct.

Figure 28:
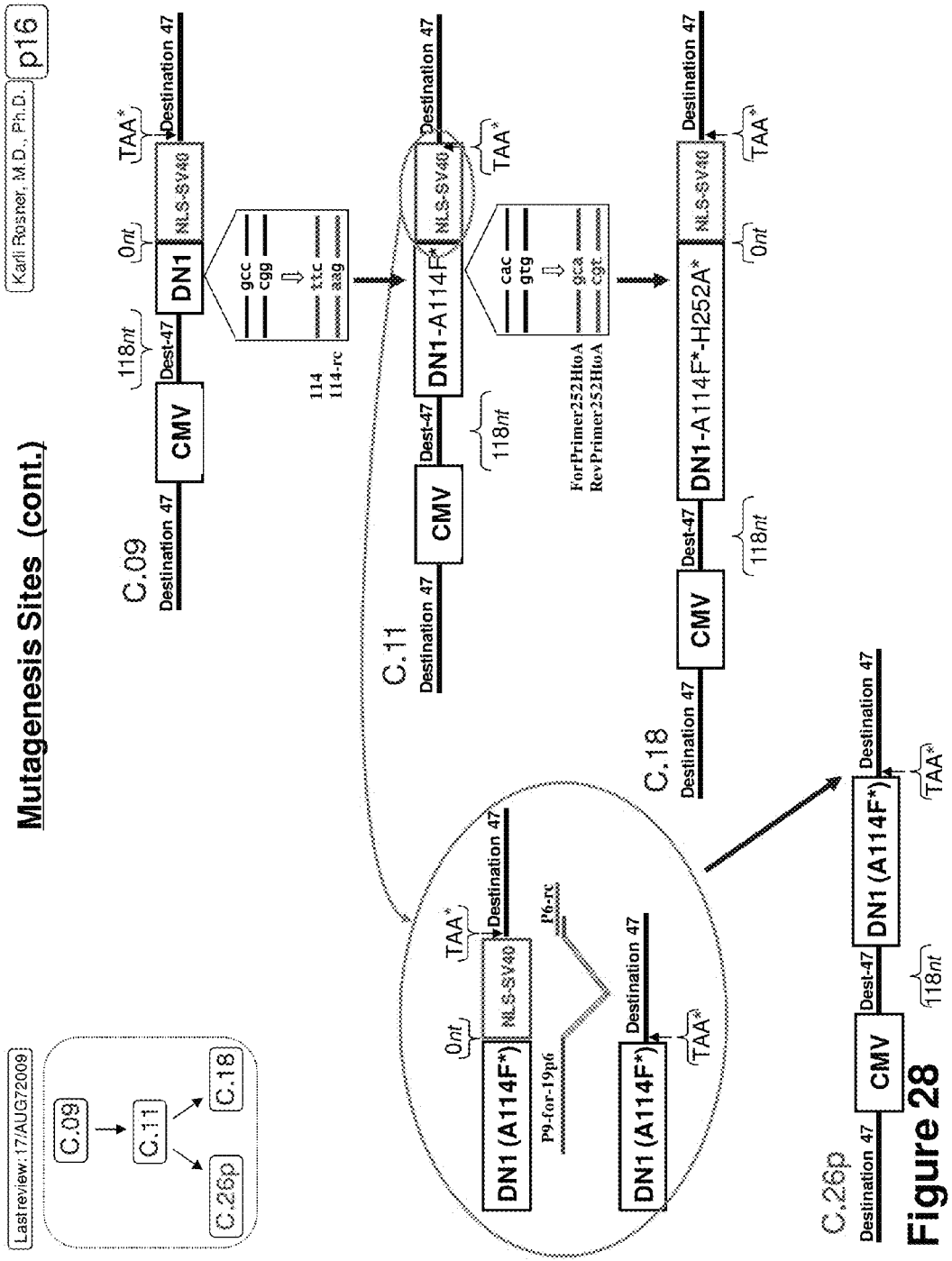
FIG. 28 is a flow chart of mutagenesis sites.
Figure 30:
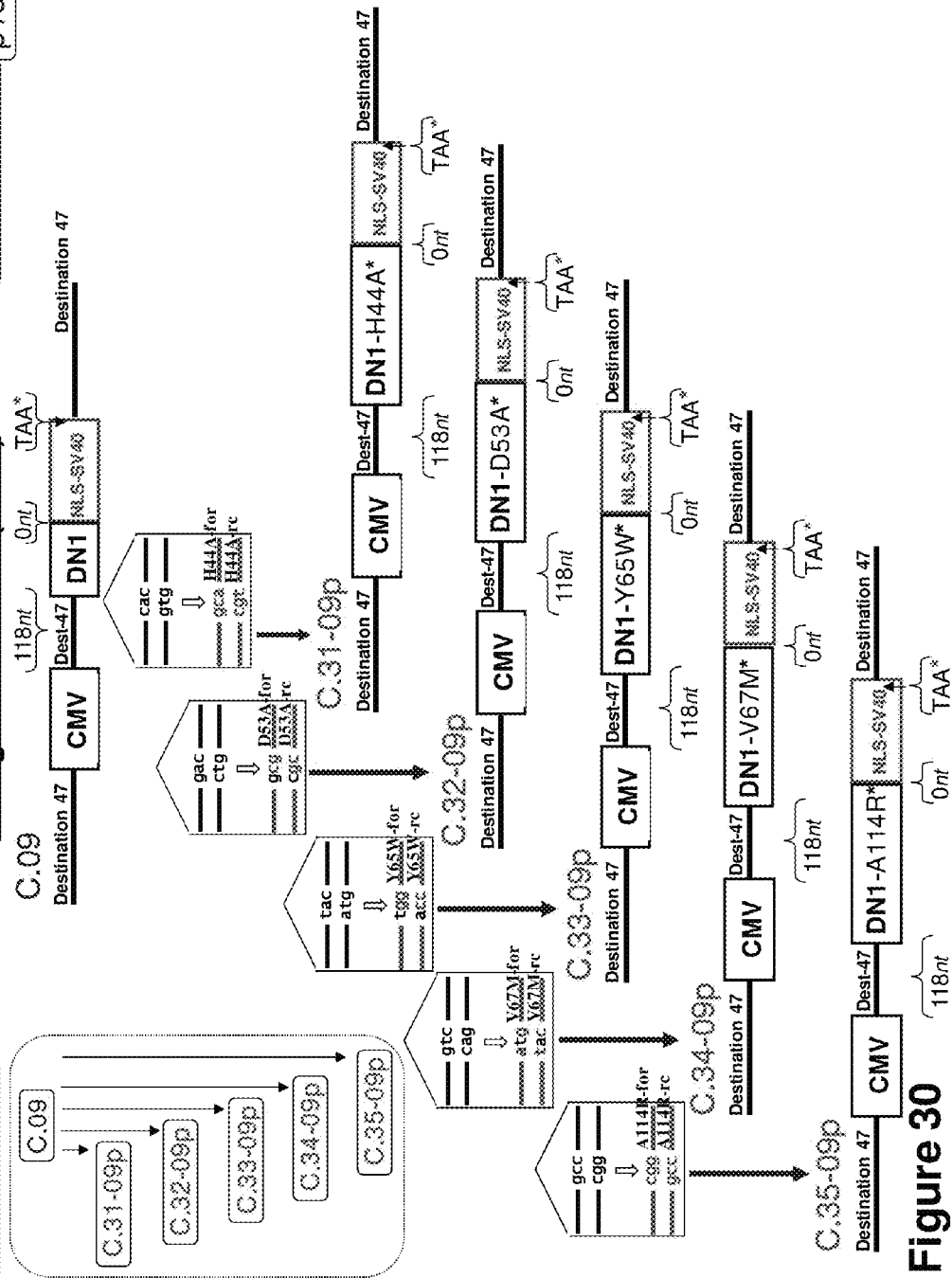
FIG. 30 is a flow chart of mutagenesis sites.

The alanine amino acid was mutated to phenylalanine at position 114 of DNase 1 in C09 using 114 and 114-rc primers to generate C11 (FIGS. 28, 32). Mutations of amino acids at five different actin-binding sites within the DNase-1 gene of C09 were designed, thus, generating five different constructs. The H44A-for/H44A-rc, D53A-for/D53A-rc, Y65W-for/Y65W-rc, V67M-for/V67M-rc, and A114R-for/A114R-rc primers were generated to replace histidine with alanine at position 44, to replace aspartamine with alanine at position 53, to replace tyrosine with alanine at position 65, to replace valine with alanine at position 67, and to replace alanine with arginine at position 114, respectively, in C09. Thus, to generate C31-09p, C32-09p, C33-09p, C34-09p, and C35-09p, constructs (FIGS. 30, 33).

Generation of C18 and C26p, from C11 Construct.

To knock down the enzymatic activity of DNase-1, histidine amino acid was mutated to alanine at position 252 of DNase 1 in C11 using For Primer252HtoA and RevPrimer252HtoA primers, thus, generating C18 (FIGS. 28, 32). To remove the NLS-SV40 from C11 and generate C26p, P9-for-19p6 and P6-rc primers were generated (FIGS. 28, 32, 33).

Generation of C27-26p, C28-26p, C29-26p, and C30-26p, from C26p Construct.

Figure 29:
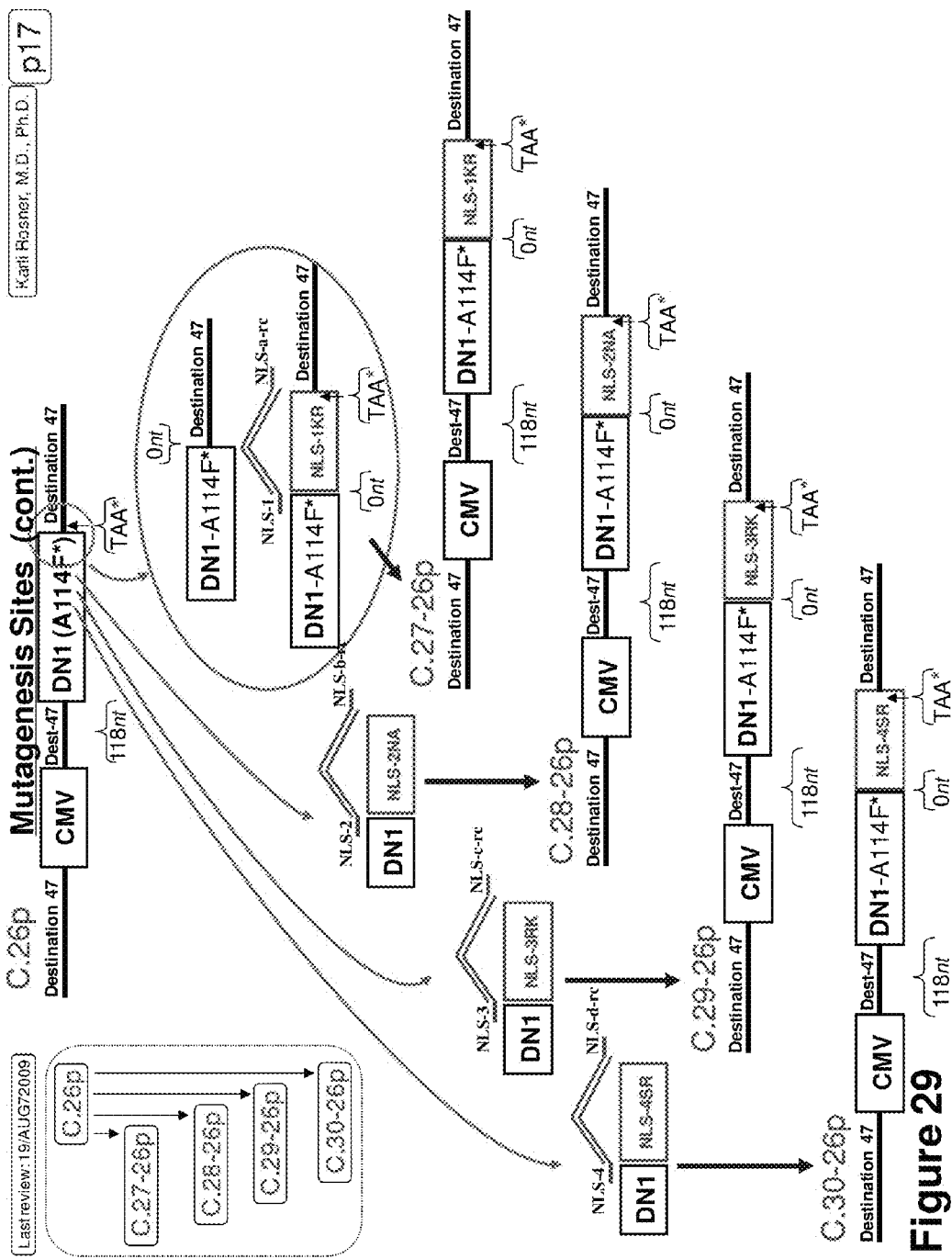
FIG. 29 is a flow chart of mutagenesis sites.

Four different NLSs were designed to be inserted into C26p at the 3'-prime of DNase-1 gene, thus, generating four different constructs. The NLS-1/NLS-a-rc, NLS-2/NLS-b-rc, NLS-3/NLS-c-rc, and NLS-4/NLS-d-rc primers were generated to insert NLS-1KR, NLS-2NA, NLS-3RK, and NLS-4SR, respectively, into C26p. Thus, to generate C27-26p, C28-26p, C29-26p, and C30-26p constructs (FIGS. 29, 33).

Generation of C02 and C06 from C01 Construct.

Figure 22:
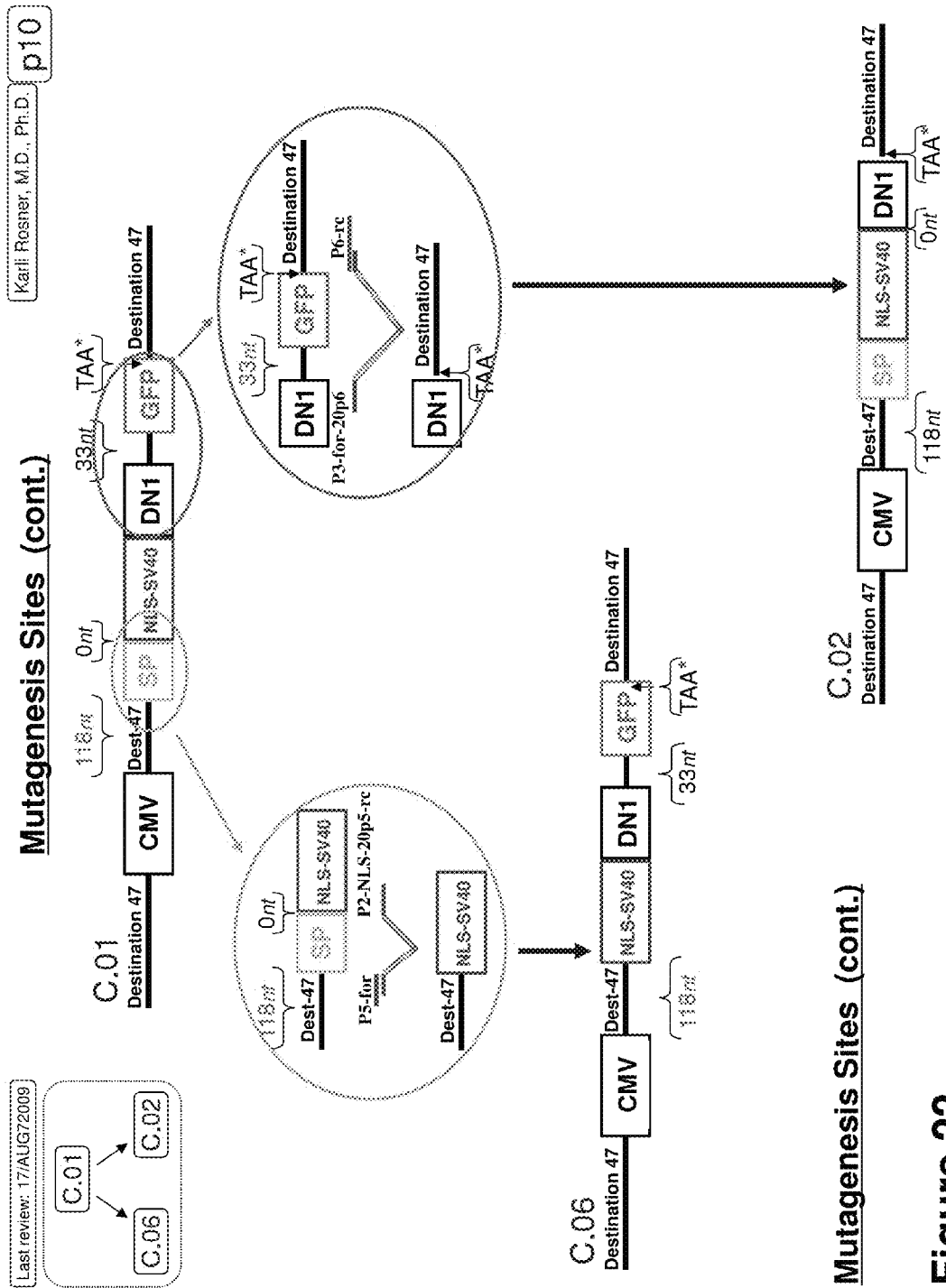
FIG. 22 is a flow chart of mutagenesis sites.

GFP was removed from C01 to generate C02, using P3-for-20p6 and P6-rc primers (FIGS. 22, 32). The signal peptide was removed from C01 to generate C06, using P5-for and P2-NLS-20p5-rc primers (FIGS. 22, 32).

Generation of C12 and C07 from C06 Construct.

Figure 23:
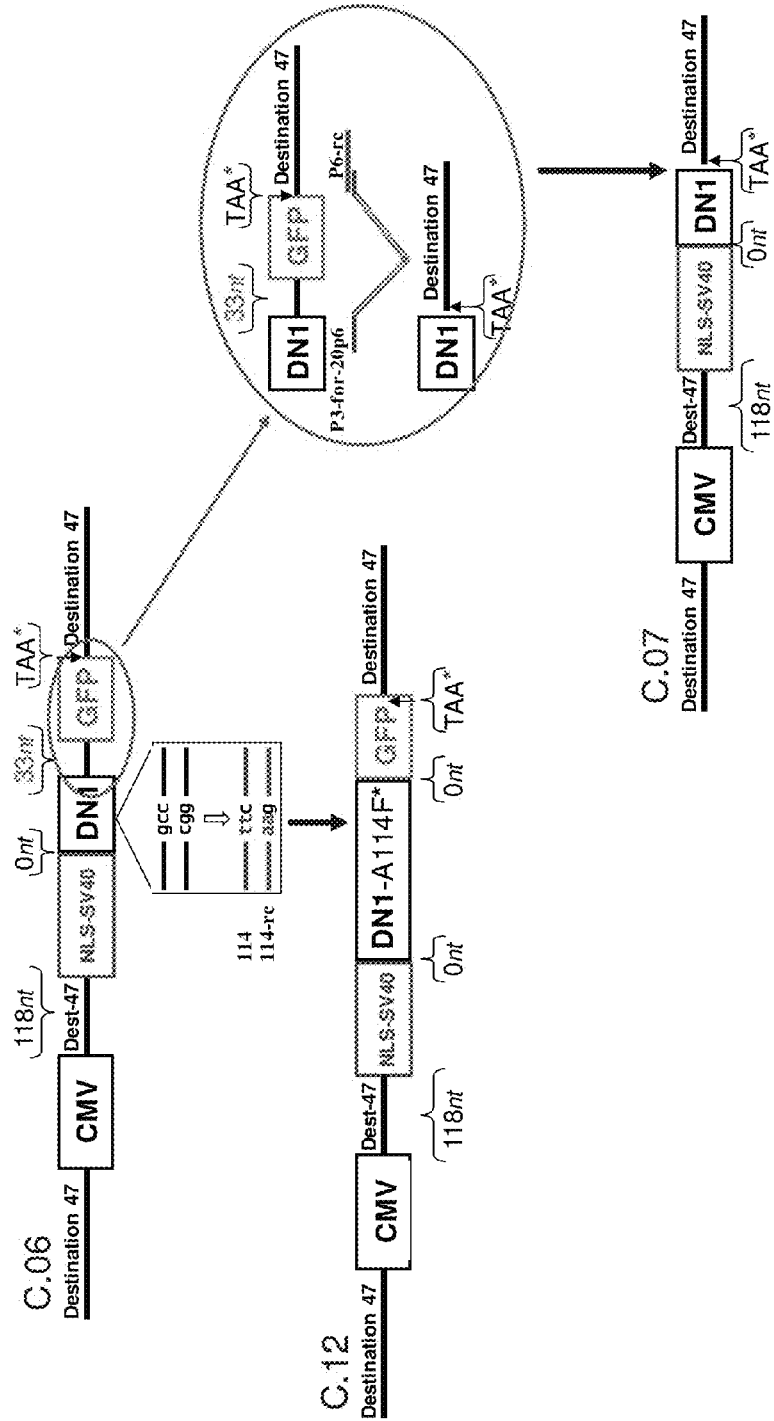
FIG. 23 is a flow chart of mutagenesis sites.

The alanine amino acid was mutated to phenylalanine at position 114 in DNase 1 of C06 using 114 and 114-rc primers to generate C12 (FIGS. 23, 32). GFP was removed from C06 to generate C07, using P3-for-20p6 and P6-rc primers (FIGS. 23, 32).

Generation of C13 from C07 Construct.

Figure 24:
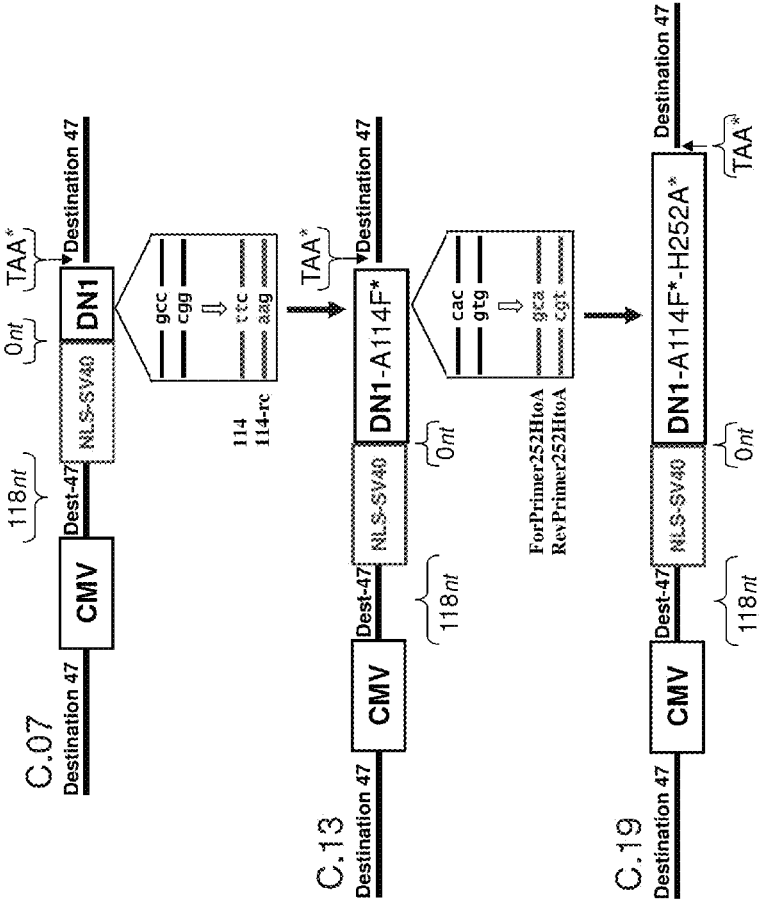
FIG. 24 is a flow chart of mutagenesis sites.

Alanine was mutated to phenylalanine at position 114 in DNase-1 of C07 using 114 and 114-rc primers to generate C13 (FIGS. 24, 32).

Generation of C19 from C13 Construct.

To knock down the enzymatic activity of DNase-1, histidine was mutated to alanine at position 254 in DNase-1 of C13 using For Primer252HtoA and RevPrimer252HtoA primers, thus, generating C19 (FIGS. 24, 32).

Quantitative Real Time Reverse Transcription PCR (QRT-PCR) for RNA Expression.

RNA was extracted from Mel-Juso cells 12 hours, 24 hours, and 36 hours post-transfection using the RNeasy kit (Qiagen, Hilden, Germany) according to the manufacturer's instructions. Quantitative RT-PCR was performed using Taq-Man One-Step RT-PCR Master Mix and probes for DNase 1 (Hs00173736_m1) and Tubulin (Hs00742828_s1) (Applied Biosystems, Foster City, Calif.) and detected with 7300 Real-Time PCR System (Applied Biosystems). For each sample, 1 µg of total RNA was reverse-transcribed at 48° C. for 30 minutes. PCR was performed at 95° C. for 10 minutes, followed by 40 cycles of 95° C. for 15 seconds and 60° C. for 1 minute. The final reaction volume of 50 µL included 1× Master Mix, MultiScribe (0.25 U/µL), RNase Inhibitor Mix (0.4 U/µL), 200 nM of DNase 1 construct, or 200 nM (TUBB) forward (ham F) and reverse (ham R) primers. The relative levels of gene expression of target mRNA was normalized to endogenous TUBB mRNA using the 2-$\Delta\Delta$CT method Experiments were performed three times.

Western Blot.

Cell lysates were collected 12 hours, 24 hours and 36 hours post-transfection with various DNase 1 constructs in 250 µl of 1× Western LDS Sample Buffer (Invitrogen), passed 10 times through a 20-gauge needle and stored at −20° C. until blotting. Electrophoresis of 50 µl protein lysates was conducted through NuPAGE 4%-12% Bis-Tris gels (Invitrogen) and blotted onto a PVDF membrane (FluorTrans, Ann Arbor, Mich.). Membranes were probed with primary anti-DNase-1 antibodies (SC30058; Santa Cruz, Calif.) and Beta-Actin (a5316, Sigma, St. Louis, Mo.), followed by secondary antibodies conjugated to Alexa Fluor 680 (Invitrogen, Eugene, Oreg.) or IR Dye 800 (Rockland, Gilbertsville, Pa.). Bound antibodies were detected at 700 or 800 nm, as indicated, using the Odyssey system (Li-Cor Biosciences, Lincoln, Nebr.).

In Vitro DNase 1 Activity Assay.

DNase 1 variant proteins were synthesized using equal amounts (250 ng) of each variant construct plasmid DNA as a template in an in vitro transcription translation kit (PureExpress, New England Biolabs, Ipswich, Mass.) according to the manufacturer's instructions. As previously demonstrated, DNase 1 activity was determined quantitatively by ELISA (enzyme—linked—immunoabsorbent assay; Orgentec Diagnostika GmbH, Mainz, Germany) according to the manufacturer's instructions. In short, samples were added to a DNA-coated 96 well microplate and incubated for 1 hour at 37° C. Horseradish peroxidase (HRP) conjugated anti-DNase 1 antibodies are added and incubated for 15 minutes at room temperature to react with the remaining uncleaved DNA. The intensity of the color developed during the enzymatic reaction (hydrolysis of HRP-substrate, 3,3',5,5'-tetramethyl-benzidine (TMB) and acid addition) was measured at OD450 using SPECTRAmax GEMINI XS microplate spectrofluorometer (Molecular Devices, Sunnyvale, Calif.). The color intensity in the ELISA assay reflects the amount of remaining intact DNA substrate after exposure to DNase 1. As the catalytic activity of a DNase 1 gene construct increases, less DNA substrate remains intact and the colorimetric level is lower. A standard series, as well as positive and negative controls were included in the kit.

Colony Forming Assay (CFA) for Cell Viability.

Cells were plated in 6 well plates at a density of 600 cells per well. After 24 hours, the cells were transfected with various DNase 1 constructs and controls as described above and allowed to grow for 12-14 days. The cells were then fixed with absolute methanol ethanol for 30 minutes, stained with 1% crystal violet in distilled water, and counted (one colony ≥30 cells). The cells were plated in triplicates and the experiments were repeated five times.

Morphological Assessment of Apoptosis.

Characteristic changes in cell morphology that were used to detect apoptosis include cell membrane blebbing, cytoplasm and nuclear condensation and apoptotic bodies. The morphological changes were visualized by phase contrast microscopy prior to fluorescent microscopy using an Olympus 1×71 Inverted Microscope (Olympus, Centervalley, Pa.).

TUNEL (Terminal Transferase dUTP Nick-End Labeling) Assay for Apoptosis.

Twenty-four hours after the cells were transfected with various DNase 1 constructs and controls as described above, the cells were treated directly in the wells with DeadEnd Fluorometric TUNEL System (Promega, Madison, Wis.) according to the manufacturer's instructions. After fixation with 4% formaldehyde, the cell nuclei were counterstained with Hoechst 33258 (Invitrogen, Eugene, Oreg.) and visualized with a 1×71 Inverted Microscope (Olympus) and Slidebook (ver. 4.2) software (Olympus, Denver, Colo.).

Laser Scanning Cytometry (LSC) for Apoptosis.

Twenty-four hours after the cells were transfected with various DNase 1 constructs and controls as described above, the cells were treated with the DeadEnd Fluorometric TUNEL System (Promega) according to the manufacturer's protocol for detection of apoptotic cells. Cells were counterstained with propidium iodide (PI) as previously described. Fluorescein-TUNEL-positive cells were scanned using an ×20 objective and their numbers were measured by LSC (CompuCyte Corp., Cambridge, Mass., USA). Cells were excited by an argon laser at 488 nm and emitted fluorescence was collected through a 530±30 nm band pass filter (green-FITC/TUNEL) and a 625±28 nm band-pass filter (red-PI). Cell population data were analyzed by WinCyte 3.7 (Compucyte Corp.). The cells were plated in triplicates and at least 2,000 cells were measured per sample.

DNA Fragmentation Assay for Apoptosis.

Twenty-four hours after the cells were transfected with various DNase 1 constructs and controls as described above, the cells were collected and lysed. Genomic DNA was purified using an Apoptotic DNA Ladder Kit (Roche, Mannheim, Germany) according to the manufacturer's instructions. After 20 minutes of treatment with RNase A (200 µg/mL; Invitrogen) the samples were analyzed on a 1% agarose gel supplemented with Syto60 DNA binding dye (Invitrogen, Eugene, Oreg.) and visualized with the Odyssey system (Li-Cor Biosciences, Lincoln, Nebr.).

Statistics.

Data were evaluated graphically and analytically to determine whether a transformation was required to meet the assumptions of the normal theory tests. Colony count, LSC and RT-PCR data required a log transformation while color intensity in ELISA for DNase 1 activity did not. Linear models with robust standard errors were fitted with indicator variables for each of the constructs and for experiment when appropriate. Post-hoc tests were used to compare constructs with adjustment for multiple comparisons made using Holm's procedure.

Results

DNase 1 Gene Construct Compositions and Catalytic Activity

DNase 1 Gene Construct Compositions.

DNase 1 gene constructs were generated by fusing an NLS to either the N-terminus or the C-terminus of the DNase 1 gene and by fusing GFP to the C-terminus directly or downstream to the fused NLS. In addition, mutations were introduced in the DNase 1 gene composition to knockdown DNase 1 protein binding to actin and catalytic activity. The resulting various DNase 1 gene constructs are presented in FIGS. 5A and 5B.

In Vitro DNase Activity Assay.

It was confirmed by in vitro DNase activity assay that all the DNase 1 construct proteins expressed catalytic activity (FIG. 7). Also, it was assessed whether knocking down the activity site of DNase 1 by a histidine to alanine substitution at position 252 resulted in a decreased DNA-degradation activity. The ELISA assay shows that the H252A mutation in actin-resistant DNase 1 gene constructs, C11 and C13, decreased their ability to degrade DNA (C11 vs. C18, $p=0.0005$; C13 vs. C19, $p=0.001$; FIG. 7). No difference in DNA degradation activity was observed between C11 and C13 ($p=0.24$).

All the DNase 1 Gene Constructs were Transcribed to mRNA and Translated to Protein in the Mel-Juso Human Melanoma Cells Quantitated DNase 1 gene Constructs Expression by QRT-PCR for RNA Expression.

It was validated by QRT-PCR that all the tested DNase 1 gene constructs were transcribed to mRNA at all the tested time points; 12 hours, 24 hours, and 36 hours post-transfection (FIG. 6A). With the exception of C13, which at the 24 hour time point had a transcription level below the level of C07 and C19 ($p<0.001$), there was no significant difference in transcription level between the various DNase 1 gene constructs at 12 hours, 24 hours, and 36 hours post-transfection. The relative lower transcription level of C13 as compared to C07 and C19 at 24 hours post-transcription was not reflected in either the protein expression level nor in the cell viability and apoptosis described below.

Western Blot Analysis for Protein Expression.

It was validated by Western blot that all the tested DNase 1 gene constructs were translated to proteins at 12 hours, 24 hours, and 36 hours post-transfection (FIG. 6B). The synthesis of the proteins with an NLS fused to the N-terminus (C07, C13 and C19) was considerably lower than for the proteins with NLS fused to the C-terminus (C09, C11 and C18) (FIG. 6B). Previously, lower DNase 1 protein synthesis was attributed to the elimination of the N-terminus Signal peptide (SP). This is apparently not the case here, as despite lacking the N-terminus SP, the synthesis of C09, C11 and C18 was high (FIG. 6B). It is plausible that structural changes at the N-terminus such as NLS fusion decreased the synthesis efficiency of the protein. Another difference between the N-terminus and C-terminus NLS fused proteins was the detection of one band and two bands, respectively (FIG. 6B). The shift in the band migration and the presence of two bands for DNase 1 were attributed to the extent of glycosylation of the two potential N-glycosylation sites at amino acids 18 and 106. This shows structural interference of NLS fused to the N-terminus in the extent of glycosylation, resulting in only one isoform as compared to two isoforms for proteins fused with NLS to the C-terminus (FIG. 6B).

Localization of DNase 1 Construct After Substitution of the Signal Peptide with a NLS in Melanoma Cells Fluorescence Microscopy Assessment.

The localization of NLS-fused DNase 1 protein constructs within Mel-Juso cells were analyzed 24 hours after transfection, before and after elimination of the SP (FIGS. 8A-8D). Fusion of a NLS to either N-terminus or C-terminus of a SP-DNase 1 did not change the cytoplasmic distribution, as is characteristic for a secretory protein. Only after removal of the SP did the NLS-fused DNase 1 relocate to the nucleus. Images were obtained of strong staining of the nucleus and almost complete depletion of staining from the cytoplasm in multiple experiments with and without Hoechst counterstaining of the nuclei, showing nuclear localization of the NLS-fused DNase 1 constructs regardless of whether the NLS is positioned at the N-terminus or the C-terminus.

Melanoma Cell Survival Decreased Most Profoundly after Treatment with the NLS-Fused and Actin-Resistant DNase 1 Gene Constructs C11 and C13

Colony Forming Assay (CFA).

Neither WT DNase 1 nor C09 or C07 constructs decreased cell survival significantly compared to Cat-GFP control ($p \geq 0.12$). This shows that overexpression of WT DNase 1 is not sufficient to induce cytotoxicity. The results also show that removing the SP from DNase 1 to prevent it from being compartmentalized within the secretory organelles and equipping it with an NLS to gain access to the nucleus are not sufficient to confer cytotoxicity to DNase 1 protein. In contrast, C11 and C13 constructs decreased cell survival to 23.2% and 32.4%, respectively, compared to Cat-GFP control (each $p < 0.0001$). C11 and C13 also decreased cell survival significantly compared to WT DNase 1, C07 or C09 DNase 1 gene constructs (each $p = 0.0003$). There was no difference between C11 and C13 in their potency to reduce cell survival ($p = 0.81$). Taken together with the lack of cytotoxicity by C07 and C09, these results show that the nuclear-targeted DNase 1 is inactivated by actin. Therefore, rendering actin-resistance to the nuclear-targeted DNase 1 is crucial for inducing cytotoxicity. To address the question of whether C11 and C13 induced cytotoxicity directly by their catalytic activity, the H252A substitution was introduced in the catalytic site of DNase 1, generating C18 and C19, respectively. The substitution increased melanoma cell survival from 23.2% (C11) to 61.7% (C18; $p = 0.0003$) and from 32.4% (C13) to 100% (C19; $p = 0.0008$; FIG. 9), showing a direct impact of the DNase 1 constructs on cy Apoptosis of Melanoma Cells was Most Significant after Treatment with the NLS-Fused and Actin-Resistant DNase 1 Gene Constructs C11 and C13

Morphological Assessment and TUNEL Assay for Apoptosis.

Representative examples of characteristic apoptotic morphology and DNA nicking analyzed with phase contrast microscopy and TUNEL assay are presented in FIGS. 10A-10D. Substantial numbers of TUNEL positive cells and cells displaying apoptotic characteristics such as cytoplasm and nuclear condensation and cell membrane blebbing were observed only after treatment with actin-resistant DNase 1 gene constructs, C11 and C13, and only sporadically, due to background apoptosis, after treatment with other DNase 1 gene constructs, Wild-type DNase 1 and controls (FIGS. 10A-10D). Background apoptosis can reflect spontaneous apoptosis that occurs in untreated neoplasms or apoptosis induced by DNA-liposome complexes.

DNA Fragmentation Assay for Apoptosis.

DNA fragmentation was most extensive after treating the melanoma cells with the actin-resistant DNase 1 gene constructs (C11 and C13), reduced after treatment with either C19 or C07, and minute or absent after treatment with C18, C07 or Wild-type DNase 1 (FIG. 11). DNA fragmentation in the form of a smear is characteristic of DNase 1. For inducing the classical DNA laddering form of DNA degradation (low molecular weight DNA fragmentation) DNase 1 requires the removal of DNA binding proteins, which are released during cell damage conditions such as necrosis.

Quantitated Melanoma Cell Apoptosis by Laser Scanning Cytometry for apoptosis.

Laser scanning cytometry (LSC) quantitates cell populations based on their immunofluoresence emission. The quantitated mean and range of positive cells for Cat-GFP, C11, C13 and WT DNase 1 treated populations were 14.2% (9.9-18.6%), 11% (7.3-20.2%), 5.4% (4.0-7.8%) and 1.8% (0.1-2.9%), respectively. As the killing efficiency value reflects the ratio between cells undergoing apoptosis and transfected cell populations, the killing efficiency of C11 is 70-100% and for C13 about 40%. Compared to Mock treated cells, the number of positive cells was significantly higher for the actin-resistant DNase 1 gene constructs (C11 and C13; $p = 0.004$ and $p = 0.03$, respectively), but not for the Wild-type DNase 1 ($p = 0.92$; FIG. 8). Direct comparison to WT DNase 1 demonstrated a significantly higher number of TUNEL-positive cells with the actin-resistant DNase 1 gene constructs having the NLS located on the C-terminus (C11; $p = 0.02$), but not with the actin-resistant DNase 1 gene constructs having the NLS located on the N-terminus (C13; $p = 0.1$). Despite the marginally significant difference, an advantage of C13 over WT DNase 1 in inducing cellular apoptosis is shown by the fact that the lowest value of TUNEL-positive cells induced by C13 (4%) was higher than the highest value of WT DNase 1 (2.9%; FIGS. 12A-12B). Non-actin-resistant DNase 1 gene constructs (C09 and C07), as well as actin-resistant DNase 1 gene constructs with the knocked down activity site (H252A; C18 and C19) triggered apoptosis in only 0.1-0.9%, none of which was significant compared to Mock (each $p > 0.45$; FIGS. 12A-12D).

Discussion

In this study, an approach was pursued of triggering apoptosis in cancer cells without activating the apoptotic-signaling cascade. The signaling cascade can be bypassed by triggering the apoptosis mechanism from the last component, a cell-autonomous nuclease such as CAD or DNase-γ. These endonucleases are characterized by possessing a NLS, which provides free access to the nucleus. It is conceivable that against nuclear targeted endonucleases, the nucleus would employ variable inhibitors, not all of which are known, to prevent premature activation of the apoptotic mechanism and cell death. To bypass these inhibitors and the cancer's defense mechanism of disrupting the apoptotic-signaling cascades, triggering the apoptotic machinery by overexpressing a genetically modified waste-management nuclease, DNase 1, was pursued. In its native form, DNase 1 has no access to the intact nucleus and has only one known major cellular inhibitor, actin.

The Mel-Juso cell line was chosen due to its high resistance to apoptosis, which makes it a good choice for testing the killing efficiency of pro-apoptotic therapies. This cell line is chemoresistant, displays higher resistance to UVB induced apoptosis than other melanoma cell lines, and is not sensitive to Fas or TRAIL induced apoptosis. The apoptosis-resistance of Mel-Juso results from multiple molecular changes such as mutations in the pro-apoptotic RAS gene or overexpression of the strong anti-apoptotic Bcl-xL, a member of the Bcl-2 family.

Overexpression of Wild Type Dnase 1 was not Sufficient to Induce Apoptosis.

It was demonstrated that overexpression of a full length DNase 1 cDNA with a N-terminus Signal peptide did not decrease melanoma cell survival (FIG. 9). Also, it did not increase the number of cells undergoing apoptosis as assessed by TUNEL assay and measured by LSC (FIGS. 12A-12B), nor did it result in DNA degradation greater than in controls (FIG. 11). The observations are in contrast to a previous report that overexpression of WT DNase 1 alone was sufficient to trigger apoptosis in COS-cells. In that study, DNA from nuclei isolated from transfected cells demonstrated multiples of 200 bp fragments. It is hard to reconcile the study's claim that the overexpressed WT DNase 1 could enter the nucleus and trigger apoptosis by cleaving the DNA with DNase 1's features of possessing a SP and lacking a NLS, both of which deny WT DNase 1 access to the nucleus. A possible explanation could be contamination of the nuclear extract with DNase 1 from intracellular storage (nuclear envelope, ER, Golgi apparatus or secretory vesicles). The possibility of contamination is supported by the study's classic intranucleosomal-DNA fragmentation of 200 bp fragments, which is typically not generated by DNase 1 nucleolysis unless it is associated with proteolysis by proteins released from lysosomes. Moreover, in a similar previous study of COS-cells, the same group claimed that the overexpressed WT DNase 1 gained access to the nucleus after both the nuclear envelope and the ER broke down. Hence, the overexpressed WT DNase 1 did not trigger apoptosis but joined the process as a late player. In contrast, the findings herein are supported by studies showing that an overexpressed DNase 1, having a N-terminus Signal peptide, does not localize to the nuclei of NIH-3T3 cells nor does it produce DNA fragmentation in C2C12 cells.

Removing the Signal Peptide (SP) and Adding a Nuclear Localization Signal (NLS) are Not Sufficient to Render DNase 1 the Ability to Induce Apoptosis The SP directs the synthesized DNase 1 enzyme away from the nucleus to be either secreted out of the cell or to be compartmentalized in the Golgi apparatus and the secretory vesicles. It was found that as long as the SP is present, a NLS will fail to target DNase 1 to the nucleus (FIGS. 8A-8D). Therefore, it was conceivable that elimination of the SP and adding a NLS would gain DNase 1 access to the nucleus and the opportunity to defragment the genomic DNA. To test this notion, the C07 and C09 DNase 1 constructs were generated having the NLS fused to DNase 1's N-terminus and C-terminus, respectively. However, it was found that overexpression of the modified DNase 1 cDNA (C07 and C09) did not decrease melanoma cell survival (FIG. 9) nor did it increase the number of cells undergoing apoptosis as assessed by TUNEL assay and measured by LSC (FIGS. 12A-12B). C09 showed no chromatin-degrading effect greater than controls, while the C07 construct displayed a limited chromatin-degrading effect compared to C11 and C13. Taken together, the results herein show that replacing the SP with a NLS is not sufficient to enable DNase 1 to trigger apoptosis significantly enough to reduce cell survival. As C07 and C09 did not differ in their impact on cell viability and LSC quantitated apoptosis, the inability of the modified DNase 1 to induce apoptosis cannot be attributed to the N-terminus or C-terminus NLS fusion. Removal of the SP from the DNase 1 protein can impact the extent of glycosylation at the amino acid 18 and 106 sites. Also, the extent of glycosylation cannot explain the failure of the modified DNase 1 to trigger apoptosis since glycosylation is not required for DNase 1 activity. Elimination of the SP was reported to result in a cytoplasmic distribution and nuclear accumulation of WT DNase 1 fused with GFP. However, in that report the authors acknowledged that the GFP degradation product, which was present in all the study's transfections, could have compromised the immunofluorescence localization studies.

Overexpression of a DNase 1 Gene Construct that Include the Combination of Three Modifications Mutated Binding to Actin, Deleted Signal peptide (SP) and Addition of a Nuclear Localization Signal (NLS), Successfully Triggered Apoptosis in Human Melanoma Cells The nucleus, as does the cytoplasm, contains abundant amounts of actin, which is the major natural inhibitor of DNase 1. Therefore, it was hypothesized that nuclear actin inhibited the activity of the NLS fused DNase 1 constructs, C07 and C09. To test this hypothesis, DNase 1's binding site (A114F) in C07 and C09 was mutated, thus, generating actin-resistant DNase 1 constructs, C13 and C11, respectively. A114F substitution is reported to increase the potency of WT DNase 1 by ~5-fold. The generated actin-resistant C11 and C13 DNase 1 constructs comprise three genetic alterations: (i) eliminated SP, (ii) fused NLS, and (iii) mutation of actin-binding site. C11 and C13 significantly decreased melanoma cell survival (FIG. 9), induced characteristic apoptotic morphological changes (FIGS. 10A-10D), increased the number of cells undergoing apoptosis as assessed by TUNEL assay and measured by LSC (FIGS. 12A-12B), and induced DNA-degradation (FIG. 11). Quantitated apoptosis assessment (FIGS. 12A-12B) showed an advantage over WT DNase 1 to be significant for C11 and only marginally significant for C13. However, even the lowest value of TUNEL-positive cells induced by C13 (4%) was higher than the highest value of WT DNase 1 (2.9%). The difference between C11 and C13 in the extent of induced apoptosis could be explained by the lower C13 synthesis (FIG. 6B) or alternatively, by a steric effect of the fused NLS to the N-terminus that could compromise the activity site. These findings show that C11 and C13 DNase 1 constructs comprised the best combination of genetic modifications for overcoming the melanoma cell defense mechanisms against premature death by apoptosis. In addition, these findings show that nuclear actin plays a protective-role against DNase 1 and accidental death, as does cytoplasmic actin. The findings herein do not exclude the possibility of inducing apoptosis with a non-actin-resistant DNase 1 targeted to the nucleus by an NLS after SP removal. It is plausible that this could occur in cells expressing low G-actin levels due to the cells state of differentiation or the characteristics of a particular cell type. However, conferring actin resistance to DNase 1 provides the advantage of successfully treating previously treatment-resistant cancers that express high actin-G content, as do the human melanoma cells that were affected only by the actin-resistant NLS-fused DNase 1.

It is noteworthy that constructs having the A114F mutation, which were only partially resistant to actin inhibition, were extremely efficient inducers of apoptosis. This indicates that gene constructs having incomplete resistance to an inhibitor can nonetheless produce significant apoptosis when directed to the nucleus. In the case of actin binding, incomplete resistance can be conferred by knocking out less than all actin-binding sites, or by only partially inhibiting actin binding sites. The findings also indicate that the cell-killing efficiency of genetically-modified DNA-degrading enzymes, that have binding sites for inhibitors other than actin, can be increased by engineering suitable mutations of those inhibitor binding sites.

Next, it was investigated whether DNase 1 constructs triggered apoptosis directly using their catalytic activity or indirectly through mediators. One of DNase 1's two catalytic sites were mutated, H252A, in C11 and C13, generating DNase 1 constructs C18 and C19, respectively. This substitution is reported to decrease WT DNase 1 activity by ~10-fold. Knocking down the activity site resulted in full restoration of cell survival (FIG. 9), decline in the number of apoptotic cells to the background of controls (FIGS. 8A-8B), and a chromatin-degrading effect, which was reduced completely for C18 and partially for C19 (FIG. 11). These findings show that C11 and C13 triggered apoptosis by direct cleavage of the genomic DNA through their catalytic site.

Killing Efficiency of Actin Resistant DNase 1 Constructs Fused with NLS and Lacking a SP Next, the killing efficiency of C11 and C13 DNase 1 constructs using LSC was assessed, which provides a quantitative analysis of TUNEL positive cells. LSC measured a Cat-GFP cell population, representing transfection efficiency, of 10-20%. The TUNEL positive cell population after C11 construct treatment was 7-21% and after C13 treatment 4-8%. The ratio of cells undergoing apoptosis to the transfection cells show a killing efficiency of 70-100% for C11 and ~40% for C13. As previously mentioned, the lower killing efficiency of C13 can reflect lower protein synthesis or reduced catalytic activity due to the N-terminus fusion of the NLS (FIG. 6B) due to fusion of NLS to the N-terminus of DNase 1. Nevertheless, the high killing efficiency of the C11 construct indicates that deleting the N-terminus SP and adding a C-terminus NLS to an actin-resistant DNase 1 provided the most effective combination of genetic modifications.

The population of cells undergoing apoptosis (TUNEL-positive) was not larger than the transfected cell population (Cat-GFP positive; ≤1). This shows lack of the 'bystander effect' characterizing HSV-tk, the most investigated mode of suicide gene therapy. HSV-tk relays heavily on the 'bystander effect', which in addition to killing GCV-treated HSV-tk transduced cells, also leads to the killing of a large number of neighboring non-transduced cancer cells. The 'bystander effect' is associated with the side-effect of killing normal cells such as human ovarian epithelial cells and lens epithelial cells. Moreover, HSV-tk treatment led to the killing of 9 of 19 rats treated for hepatocellular carcinoma. Therefore, a lack of a 'bystander effect' for the DNase 1 gene therapy, if confirmed by further studies, would provide a substantial safety advantage adding to its high killing efficiency for treatment resistant cancers such as melanoma.

Low transfection efficiencies by the conventional transfection procedures, such as displayed in the LSC assay, compromised the ability of implementing gene therapy methods successfully for the last two decades. Recently, the transfection efficiencies improved to more than 95% with a new generation of vectors such as lentiviruses. This is particularly promising for medical implementation of high-killing efficiency methods such as the presented DNase 1 gene constructs anti-cancer approach once selective cell targeting is also secured.

In Summary

It has been shown herein that a waste-management enzyme can be genetically modified to bypass cancer's anti-apoptotic defense mechanism and to trigger apoptosis in human melanoma cells without a pharmacological adjuvant. Hr DNase 1 gene constructs and constructs encoding other DNA-degrading enzymes have potential application in vivo application to a variety of treatment-resistant cancers.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES CITED

Ben-Yehudah A, Aqeilan R, Robashkevich D, Lorberboum-Galski H., Using apoptosis for targeted cancer therapy by a new gonadotropin releasing hormone-DNA fragmentation factor 40 chimeric protein. Clin Cancer Res 2003, 9:1179-90.

Boone D L, Tsang B K., Identification and localization of deoxyribonuclease I in the rat ovary. Biol Reprod 1997, 57:813-21.

Harrop R, John J, Carroll M W., Recombinant viral vectors: cancer vaccines. Adv Drug Deliv Rev. 2006, 58:931-47.

Higami Y, Tsuchiya T, To K, Chiba T, Yamaza H, Shiokawa D, Tanuma S, Shimokawa I., Expression of DNase gamma during Fas-independent apoptotic DNA fragmentation in rodent hepatocytes. 2004, 316: 403-7.

Lechardeur D, Drzymala L, Sharma M, Zylka D, Kinach R, Pacia J, Hicks C, Usmani N, Rommens J M, Lukacs G L., Determinants of the nuclear localization of the heterodimeric DNA fragmentation factor (ICAD/CAD). J Cell Biol 2000, 150:321-4.

Lichtenstein M, Ben-Yehudah A, Belostotsky R, Eaveri R, Sabag O, Grodzovski I, Lorberboum-Galski H., Utilizing a GnRH-based chimeric protein for the detection of adenocarcinoma. Int J Oncol 2005, 27:143-8.

Linardou H, Epenetos A A, Deonarain M P., A recombinant cytotoxic chimera based on mammalian deoxyribonuclease-I. Int J Cancer, 2000, 86:561-9.

Mizuta R, Mizuta M, Araki S, Shiokawa D, Tanuma S, Kitamura D., Action of apoptotic endonuclease DNase gamma on naked DNA and chromatin substrates. Biochem Biophys Res Commun. 2006, 345:560-7.

Napirei M, Wulf S, Eulitz D, Mannherz H G, Kloeckl T., Comparative characterization of rat deoxyribonuclease 1 (Dnase1) and murine deoxyribonuclease 1-like 3 (Dnase1l3). Biochem J 2005, 389: 355-64.

Oliveri M, Daga A, Cantoni C, Lunardi C, Millo R, Puccetti A., DNase I mediates internucleosomal DNA degradation in human cells undergoing drug-induced apoptosis. Eur J Immunol 2001, 31:743-51.

Pan C Q, Dodge T H, Baker D L, Prince W S, Sinicropi D V, Lazarus R A., Improved potency of hyperactive and actin-resistant human DNase I variants for treatment of cystic fibrosis and systemic lupus erythematosus. J Biol Chem 1998, 273:18374-81.

Peitsch M C, Polzar B, Stephan H, Crompton T, MacDonald H R, Mannherz H G, Tschopp J., Characterization of the endogenous deoxyribonuclease involved in nuclear DNA degradation during apoptosis (programmed cell death). EMBO J 1993, 12:371-7; 1993.

Polzar B, Peitsch M C, Loos R, Tschopp J, Mannherz H G., Overexpression of deoxyribonuclease I (DNase I) transfected into COS-cells: its distribution during apoptotic cell death. Eur J Cell Biol 1993, 62:397-405.

Roth J C, Curiel D T, Pereboeva L. Cell vehicle targeting strategies. Gene Ther. 2008 May; 15(10):716-29

Saito R, Mizuno M, Kumabe T, Yoshimoto T, Tanuma S, Yoshida J. Apoptotic DNA endonuclease (DNase-gamma) gene transfer induces cell death accompanying DNA fragmentation in human glioma cells. J Neuro-Oncol 2003, 63:25-31.

Shiokawa D, Shika Y, Tanuma S., Identification of two functional nuclear localization signals in DNase gamma and their roles in its apoptotic DNase activity. Biochem J 2003, 376:377-81.

Sunaga S, Yoshimori A, Shiokawa D, Tanuma S., Structure basis for the inhibitory mechanism of a novel DNase gamma-specific inhibitor, DR396. Bioorg Med. Chem. 2006, 14:4217-26.

Ulmer J S, Herzka A, Toy K J, Baker D L, Dodge A H, Sinicropi D, Shak S, Lazarus R A., Engineering actin-resistant human DNase I for treatment of cystic fibrosis. PNAS 1996, 93:8225-9.

Vassaux G, Nitcheu J, Jezzard S, Lemoine N R. Bacterial gene therapy strategies. J Pathol. 2006 208:290-8.

Walther W, Stein U, Viral Vectors for Gene Transfer: A Review of Their Use in the Treatment of Human Diseases. Drugs 2000, 60:249-71.

---

What is claimed is:

1. A gene construct comprising a nucleotide sequence encoding a DNAse 1 protein operatively linked to a nucleotide sequence encoding a nuclear localization signal (NLS), wherein said nucleotide sequence encoding said DNAse 1 protein includes at least one mutation rendering an actin binding site of said DNAse 1 protein resistant to the binding of actin, said gene construct lacking the nucleotide sequence encoding a secretion signal peptide, said gene construct additionally including at least one promoter operatively linked to said nucleotide sequence encoding said DNAse 1 protein and to said nucleotide sequence encoding said NLS.

2. The gene construct of claim 1, wherein said at least one promoter is chosen from the group consisting of the promoter from the prostate-specific antigen (PSA) gene; the promoter from the prostate-specific membrane antigen (PSMA) gene; the promoter from the prostatic acid phosphatase (PAP) gene; the probasin promoter ARR2PB; the promoter from the human secretoglobin family 2A member 2 (hSCGB2A2) gene; the promoter from the DF3/MUC1 gene; the promoter from the thyroglobulin gene; the promoter from the calcitonin (CT) gene; a nucleotide encoding the TTF1 gene operatively linked to a promoter of the human telomerase reverse transcriptase (hTERT) gene and to 5 tandem copies of at least a portion of a nucleotide encoding the human signal-induced proliferation-associated gene 1 (hSPA1); the promoter from the hexokinase II gene; the promoter from the phosphoenolpyrovate carboxykinase gene; the promoter from the albumin gene; the promoter RIP from the rat insulin gene; the promoter from the GFAP gene; the promoter from the gametophytic factor 2 (gfa2) gene; the promoter from the neuron specific enolase (NSE) gene; the 2nd intron of the Nestin gene operatively linked upstream to the 5' upstream region (2iNP) of the Nestin gene; the promoter from the HLA-Dr alpha gene; the promoter from the CD4 gene; the promoter from the CD19 gene; the promoter from the Ig kappa gene; the long terminal repeat (LTR) promoter of HIV-1; and the promoter from cytomegalovirus (CMV).

3. The gene construct of claim 1, wherein said nuclear localization signal is chosen from the group consisting of SEQ ID NO: 1, SEQ ID NO: 2, SEQ ID NO: 3, SEQ ID NO: 4, and SEQ ID NO: 5.

4. The gene construct of claim 1, wherein said at least one promoter is a melanocyte-specific promoter.

5. The gene construct of claim 4, wherein said melanocyte-specific promoter is chosen from the group consisting of the promoter from the tyrosinase gene, the promoter from the melanoma inhibitory activity (MIA) gene, the promoter from the SILV/PMEL17/GP100 gene, the promoter from the Melan-A/MART-1 gene, the promoter from the melanocortin-1 receptor (MC1R) gene, and the promoter from the microphthalmia-associated transcription factor (MITF) gene.

6. The gene construct of claim 1 or claim 4, additionally including an enhancer operatively linked to said promoter, said enhancer being chosen from the group consisting of the enhancer of the PSA gene, operatively linked to a rat probasin promoter; the 1455 bp PSA enhancer; the prostate-specific chimeric enhancer PSES; and the enhancer of the DF3/MUC1 gene, said enhancer of said DF3/MUC1 gene operatively linked to the promoter from said DF3/MUC1 gene.

7. The gene construct of claim 1, additionally including, operatively linked to said nucleotide sequence encoding said DNAse 1 protein and to said nucleotide sequence encoding said NLS, an activator binding sequence, and said gene construct including a nucleotide sequence encoding an inducible transcriptional activator system chosen from the group consisting of a transcriptional activator system inducible by an antibiotic, and a transcriptional activator system inducible by radiation.

8. The gene construct of claim 7 additionally including a promoter operatively linked to said gene construct encoding an inducible transcriptional activator system.

9. The gene construct of claim 1, wherein said actin-resistant binding site is an actin binding site including a mutation chosen from the group consisting of Glu-13, His-44, Asp-53, Tyr-65, Val-66, Val-67, Glu-69, Ala-114, and combinations thereof.

10. The gene construct of claim 1, additionally including, operatively linked to said nucleotide sequence encoding said DNAse 1 protein and to said nucleotide sequence encoding said NLS, a nucleotide sequence encoding the translation regulator Musashi.

* * * * *

SEQUENCE LISTING

```
<160> NUMBER OF SEQ ID NOS: 55

<210> SEQ ID NO 1
<211> LENGTH: 8
<212> TYPE: PRT
<213> ORGANISM: Simian virus 40

<400> SEQUENCE: 1

Pro Pro Lys Lys Lys Arg Lys Val
1               5

<210> SEQ ID NO 2
<211> LENGTH: 17
<212> TYPE: PRT
<213> ORGANISM: Xenopus laevis

<400> SEQUENCE: 2

Lys Arg Pro Ala Ala Thr Lys Lys Ala Gly Gln Ala Lys Lys Lys Lys
1               5                   10                  15

Leu

<210> SEQ ID NO 3
<211> LENGTH: 11
<212> TYPE: PRT
<213> ORGANISM: Unknown
<220> FEATURE:
<223> OTHER INFORMATION: nuclear localization sequence

<400> SEQUENCE: 3

Asn Ala Pro Arg Gly Lys Lys Pro Ala Pro Gly
1               5                   10

<210> SEQ ID NO 4
<211> LENGTH: 9
<212> TYPE: PRT
<213> ORGANISM: Homo sapiens
```

```
<400> SEQUENCE: 4

Arg Lys Phe Lys Lys Lys Phe Asn Lys
1               5

<210> SEQ ID NO 5
<211> LENGTH: 7
<212> TYPE: PRT
<213> ORGANISM: Unknown
<220> FEATURE:
<223> OTHER INFORMATION: nuclear localization sequence

<400> SEQUENCE: 5

Ser Arg Lys Arg Pro Arg Pro
1               5

<210> SEQ ID NO 6
<211> LENGTH: 2055
<212> TYPE: DNA
<213> ORGANISM: Homo sapiens
<220> FEATURE:
<221> NAME/KEY: misc_structure
<222> LOCATION: (1064)..(1066)
<223> OTHER INFORMATION: start codon
<220> FEATURE:
<221> NAME/KEY: sig_peptide
<222> LOCATION: (1067)..(1129)
<220> FEATURE:
<221> NAME/KEY: gene
<222> LOCATION: (1130)..(1909)
<223> OTHER INFORMATION: DNase-1
<220> FEATURE:
<221> NAME/KEY: misc_structure
<222> LOCATION: (1910)..(1912)
<223> OTHER INFORMATION: stop codon

<400> SEQUENCE: 6
```

| | | | | | |
|---|---|---|---|---|---|
| ccatagtctt | agctactcag | gaggctgagg | agggaggatt | atctgagccc | tggcggttga | 60 |
| ggctataatg | agccatgatt | gtgccactgc | actccagcct | ggcaacaca | gtgtgagacc | 120 |
| ctgtctcaaa | aacaataaaa | acccaaaaca | aaagaaccaa | gaaattactg | gacctgaggc | 180 |
| ctggccttta | gctgctgccc | tgcccttgtg | acctggtcac | tcgggatccc | ctgggcctaa | 240 |
| acacacagcc | tattgtctac | ctcaagaagg | ctccccactg | cttggctggc | aattgggtg | 300 |
| ggctttgcag | gccccacctg | tcctgtcccc | acggcgctgg | tgctgcaggc | ccccaccact | 360 |
| gcttgttccg | agctccccca | gcctcctgca | gagttgcctg | cacctgatgg | cgatgaatca | 420 |
| ggaaggcagg | cgtgtcctgg | gccacagagc | agtcatggct | gtcagccacc | aggggctcc | 480 |
| atttgcacct | ttggatgtgg | ctttggcctc | tttgtccaaa | gtgaccttgg | ggcccccaga | 540 |
| caagagacag | ggagactgga | gcccagtccc | accctcccgc | acatacctgg | cccatccctg | 600 |
| ccctatcctg | gaagatgggg | gccaccacac | gtgcaaggga | cacggatag | gaaccctttgg | 660 |
| ccttgttatc | agacatttta | aaactaagtg | caaacgtgat | tatcaggtgc | agttttaca | 720 |
| gcagcaagaa | acctgtgctt | acagaaagaa | acacgtgcta | gcaacccacc | tatgcggaaa | 780 |
| gccacacaga | gccattgttt | tctgcactct | caggtgacgg | ctcacatttg | ccccagggaa | 840 |
| ggtcacagct | gcctgaactt | ttaaaactcc | cagacacgca | ctgcctgtgc | aggatccgga | 900 |
| gcccagcagc | actgccagtg | ccttgaagtg | cttcttcaga | gacctttctt | catagactac | 960 |
| tttttttct | ttaagcagca | aaaggagaaa | attgtcatca | aaggatattc | cagattcttg | 1020 |
| acagcattct | cgtcatctct | gaggacatca | ccatcatctc | aggatgaggg | gcatgaagct | 1080 |
| gctgggggcg | ctgctggcac | tggcggccct | actgcagggg | gccgtgtccc | tgaagatcgc | 1140 |

```
agccttcaac atccagacat tggggagac caagatgtcc aatgccaccc tcgtcagcta      1200
cattgtgcag atcctgagcc gctatgacat cgccctggtc caggaggtca gagacagcca      1260
cctgactgcc gtggggaagc tgctggacaa cctcaatcag gatgcaccag acacctatca      1320
ctacgtggtc agtgagccac tgggacggaa cagctataag gagcgctacc tgttcgtgta      1380
caggcctgac caggtgtctg cggtggacag ctactactac gatgatggct gcgagccctg      1440
cgggaacgac accttcaacc gagagccagc cattgtcagg ttcttctccc ggttcacaga      1500
ggtcagggag tttgccattg ttcccctgca tgcggccccg ggggacgcag tagccgagat      1560
cgacgctctc tatgacgtct acctggatgt ccaagagaaa tggggcttgg aggacgtcat      1620
gttgatgggc gacttcaatg cgggctgcag ctatgtgaga ccctcccagt ggtcatccat      1680
ccgcctgtgg acaagcccca ccttccagtg gctgatcccc gacagcgctg acaccacagc      1740
tacacccacg cactgtgcct atgacaggat cgtggttgca gggatgctgc tccgaggcgc      1800
cgttgttccc gactcggctc ttccctttaa cttccaggct gcctatgcc tgagtgacca      1860 actggcccaa gccatcagtg accactatcc agtggaggtg atgctgaagt gagcagcccc      1920
ctccccacac cagttgaact gcaggaagag aggacccatc ctgccacagg acccagaaaa      1980
aaagcccaac acacactcgg gttaagaaat acctttaaat ttaggtaaat aaagctcaag      2040
gaggtggggc tgtca                                                       2055

<210> SEQ ID NO 7
<211> LENGTH: 46
<212> TYPE: DNA
<213> ORGANISM: Artificial Sequence
<220> FEATURE:
<223> OTHER INFORMATION: Primer 114

<400> SEQUENCE: 7
cgacaccttc aaccgagagc cattcattgt caggttcttc tcccgg                      46

<210> SEQ ID NO 8
<211> LENGTH: 46
<212> TYPE: DNA
<213> ORGANISM: Artificial Sequence
<220> FEATURE:
<223> OTHER INFORMATION: Primer 114-rc

<400> SEQUENCE: 8
ccgggagaag aacctgacaa tgaatggctc tcggttgaag gtgtcg                      46

<210> SEQ ID NO 9
<211> LENGTH: 55
<212> TYPE: DNA
<213> ORGANISM: Artificial Sequence
<220> FEATURE:
<223> OTHER INFORMATION: Primer ForPrimer252HtoA

<400> SEQUENCE: 9
ggcccaagcc atcagtgacg catatccagt ggaggtgatg ctgaagtgcc cgccg           55

<210> SEQ ID NO 10
<211> LENGTH: 55
<212> TYPE: DNA
<213> ORGANISM: Artificial Sequence
<220> FEATURE:
<223> OTHER INFORMATION: P1-NLS-for

<400> SEQUENCE: 10
actggcggcc ctactgcagg gggccgtgtc cccgccgaaa agaaacgca aagtg            55
```

<210> SEQ ID NO 11
<211> LENGTH: 62
<212> TYPE: DNA
<213> ORGANISM: Artificial Sequence
<220> FEATURE:
<223> OTHER INFORMATION: P2-20p5-rc

<400> SEQUENCE: 11
ggtctcccca aatgtctgga tgttgaaggc tgcgatcttc agcatgccag cttttttgta    60
ca                                                                   62

<210> SEQ ID NO 12
<211> LENGTH: 86
<212> TYPE: DNA
<213> ORGANISM: Artificial Sequence
<220> FEATURE:
<223> OTHER INFORMATION: P2-NLS-20p5-rc

<400> SEQUENCE: 12
ggtctcccca aatgtctgga tgttgaaggc tgcgatcttc agcactttgc gtttcttttt    60
cggcggcatg ccagcttttt tgtaca                                         86

<210> SEQ ID NO 13
<211> LENGTH: 66
<212> TYPE: DNA
<213> ORGANISM: Artificial Sequence
<220> FEATURE:
<223> OTHER INFORMATION: P2-NLS-rc

<400> SEQUENCE: 13
ggtctcccca aatgtctgga tgttgaaggc tgcgatcttc agcactttgc gtttcttttt    60
cggcgg                                                               66

<210> SEQ ID NO 14
<211> LENGTH: 66
<212> TYPE: DNA
<213> ORGANISM: Artificial Sequence
<220> FEATURE:
<223> OTHER INFORMATION: P3-for-20p6

<400> SEQUENCE: 14
ccaagccatc agtgaccact atccagtgga ggtgatgctg aagtgctaat gaattaaacc    60
cgctga                                                               66

<210> SEQ ID NO 15
<211> LENGTH: 70
<212> TYPE: DNA
<213> ORGANISM: Artificial Sequence
<220> FEATURE:
<223> OTHER INFORMATION: P3-NLS-for

<400> SEQUENCE: 15
ccaagccatc agtgaccact atccagtgga ggtgatgctg aagtgcccgc cgaaaaagaa    60
acgcaaagtg                                                           70

<210> SEQ ID NO 16
<211> LENGTH: 77
<212> TYPE: DNA
<213> ORGANISM: Artificial Sequence
<220> FEATURE:
<223> OTHER INFORMATION: P4-NLS-rc

<400> SEQUENCE: 16
tcaacaagaa ttgggacaac tccagtgaaa agttcttctc ctttgctagc catcactttg    60
cgtttctttt tcggcgg                                                    77

<210> SEQ ID NO 17
<211> LENGTH: 57
<212> TYPE: DNA
<213> ORGANISM: Artificial Sequence
<220> FEATURE:
<223> OTHER INFORMATION: P5-for

<400> SEQUENCE: 17
gacccaagct ggctagttaa gcttgatcaa acaagtttgt acaaaaaagc tggcatg       57

<210> SEQ ID NO 18
<211> LENGTH: 72
<212> TYPE: DNA
<213> ORGANISM: Artificial Sequence
<220> FEATURE:
<223> OTHER INFORMATION: P6-NLS-rc

<400> SEQUENCE: 18
ggcaactaga aggcacagtc gaggctgatc agcgggttta attcattaca ctttgcgttt    60 cttttttcggc gg                                                        72

<210> SEQ ID NO 19
<211> LENGTH: 48
<212> TYPE: DNA
<213> ORGANISM: Artificial Sequence
<220> FEATURE:
<223> OTHER INFORMATION: P6-rc

<400> SEQUENCE: 19
ggcaactaga aggcacagtc gaggctgatc agcgggttta attcatta                 48

<210> SEQ ID NO 20
<211> LENGTH: 55
<212> TYPE: DNA
<213> ORGANISM: Artificial Sequence
<220> FEATURE:
<223> OTHER INFORMATION: RevPrimer252HtoA

<400> SEQUENCE: 20
cggcgggcac ttcagcatca cctccactgg atatgcgtca ctgatggctt gggcc         55

<210> SEQ ID NO 21
<211> LENGTH: 46
<212> TYPE: DNA
<213> ORGANISM: Artificial Sequence
<220> FEATURE:
<223> OTHER INFORMATION: primer A114R-for

<400> SEQUENCE: 21
cgacaccttc aaccgagagc cacggattgt caggttcttc tcccgg                    46

<210> SEQ ID NO 22
<211> LENGTH: 46
<212> TYPE: DNA
<213> ORGANISM: Artificial Sequence
<220> FEATURE:
<223> OTHER INFORMATION: Primer A114R-rc

<400> SEQUENCE: 22
ccgggagaag aacctgacaa tccgtggctc tcggttgaag gtgtcg                    46

<210> SEQ ID NO 23
<211> LENGTH: 48
<212> TYPE: DNA
<213> ORGANISM: Artificial Sequence
<220> FEATURE:
<223> OTHER INFORMATION: Primer D53A-for

<400> SEQUENCE: 23
tgactgccgt ggggaagctg ctggcgaacc tcaatcagga tgcaccag    48

<210> SEQ ID NO 24
<211> LENGTH: 48
<212> TYPE: DNA
<213> ORGANISM: Artificial Sequence
<220> FEATURE:
<223> OTHER INFORMATION: Primer D53A-rc

<400> SEQUENCE: 24
ctggtgcatc ctgattgagg ttcgccagca gcttccccac ggcagtca    48

<210> SEQ ID NO 25
<211> LENGTH: 49
<212> TYPE: DNA
<213> ORGANISM: Artificial Sequence
<220> FEATURE:
<223> OTHER INFORMATION: H44A-for

<400> SEQUENCE: 25
tggtccagga ggtcagagac agcgcactga ctgccgtggg gaagctgct    49

<210> SEQ ID NO 26
<211> LENGTH: 49
<212> TYPE: DNA
<213> ORGANISM: Artificial Sequence
<220> FEATURE:
<223> OTHER INFORMATION: Primer H44A-rc

<400> SEQUENCE: 26
agcagcttcc ccacggcagt cagtgcgctg tctctgacct cctggacca    49

<210> SEQ ID NO 27
<211> LENGTH: 64
<212> TYPE: DNA
<213> ORGANISM: Artificial Sequence
<220> FEATURE:
<223> OTHER INFORMATION: Primer NLS-1

<400> SEQUENCE: 27
gatgctgaag tgcaagcgcc agcagcaac aaagaaggcc gggcaggcaa agaagaagaa    60
gctt    64

<210> SEQ ID NO 28
<211> LENGTH: 62
<212> TYPE: DNA
<213> ORGANISM: Artificial Sequence
<220> FEATURE:
<223> OTHER INFORMATION: Primer NLS-1-rc

<400> SEQUENCE: 28
ttgctagcca taagcttctt cttctttgcc tgcccggcct tctttgttgc tgctgggcgc    60
tt    62

<210> SEQ ID NO 29

```
<211> LENGTH: 51
<212> TYPE: DNA
<213> ORGANISM: Artificial Sequence
<220> FEATURE:
<223> OTHER INFORMATION: Primer NLS-2

<400> SEQUENCE: 29
gaggtgatgc tgaagtgcga cgcaccgcga ggcaaaaagc cgcgccagg g         51

<210> SEQ ID NO 30
<211> LENGTH: 48
<212> TYPE: DNA
<213> ORGANISM: Artificial Sequence
<220> FEATURE:
<223> OTHER INFORMATION: Primer NLS-2-rc

<400> SEQUENCE: 30
tcctttgcta gccatccctg gcgcgggctt tttgcctcgc ggtgcgtc            48

<210> SEQ ID NO 31
<211> LENGTH: 40
<212> TYPE: DNA
<213> ORGANISM: Artificial Sequence
<220> FEATURE:
<223> OTHER INFORMATION: Primer NLS-3

<400> SEQUENCE: 31
ggtgatgctg aagtgccgaa agtttaagaa gaagtttaag                    40

<210> SEQ ID NO 32
<211> LENGTH: 42
<212> TYPE: DNA
<213> ORGANISM: Artificial Sequence
<220> FEATURE:
<223> OTHER INFORMATION: Primer NLS-3-rc

<400> SEQUENCE: 32
ttctcctttg ctagccatct taaacttctt cttaaacttt cg                 42

<210> SEQ ID NO 33
<211> LENGTH: 40
<212> TYPE: DNA
<213> ORGANISM: Artificial Sequence
<220> FEATURE:
<223> OTHER INFORMATION: Primer NLS-4

<400> SEQUENCE: 33
ggaggtgatg ctgaagtgca gccgcaaacg accgcggccc                    40

<210> SEQ ID NO 34
<211> LENGTH: 39
<212> TYPE: DNA
<213> ORGANISM: Artificial Sequence
<220> FEATURE:
<223> OTHER INFORMATION: Primer NLS-4-rc

<400> SEQUENCE: 34
ttctcctttg ctagccatgg gccgcggtcg tttgcggct                     39

<210> SEQ ID NO 35
<211> LENGTH: 62
<212> TYPE: DNA
<213> ORGANISM: Artificial Sequence
<220> FEATURE:
<223> OTHER INFORMATION: Primer NLS-a-rc

<400> SEQUENCE: 35
```

```
ttaattcatt aaagcttctt cttctttgcc tgcccggcct tctttgttgc tgctgggcgc    60
tt                                                                  62
```

<210> SEQ ID NO 36
<211> LENGTH: 48
<212> TYPE: DNA
<213> ORGANISM: Artificial Sequence
<220> FEATURE:
<223> OTHER INFORMATION: PRIMER NLS-b-rc

<400> SEQUENCE: 36

```
gggtttaatt cattaccctg gcgcgggctt tttgcctcgc ggtgcgtc                 48
```

<210> SEQ ID NO 37
<211> LENGTH: 42
<212> TYPE: DNA
<213> ORGANISM: Artificial Sequence
<220> FEATURE:
<223> OTHER INFORMATION: Primer NLS-c-rc

<400> SEQUENCE: 37

```
agcgggttta attcattact taaacttctt cttaaacttt cg                      42
```

<210> SEQ ID NO 38
<211> LENGTH: 39
<212> TYPE: DNA
<213> ORGANISM: Artificial Sequence
<220> FEATURE:
<223> OTHER INFORMATION: Primer NLS-d-rc

<400> SEQUENCE: 38

```
agcgggttta attcattagg gccgcggtcg tttgcggct                          39
```

<210> SEQ ID NO 39
<211> LENGTH: 68
<212> TYPE: DNA
<213> ORGANISM: Artificial Sequence
<220> FEATURE:
<223> OTHER INFORMATION: Primer P7-for-19p8

<400> SEQUENCE: 39

```
ccaagccatc atcagtgacc actatccagt ggaggtgatg ctgaagtgca tggctagcaa    60
aggagaag                                                            68
```

<210> SEQ ID NO 40
<211> LENGTH: 62
<212> TYPE: DNA
<213> ORGANISM: Artificial Sequence
<220> FEATURE:
<223> OTHER INFORMATION: Primer P8-rc

<400> SEQUENCE: 40

```
ccatctaatt caacaagaat tgggacaact ccagtgaaaa gttcttctcc tttgctagcc    60
at                                                                  62
```

<210> SEQ ID NO 41
<211> LENGTH: 65
<212> TYPE: DNA
<213> ORGANISM: Artificial Sequence
<220> FEATURE:
<223> OTHER INFORMATION: P9-for-19p6

<400> SEQUENCE: 41

```
ccaagccatc agtgacgcat atccagtgga ggtgatgctg aagtgctaat gaattaaacc    60
cgctg                                                                65

<210> SEQ ID NO 42
<211> LENGTH: 51
<212> TYPE: DNA
<213> ORGANISM: Artificial Sequence
<220> FEATURE:
<223> OTHER INFORMATION: Primer V67M-for

<400> SEQUENCE: 42
gcaccagaca cctatcacta cgtgatgagt gagccactgg gacggaacag c              51

<210> SEQ ID NO 43
<211> LENGTH: 51
<212> TYPE: DNA
<213> ORGANISM: Artificial Sequence
<220> FEATURE:
<223> OTHER INFORMATION: Primer V67M-rc

<400> SEQUENCE: 43
gctgttccgt cccagtggct cactcatcac gtagtgatag gtgtctggtg c              51

<210> SEQ ID NO 44
<211> LENGTH: 51
<212> TYPE: DNA
<213> ORGANISM: Artificial Sequence
<220> FEATURE:
<223> OTHER INFORMATION: Primer Y65W-for

<400> SEQUENCE: 44
caggatgcac cagacaccta tcactgggtg gtcagtgagc cactgggacg g              51

<210> SEQ ID NO 45
<211> LENGTH: 51
<212> TYPE: DNA
<213> ORGANISM: Artificial Sequence
<220> FEATURE:
<223> OTHER INFORMATION: Primer Y65W-rc

<400> SEQUENCE: 45
ccgtcccagt ggctcactga ccacccagtg ataggtgtct ggtgcatcct g              51

<210> SEQ ID NO 46
<211> LENGTH: 14
<212> TYPE: DNA
<213> ORGANISM: Artificial Sequence
<220> FEATURE:
<223> OTHER INFORMATION: Recombination site

<400> SEQUENCE: 46
gatcaaacaa gttt                                                      14

<210> SEQ ID NO 47
<211> LENGTH: 21
<212> TYPE: DNA
<213> ORGANISM: Artificial Sequence
<220> FEATURE:
<223> OTHER INFORMATION: Recombination site

<400> SEQUENCE: 47
ctagtttgtt caaacatgtt t                                              21

<210> SEQ ID NO 48
<211> LENGTH: 16
```

```
<212> TYPE: DNA
<213> ORGANISM: Artificial Sequence
<220> FEATURE:
<223> OTHER INFORMATION: Recombination site

<400> SEQUENCE: 48
gtacaaaaaa gttggc                                                         16

<210> SEQ ID NO 49
<211> LENGTH: 9
<212> TYPE: DNA
<213> ORGANISM: Artificial Sequence
<220> FEATURE:
<223> OTHER INFORMATION: Recombination site

<400> SEQUENCE: 49 tttcaaccg                                                                  9

<210> SEQ ID NO 50
<211> LENGTH: 12
<212> TYPE: DNA
<213> ORGANISM: Artificial Sequence
<220> FEATURE:
<223> OTHER INFORMATION: Recombination site

<400> SEQUENCE: 50
ttgtacaaag tg                                                             12

<210> SEQ ID NO 51
<211> LENGTH: 6
<212> TYPE: DNA
<213> ORGANISM: Artificial Sequence
<220> FEATURE:
<223> OTHER INFORMATION: Recombination site

<400> SEQUENCE: 51 tttcac                                                                     6

<210> SEQ ID NO 52
<211> LENGTH: 9
<212> TYPE: DNA
<213> ORGANISM: Artificial Sequence
<220> FEATURE:
<223> OTHER INFORMATION: Recombination site

<400> SEQUENCE: 52 ccaactttc                                                                  9

<210> SEQ ID NO 53
<211> LENGTH: 15
<212> TYPE: DNA
<213> ORGANISM: Artificial Sequence
<220> FEATURE:
<223> OTHER INFORMATION: Recombination site

<400> SEQUENCE: 53
ggttgaaaga acatg                                                          15

<210> SEQ ID NO 54
<211> LENGTH: 700
<212> TYPE: DNA
<213> ORGANISM: Artificial Sequence
<220> FEATURE:
<223> OTHER INFORMATION: Strand of C01

<400> SEQUENCE: 54
```

```
tgggagtttg ttttggcacc aaaatcaacg ggactttcca aaatgtcgta acaactccgc      60
cccattgacg caaatgggcg gtaggcgtgt acggtgggag gtctatataa gcagagctct     120
ctggctaact agagaaccca ctgcttactg gcttatcgaa attaatacga ctcactatag     180
ggagacccaa gctggctagt taagcttgat caaacaagtt tgtacaaaaa agctggcatg     240
aggggcatga agctgctggg ggcgctgctg gcactggcgg ccctactgca ggggccgtg      300 tccccgccaa aaagaaacg caaagtgctg aagatcgcag ccttcaacat ccagacattt      360
ggggagacca agatgtccaa tgccaccctc gtcagctaca ttgtgcagat cctgagccgc     420
tatgacatcg ccctggtcca ggaggtcaga gacagccacc tgactgccgt ggggaagctg     480
ctggacaacc tcaatcagga tgcaccagac acctatcact acgtggtcag tgagccactg     540
ggacggaaca gctataagga gcgctacctg ttcgtgtaca ggcctgacca ggtgtctgcg     600
gtggacagct actactacga tgatggctgc gagccctgcg ggaacgacac cttcaaccga     660
gagccagcca ttgtcaggtt cttctcccgg ttcacagagg                            700

<210> SEQ ID NO 55
<211> LENGTH: 700
<212> TYPE: DNA
<213> ORGANISM: Artificial Sequence
<220> FEATURE:
<223> OTHER INFORMATION: Strand of C01

<400> SEQUENCE: 55
accctcaaac aaaaccgtgg ttttagttgc cctgaaaggt tttacagcat tgttgaggcg      60
gggtaactgc gtttacccgc catccgcaca tgccaccctc cagatatatt cgtctcgaga     120
gaccgattga tctcttgggt gacgaatgac cgaatagctt taattatgct gagtgatatc     180
cctctgggtt cgaccgatca attcgaacta gtttgttcaa acatgttttt tcgaccgtac     240
tccccgtact tcgacgaccc ccgcgacgac cgtgaccgcc gggatgacgt ccccggcac     300 aggggcggct ttttctttgc gtttcacgac ttctagcgtc ggaagttgta ggtctgtaaa     360
cccctctggt tctacaggtt acggtgggag cagtcgatgt aacacgtcta ggactcggcg     420
atactgtagc gggaccaggt cctccagtct ctgtcggtgg actgacggca ccccttcgac     480
gacctgttgg agttagtcct acgtggtctg tggatagtga tgcaccagtc actcggtgac     540
cctgccttgt cgatattcct cgcgatggac aagcacatgt ccggactggt ccacagacgc     600
cacctgtcga tgatgatgct actaccgacg ctcgggacgc ccttgctgtg gaagttggct     660
ctcggtcggt aacagtccaa gaagagggcc aagtgtctcc                            700
```